(12) United States Patent
Schoenafinger et al.

(10) Patent No.: US 7,727,989 B2
(45) Date of Patent: *Jun. 1, 2010

(54) 4-BENZIMIDAZOL-2-YL-PYRIDAZINE-3-NE-DERIVATIVES, PRODUCTION AND USE THEREOF IN MEDICAMENTS

(75) Inventors: Karl Schoenafinger, Alzenau (DE); Swen Hoelder, Frankfurt (DE); David William Will, Kriftel (DE); Hans Matter, Langenselbold (DE); Guenter Mueller, Sulzbach (DE); Martin Bossart, Frankfurt (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/467,639

(22) Filed: Aug. 28, 2006

(65) Prior Publication Data

US 2007/0072866 A1 Mar. 29, 2007

Related U.S. Application Data

(63) Continuation of application No. PCT/EP2005/002179, filed on Mar. 2, 2005.

(30) Foreign Application Priority Data

Mar. 2, 2004 (DE) ................. 10 2004 010 194

(51) Int. Cl.
*A61K 31/501* (2006.01)
*C07D 401/14* (2006.01)
*C07D 413/14* (2006.01)
*A61K 31/5355* (2006.01)
*A61K 31/553* (2006.01)

(52) U.S. Cl. .................. 514/252.03; 544/238; 544/122; 514/234.5; 514/211.15; 540/598

(58) Field of Classification Search ............ 514/252.06, 514/252.03, 234.5, 211.15; 544/238, 122; 540/598

See application file for complete search history.

(56) References Cited

U.S. PATENT DOCUMENTS

| | | | | |
|---|---|---|---|---|
| 7,189,690 B2 * | 3/2007 | Rosen et al. | ................. | 514/2 |
| 7,196,109 B2 * | 3/2007 | Lesuisse et al. | ............. | 514/403 |
| 7,229,776 B2 * | 6/2007 | Holvoet et al. | ................ | 435/7.1 |
| 7,229,999 B2 * | 6/2007 | Hebeisen et al. | ............. | 514/256 |
| 7,232,827 B2 * | 6/2007 | Lochead et al. | .......... | 514/259.1 |
| 7,232,828 B2 * | 6/2007 | Pershadsingh | ............ | 514/259.1 |
| 7,232,897 B2 * | 6/2007 | Hotamisligil et al. | ........ | 536/7.4 |
| 7,232,901 B2 * | 6/2007 | Mastalerz et al. | ............ | 544/183 |
| 7,232,904 B2 * | 6/2007 | Kato et al. | ................. | 544/296 |
| 7,232,906 B2 * | 6/2007 | Zhang et al. | ................ | 544/333 |
| 7,232,929 B2 * | 6/2007 | Bialer et al. | ................. | 564/86 |
| 7,232,939 B2 * | 6/2007 | Herrmann et al. | ........... | 800/279 |

FOREIGN PATENT DOCUMENTS

| | | |
|---|---|---|
| EP | 1061077 | 12/2000 |
| WO | WO 01/74771 | 10/2001 |
| WO | WO 03/035085 | 5/2003 |
| WO | WO 03/066629 | 8/2003 |
| WO | WO 2004/046117 | 6/2004 |
| WO | WO 2005085231 | * 2/2005 |

OTHER PUBLICATIONS

Bhat, et al., J. Neurochem., 2004, 89, 1313-1317.*
Martinez, et al., Med. Res. Rev., vol. 22, No. 4, 373-384 (2002).*
Buée, et al., Brain Res. Rev., 33 (2000) 95-130.*
Henriksen, et al., Curr. Drug Targets, 2006, 7 (11), 1435-42 (Abst.).*
Kwok, et al., Annals Neurol., vol. 58, #6, Dec. 2005, pp. 829-839.*
Mohammad, et al., Europ. J. Pharmacol., vol. 584, # 1, Apr. 14, 2008, 185-191.*

* cited by examiner

*Primary Examiner*—James O Wilson
*Assistant Examiner*—Cecilia M Jaisle
(74) *Attorney, Agent, or Firm*—Jiang Lin

(57) ABSTRACT

The present invention relates to kinase inhibitor compounds and derivatives thereof as well as compositions comprising them consisting of the structure of formula I:

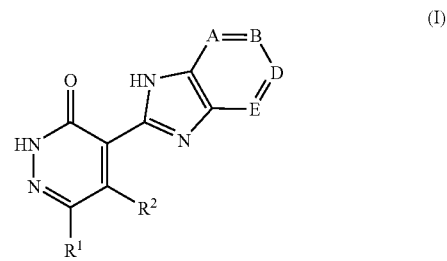

(I)

Wherein R1, R2, A, B, D and E are defined herein. These 4-benzimidazol-2-ylpyridazin-3-ones and their derivatives and compositions comprising them are useful in the treatment of neurological disorders such as Alzheimers' disease, Parkinsons' disease, obesity, hypertension and the like. These pyridazinone derivatives particularly inhibit the metabolic activity of glycogen synthase kinase-3 β (GSK-3β) which is believed to cause the neurodegeneration that results in these diseases.

11 Claims, No Drawings

4-BENZIMIDAZOL-2-YL-PYRIDAZINE-3-ONE-ERIVATIVES, PRODUCTION AND USE THEREOF IN MEDICAMENTS

FIELD OF THE INVENTION

The present invention relates generally to pharmaceutical compounds and compositions for the treatment of a number of metabolic disorders that cause diseases of the central nervous system. More specifically, the present invention relates to kinase inhibitor compounds and derivatives thereof as well as compositions comprising them for the treatment of a number of neurological disorders such as Alzheimers' disease, Parkinsons' disease and the like.

BACKGROUND OF THE INVENTION

Numerous compounds and medicaments able to act at particular (different) points in the biochemical process associated with the respective pathological state have been disclosed for the treatment of diseases such as diabetes or Alzheimer's. To date, only a few compounds able to bring about an inhibition of the enzyme glycogen synthase kinase -3β(GSK-3β) have been disclosed for the treatment of metabolic disorders.

Thus, WO 04/046117 discloses pyridazinone derivatives suitable for inhibiting GSK-3β. The pyridazinone derivatives described therein differ from the compounds of the present invention in that, in place of a benzimidazole residue (or a derivative thereof), they have an amide substituent in position 4 of the pyridazinone which can be linked both via the amide carbon atom and via the amide nitrogen atom to the basic pyridazinone structure.

In addition, numerous pyridazinone derivatives are described in the literature but differ from the compounds of the invention through a different substitution pattern and (in some cases) different indications. Thus, it is possible from the general formula disclosed in WO 01/74786 to derive pyridazinone derivatives which, although they may have a benzimidazole substituent in position 4, on the other hand they have a sulfonamide group in position 5, in contrast to the compounds of the present invention. The compounds described in WO 01/74786 have an inhibitory effect on phosphodiesterase-7 and can be used in the treatment of autoimmune diseases.

JP-A 09 216883 discloses pyridazinone derivatives which can be used for the treatment of heart failure or high blood pressure. The pyridazinone derivatives described therein have in position 6 a pyrazolo[1,5-a]pyridine substituent which is in turn substituted in position 2 by aryl, preferably phenyl. The pyridazinone ring itself is additionally substituted in position 2 by substituents such as hydrogen, lower alkyl or a heterocycle, while position 4 has substituents such as hydrogen, acyl, cyano, heterocyclyl, amino or a protected amino group. If the substituent in position 4 is a heterocycle, this preferably has 3 to 8 ring members and is saturated. A heterocyclic group is not, however, among the preferred substituents in position 4 of the pyridazinone ring of the compounds disclosed and claimed in this document.

Compounds explicitly disclosed in JP-A 09 216883 are not an aspect of the present invention.

WO 03/059891 by contrast discloses pyridazinone derivatives which can be used to treat diseases which are caused or intensified by unregulated p38 MAP kinase and/or TNF activity. The compounds described therein are suitable for example for the treatment of inflammations, of diabetes, of Alzheimer's disease or of cancer. They differ from the compounds of the invention in that the nitrogen in position 2 is mainly substituted by alkyl, aryl or heteroaryl and in that a heteroaryl substituent such as benzimidazole is not defined for position 4 of the pyridazinone.

Bicyclic heterocycles having an aggregation inhibiting effect are described in EP-A 0 639 575. It is possible from the general formula (I) specified therein to derive for the bicyclic system having substituent a benzimidazole derivative which must have at least one further ring nitrogen atom. It is additionally possible to derive for the substituent B theoretically a pyridazinone derivative which in turn must obligatorily be provided with a multi-membered substituent which obligatorily comprises a 1,4-cyclohexylene or 1,4-cyclohex-3-enylene group and a carbonyl group. It is thus evident that the compounds of the invention are not disclosed by EP-A 0 639 575 and compounds explicitly disclosed by EP-A 0 639 575 are not an aspect of the present invention However, all of the documents discussed above are hereby incorporated by reference.

The compounds of general formula (I) are kinase inhibitors and can therefore be employed for the treatment of diseases, which may result from an abnormal activity of kinases. Abnormal kinase activity, may also be found in for example, that of PI3K, AkT, GSK-3β kinase enzyme

SUMMARY OF THE INVENTION

The present invention relates to kinase inhibitor compounds and derivatives thereof as well as compositions comprising them for the treatment of a number of neurological disorders such as Alzheimers'disease, Parkinsons'disease and the like. These pyridazinone derivatives particularly inhibit the metabolic activity of the enzyme glycogen synthase kinase —3β (GSK-3β) which is believed to cause the neurodegeneration that results in these diseases.

DETAILED DESCRIPTION OF THE INVENTION

The compounds of general formula (I) are kinase inhibitors and can therefore be employed for the treatment of diseases, which may result from an abnormal activity of kinases. As abnormal kinase activity, there may be mentioned, for example, that of PI3K, AkT, GSK-3β and the like. In particular, compounds according to the present invention can be used for the inhibition of the kinase GSK-3β. This effect is particularly relevant for the treatment of metabolic diseases such as type II diabetes or neurodegenerative diseases such as Alzheimer's disease.

Furthermore, compounds according to the general formula (I) have an inhibitory effect in respect of the phosphorylation of the tau-protein. This effect is particularly relevant for the treatment of neurodegenerative diseases such as Alzheimer's disease.

Examples of diseases which can be treated with the compounds according to the present invention, include: neurodegenerative diseases, strokes, cranial and spinal traumas and peripheral neuropathies, obesity, metabolic diseases, type II diabetes, essential hypertension, atherosclerotic cardiovascular diseases, polycystic ovary syndrome, syndrome X, immunodeficiency or cancer. Neurodegenerative diseases are preferably: Alzheimer's disease, Parkinson's disease, frontoparietal dementia, cortico-basal degeneration and Pick's disease There is a need then, for compounds which have an inhibitory effect on the metabolic enzyme glycogen synthase kinase (GSK-3β). The invention relates to compounds of the general formula (I) below, wherein the definitions of the substituents A, B, D, E, $R^1$ and $R^2$ are detailed supra, and to the pharmaceutically acceptable salts thereof, processes for preparing these compounds and to their administration and use in the treatment of metabolic diseases of the central nervous system (CNS). These compounds are known as kinase inhibitors, especially inhibitors of the kinase GSK-3β (glycogen synthase kinase 3β).

More specifically, these compounds are 4-benzimidazol-2-ylpyridazin-3-ones and their derivatives. The compounds claimed are of the following general formula (I)

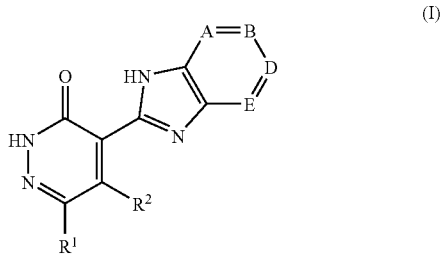

(I)

wherein:
A is $CR^3$ or N;
B is $CR^4$ or N;
D is $CR^5$ or N;
E is $CR^6$ or N; and
wherein a maximum of three of the substituents A, B, D and E can simultaneously be N;
$R^1$ is halogen;
    unsubstituted or at least monosubstituted $C_1$-$C_{10}$-Alkyl,
    where the substituents are selected from the group consisting of: halogen, CN, $NO_2$, —$OR^7$, —$C(O)R^7$, —$C(O)OR^7$, —O—$C(O)R^7$, —$NR^7R^8$, —NHC(O)$R^7$, —C(O)$NR^7R^8$, —NHC(S)$R^7$, —C(S)$NR^7R^8$, —$SR^7$, —$S(O)R^7$, —$SO_2R^7$, —$NHSO_2R^7$, —$SO_2NR^7R^8$, —O—$SO_2R^7$, —$SO_2$—O—$R^7$, aryl, heteroaryl, heterocyclyl, tri-fluoromethyl and tri-fluoromethoxy,
    and heterocyclyl, aryl and heteroaryl may in turn be at least monosubstituted by $C_1$-$C_6$-alkyl, $C_1$-$C_6$-alkoxy, halogen, tri-fluoromethyl, tri-fluoromethoxy or OH;
    or unsubstituted or at least monosubstituted heterocyclyl, aryl or heteroaryl,
    where the substituents are selected from the group consisting of: halogen, —CN, $NO_2$, —$CH_2$—$R^7$, —$CH_2$—$NH_2$, —$CH_2$—NH($C_1$-$C_6$-alkyl), —$CH_2$—N($C_1$-$C_6$-alkyl)$_2$, —$CH_2$—OH, —$CH_2$—O—($C_1$-$C_6$-alkyl), —$OR^7$, —C(O) $R^7$, —$C(O)OR^7$, —O—C(O)$R^7$, —$NR^7R^8$, —NHC(O)$R^7$, —C(O)$NR^7R^8$, —NHC(S)$R^7$, —C(S)$NR^7R^8$, —$SR^7$, —$S(O)R^7$, —$SO_2R^7$, —$NHSO_2R^7$, —$SO_2NR^7R^8$, —O—$SO_2R^7$, —$SO_2$—O—$R^7$, aryl, heteroaryl, tri-fluoromethyl and tri-fluoromethoxy, and aryl and heteroaryl may in turn be at least monosubstituted by $C_1$-$C_6$-alkyl, $C_1$-$C_6$-alkoxy, halogen, tri-fluoromethyl, tri-fluoromethoxy or OH;
$R^2$ is hydrogen or $C_1$-$C_{10}$-alkyl;
$R^3$ is selected from the group consisting of:
    hydrogen, halogen, —CN, $NO_2$, —$CH_2$—$R^8$, —$CH_2$—$NH_2$, —$CH_2$—NH($C_1$-$C_6$- alkyl), —$CH_2$—N($C_1$-$C_6$-alkyl)$_2$, —$CH_2$—OH, —$CH_2$—O—($C_1$-$C_6$—alkyl), -$OR^8$, —$C(O)R^8$, —$C(O)OR^8$, —O—C(O) $R^8$, —$NR^7R^8$; —NHC(O)$R^8$, —C(O)$NR^7R^8$, —NHC(S)$R^8$, —C(S)$NR^7R^8$, —$SR^8$, —$S(O)R^8$, —$SO_2R^8$, —$NHSO_2R^8$, —$SO_2NR^7R^8$, —O—$SO_2R^8$, —$SO_2$—O—$R^8$, aryl, heteroaryl, heterocyclyl, tri-fluoromethyl and tri-fluoromethoxy,
    and heterocyclyl, aryl and heteroaryl may in turn be at least monosubstituted by $C_1$-$C_6$-alkyl, $C_1$-$C_6$-alkoxy, oxo, halogen, tri-fluoromethyl, tri-fluoromethoxy or OH;
$R^4$ is selected from the group consisting of:
    hydrogen, halogen, —CN, $NO_2$, —$CH_2$—$R^8$, —$CH_2$—$NH_2$, —$CH_2$—NH($C_1$-$C_6$-alkyl), —$CH_2$—N($C_1$—$C_6$—alkyl)$_2$, —$CH_2$—OH, —$CH_2$—O—($C_1$—$C_6$—alkyl), —$OR^8$, —$C(O)R^8$, —$C(O)OR^8$, —O—$C(O)R^8$, —$NR^7R^8$; —NHC(O)$R^8$, —C(O)$NR^7R^8$, —$SR^8$, —$S(O)R^8$, —$SO_2R^8$, —$NHSO_2R^8$, —$SO_2NR^7R^8$, —O—$SO_2R^8$, —$SO_2$—O—$R^8$, aryl, heteroaryl, heterocyclyl, tri-fluoromethyl and tri-fluoromethoxy,
    and heterocyclyl, aryl and heteroaryl may in turn be at least monosubstituted by $C_1$-$C_6$-alkyl, $C_1$-$C_6$-alkoxy, oxo, halogen, tri-fluoromethyl, tri-fluoromethoxy or OH;
$R^5$ is selected from the group consisting of:
    hydrogen, halogen, —CN, $NO_2$, —$CH_2$—$R^8$, —$CH_2$—$NH_2$, —$CH_2$—NH($C_1$-$C_6$-alkyl), —$CH_2$—N($C_1$-$C_6$-alkyl)$_2$, —$CH_2$—OH, —$CH_2$—O—($C_1$-$C_6$-alkyl), —$OR^8$, —$C(O)R^8$, —$C(O)OR^8$, —O—$C(O)R^8$, —$NR^7R^8$; —NHC(O)$R^8$, —C(O)$NR^7R^8$, —NHC(S)$R^8$, —C(S)$NR^7R^8$, —$SR^8$, —$S(O)R^8$, —$SO_2R^8$, —$NHSO_2R^8$, —$SO_2NR^7R^8$, —O—$SO_2R^8$, —$SO_2$—O—$R^8$, aryl, heteroaryl, heterocyclyl, tri-fluoromethyl and tri-fluoromethoxy,
    and heterocyclyl, aryl and heteroaryl may in turn be at least monosubstituted by $C_1$-$C_6$-alkyl, $C_1$-$C_6$-alkoxy, oxo, halogen, tri-fluoromethyl, tri-fluoromethoxy or OH;
$R^6$ is selected from the group consisting of:
    hydrogen, halogen, —CN, $NO_2$, —$CH_2$—$R^8$, —$CH_2$—$NH_2$, —$CH_2$—NH($C_1$-$C_6$-alkyl), —$CH_2$—N($C_1$-$C_6$-alkyl)$_2$, —$CH_2$—OH, —$CH_2$—O—($C_1$-$C_6$-alkyl), —$OR^8$, —$C(O)R^8$, —$C(O)OR^8$, —O—$C(O)R^8$, —$NR^7R^8$; —NHC(O)$R^8$, —C(O)$NR^7R^8$, NHC(S)$R^8$, —C(S)$NR^7R^8$, —$SR^8$, —$S(O)R^8$, —$SO_2R^8$, —$NHSO_2R^8$, —$SO_2NR^7R^8$, —O—$SO_2R^8$, —$SO_2$—O—$R^8$, aryl, heteroaryl, heterocyclyl, tri-fluoromethyl and tri-fluoromethoxy,
    and heterocyclyl, aryl and heteroaryl may in turn be at least monosubstituted by $C_1$-$C_6$-alkyl, $C_1$-$C_6$-alkoxy, oxo, halogen, tri-fluoromethyl, tri-fluoromethoxy or OH;
$R^7$ is H;
    an unsubstituted or at least monosubstituted $C_1$-$C_{10}$-alkyl, $C_2$-$C_{10}$-alkenyl, $C_2$-$C_{10}$-alkynyl, heterocyclyl, aryl or heteroaryl,
    where the substituents are selected from the group consisting of: heteroaryl, heterocyclyl, aryl, oxo, halogen, OH, $C_1$-$C_{10}$-alkoxy, ($C_1$-$C_{10}$-alkyl)thio-, —C(O)OH, —C(O)O—($C_1$-$C_6$-alkyl), —C(O)$NH_2$, C—(O)NH($C_1$-$C_6$-alkyl), —C(O)N($C_1$-$C_{10}$-alkyl)$_2$, tri-fluoromethyl, tri-fluoromethoxy; —CN, —$NH_2$, —NH($C_1$-$C_{10}$-alkyl) and —N($C_1$-$C_{10}$-alkyl)$_2$,
    and heterocyclyl, aryl and heteroaryl may in turn be at least monosubstituted by $C_1$-$C_6$-alkyl, $C_1$-$C_6$-alkoxy, oxo, tri-fluoromethyl, tri-fluoromethoxy, fluorine, chlorine or OH;
$R^8$ is H;
    unsubstituted or at least monosubstituted $C_1$-$C_{10}$-alkyl, $C_2$-$C_{10}$-alkenyl, $C_2$-$C_{10}$-alkynyl, heterocyclyl, aryl or heteroaryl, where the substituents are selected from the group consisting of: heteroaryl, heterocyclyl, aryl, halogen, OH, oxo, $C_1$-$C_{10}$-alkoxy, ($C_1$-$C_{10}$-alkyl)thio-, —C(O)OH, —C(O)O—($C_1$-$C_6$-alkyl), —C(O)$NH_2$, —C(O)NH($C_1$-$C_6$-alkyl), —C(O)N($C_1$-$C_{110}$-alkyl)$_2$, tri-fluoromethyl, tri-fluoromethoxy, —CN, —$NH_2$, —NH($C_1$-$C_{10}$-alkyl) and —N($C_1$-$C_{10}$-alkyl)$_2$, and heterocyclyl, aryl and heteroaryl may in turn be at least monosubstituted by $C_1$-$C_6$-alkyl, $C_1$-$C_6$-alkoxy, oxo, tri-fluoromethyl, tri-fluoromethoxy, fluorine, chlorine or OH;

Heteroaryl is a 5 to 10-membered, aromatic, mono- or bicyclic heterocycle which comprises one or more heteroatoms selected from N, O and S;

Aryl is a 5 to 10-membered, aromatic, mono- or bicyclic system;

Heterocyclyl is a 5 to 10-membered, nonaromatic, mono- or bicyclic heterocycle which comprises one or more heteroatoms selected from N, O and S;

or a physiologically tolerated salt thereof; with the proviso that $R^1$ is not unsubstituted or at least monosubstituted pyrazolo[1,5-a]pyridinyl.

The above meanings of the substituents $R^1$ to $R^8$, A, B, D, E, heteroaryl, heterocyclyl and aryl are the basic meanings (definitions) of the respective substituents.

If in the compounds of formula (I) groups, fragments, residues or substituents such as, for example, aryl, heteroaryl, alkyl, alkoxy etc., are present several times, they all independently from each other have the meanings indicated and may hence, in each individual case, be identical with or different from each other. The following comments apply to (for example) aryl as well as to any other residue independently from its classification as aryl group, -substituent, -fragment or -residue. One example is the —N($C_1$-$C_6$-alkyl)$_2$ group and the (di($C_1$-$C_6$-alkyl)amino group) in which the alkyl substituents may be identical or different (for instance 2×ethyl or 1×propyl and 1×hexyl).

If in the compounds described above, according to formula (I) a substituent, for example aryl, is unsubstituted or at least monosubstituted with a group of additional moieties for example, $C_1$-$C_6$-alkyl, $C_1$-$C_6$-alkoxy, halogen etc., then here is a poly-substitution of aryl, and the selection from the group of additional substituents is independent from each other. Thus, all combinations of further substituents are comprised in the case of, for example, a disubstitution of aryl. Therefore, aryl may be substituted twice with ethyl, aryl may be monosubstituted with methyl or ethoxy, aryl may be monosubstituted with ethyl or fluoro, respectively, aryl may be substituted twice with methoxy, etc.

Alkyl residues may be linear or branched, acyclic or cyclic. This also applies when they are part of other groups, for example in alkoxy groups, ($C_1$-$C_{10}$-alkyl-O—), alkoxycarbonyl groups or amino groups, or when they are substituted.

Examples for alkyl groups are: methyl, ethyl, propyl, butyl, pentyl, hexyl, heptyl, octyl, nonyl, decyl. This comprises both the n-isomers of these residues and isopropyl, isobutyl, isopentyl, sec-butyl, tert-butyl, neopentyl, 3,3-dimethylbutyl etc.

Furthermore, unless stated otherwise, the term alkyl here also includes unsubstituted alkyl residues as well as alkyl residues which are substituted by one or more, for example one, two, three or four, identical or different residues, for example aryl, heteroaryl, alkoxy or halogen. The additional substituents may be present in any desired position of the alkyl residue. The term alkyl here also includes cycloalkyl residues and cycloalkyl-alkyl residues (alkyl substituted by cycloalkyl), where cycloalkyl contains at least three carbon atoms. Examples for such cycloalkyl residues are cyclopropyl, cyclobutyl, cyclopentyl, cyclohexyl, cycloheptyl, cyclooctyl, cyclononyl and cyclodecyl. Optionally, these may also be polycyclic ring systems, such as decalinyl, norbornanyl, bornanyl or adamantanyl. The cycloalkyl residues may be unsubstituted or optionally substituted by one or more further residues, as exemplified above in the case of the alkyl residues.

Examples for alkenyl and alkynyl groups are vinyl, 1-propenyl, 2-propenyl (allyl), 2-butenyl, 2-methyl-2-propenyl, 3-methyl-2-butenyl, ethynyl, 2-propynyl (propargyl), 2-butynyl or 3-butynyl. The term alkenyl here also expressly includes cycloalkenyl residues and cycloalkenyl-alkyl-residues (alkyl substituted by cycloalkenyl) containing at least three carbon atoms. Examples for cycloalkenyl are cyclopentenyl, cyclohexenyl, cycloheptenyl and cyclooctenyl.

The alkenyl residues may have 1 to 3 conjugated or unconjugated double bonds (thus also alk-dienyl- as well as alk-trienyl-residues), preferably one double bond in a straight or branched chain; the same applies to alkynyl residues in respect of triple bonds. The alkenyl and alkynyl residues may be unsubstituted or optionally substituted by one or more further residues, as exemplified above in the case of the alkyl residues.

Unless stated otherwise, the above-mentioned aryl, heteroaryl and heterocyclyl residues may be unsubstituted or may carry one or more, for example one, two, three or four of the substituents indicated in the above definition, which substituents may be in any desired position. In monosubstituted phenyl residues, for example, the substituent may be in the 2-position, the 3-position or the 4-position, in disubstituted phenyl residues the substituents may be in 2,3-position, 2,4-position, 2,5-position, 2,6-position, 3,4-position or 3,5-position. In tri-substituted phenyl residues, the substituents may be in 2,3,4-position, 2,3,5-position, 2,3,6-position, 2,4,5-position, 2,4,6-position or 3,4,5-position. In fourfold substituted phenyl residues, the substituents may be in the 2,3,4,5-position, the 2,3,4,6-position, or the 2,3,5,6-position.

The above definitions as well as the following definitions relating to monovalent residues equally apply to the divalent residues phenylene, naphthylene and heteroarylene. Those divalent residues (fragments) may be attached to the adjacent groups by any ring carbon atom. In the case of a phenylene residue, this may be in 1,2-position (ortho-phenylene), 1,3-position (meta-phenylene) or 1,4-position (para-phenylene). In the case of 5-membered aromatics containing one heteroatom such as, for example, thiophene or furan, the two free bonds may be in the 2,3-position, 2,4-position, 2,5-position or 3,4-position. A divalent residue derived from a 6-membered aromatic with a heteroatom, such as for example pyridine, may be a 2,3-, 2,4-, 2,5-, 2,6-, 3,4- or 3,5-pyridinediyl residue. In the case of unsymmetrical divalent residues the present invention includes all positional isomers, i. e., in the case of a 2,3-pyridinediyl residue, for example, it includes the compound in which the one adjacent group is present in the 2-position and the other adjacent group is present in the 3-position as well as the compound in which the one adjacent group is present in the 3-position and the other adjacent group is present in the 2-position.

Unless stated otherwise, heteroaryl residues, heteroarylene residues, heterocyclyl residues, heterocyclylene residues and rings which are formed by two groups bonded to a nitrogen are preferably derived from completely saturated, partially unsaturated or completely unsaturated heterocycles (i.e. heterocycloalkanes, heterocycloalkenes, heteroaromatics), which contain one, two, three or four heteroatoms, which may be identical or different; more preferably they are derived from heterocycles which contain one, two, or three, in particular one or two, heteroatoms, which may be identical or different. Unless stated otherwise, the heterocycles may be monocyclic or polycyclic, for example monocyclic, bicyclic or tricyclic. Preferably they are monocyclic or bicyclic. The rings preferably are 5-membered rings, 6-membered rings or 7-membered rings particularly preferably 5-membered rings or 6-membered rings. In the case of polycyclic heterocycles containing two or more heteroatoms, they may all be within the same ring or within different rings.

According to the present invention, heteroaryl is a residue derived from mono- or bicyclic aromatic heterocycles. Examples of heteroaryl are: pyrrolyl, furanyl (=furyl), thiophenyl (=thienyl), imidazolyl, pyrazolyl, 1,2,3-triazolyl, 1,2,4-triazolyl, 1,3-oxazolyl (=oxazolyl), 1,2-oxazolyl (=isoxazolyl), oxadiazolyl, 1,3-thiazolyl (=thiazolyl), 1,2-thiazolyl (=isothiazolyl), tetrazolyl, pyridinyl (=pyridyl) pyridazinyl, pyrimidinyl, pyrazinyl, 1,2,3-triazinyl, 1,2,4-triazinyl, 1,3,5-triazinyl, 1,2,4,5-tetrazinyl, indazolyl, indolyl, benzothiophenyl, benzofuranyl, benzothiazolyl, benzimidazolyl, quinolinyl (=quinolyl), isoquinolinyl (=isoquinolyl), quinazolinyl, cinnolinyl, quinoxalinyl, phthalazinyl, thienothiophenyl, 1,8-naphthyridinyl, other naphthyridinyls, purinyl, pteridinyl or thiazolo[3,2-b][1,2,4]-triazolyl. In the case it is not a monocycle, each of the above heteroaryls includes for its second ring also its saturated form (perhydro form) or its partially unsaturated form (for example in the dihydro form or the tetrahydro form) or its maximally unsaturated (nonaromatic form) where the respective forms are known and stable. The term "heteroaryl" as used herein comprises therefore, for example, bicyclic residues in which both rings are aromatic as well as bicyclic residues in which only one ring is aromatic. Such examples for heteroaryl are: 3H-indolinyl, 2(1H)-quinolinonyl, 4-oxo-1,4-dihydroquinolinyl, 2H-1-oxoisoquinolyl, 1,2-dihydroquinolinyl, 3,4-dihydroquinolinyl, 1,2-dihydroisoquinolinyl, 3,4-dihydroisoquinolinyl, chromonyl, chromanyl, 1,3-benzodioxolyl, oxindolyl, 1,2,3,4-tetrahydroisoquinolinyl, 1,2,3,4-tetrahydroquinolinyl, 5,6-dihydroquinolyl, 5,6-dihydroisoquinolyl, 5,6,7,8-tetrahydroquinolinyl or 5,6,7,8-tetrahydroisoquinolyl.

According to the present invention, heterocyclyl is a residue derived from mono- or bicyclic nonaromatic heterocycles. Nonaromatic heterocycles comprise in the following especially heterocycloalkanes (completely saturated heterocycles) as well as heterocycloalkenes (partially unsaturated heterocycles). In the case of heterocycloalkenes there are also included compounds having two or more double bonds, which may optionally be conjugated. Examples of heterocyclyl are: pyrrolidinyl, piperidinyl, piperazinyl, imidazolidinyl, pyrazolidinyl, isothiazolidinyl, thiazolidinyl, isoxazolidinyl, oxazolidinyl, tetrahydrofuranyl, tetrahydrothiophenyl, 1,3-dioxolanyl, 1,4-dioxinyl, pyranyl, thiopyranyl, tetrahydro-1,2-oxazinyl, tetrahydro-1,3-oxazinyl, morpholinyl, thiomorpholinyl, 1,2-thiazinyl, 1,3-thiazinyl, 1,4-thiazinyl, azepinyl, 1,2-diazepinyl, 1,3-diazepinyl, 1,4-diazepinyl, 1,3-oxazepinyl, 1,3-thiazepinyl, azepanyl, 2-oxo-azepanyl, 1,4-oxazepanyl, 1,2,3,4-tetrahydropyridinyl, 1,2-dihydropyridinyl, 1,4-dihydropyridinyl, dihydro-pyridinonlyl such as 6-oxo-1,6-dihydropyridinyl (=1,6-dihydropyridonyl) or 2-oxo-1,2-dihydropyridinyl (=1,2-dihydropyridonyl), 1,2,3,6-tetrahydropyridinyl, 4(3H)-pyrimidonyl, 1,4,5,6-tetrahydropyrimidinyl, 2-pyrrolinyl, 3-pyrrolinyl, 2-imida-zolinyl, 2-pyrazolinyl, 3,4-dihydro-2H-pyranyl, dihydrofuranyl, 7-oxa-bicyclo[2.2.1]heptenyl, dihydrothiophenyl or dihydrothiopyranyl. The degree of saturation of heterocyclic groups is indicated in their individual definitions.

Substituents which may be derived from these heterocycles may be attached via any suitable carbon atom and be provided with further substituents. Residues derived from nitrogen heterocycles may carry a hydrogen atom or another substituent on a corresponding nitrogen atom, and examples include pyrrole, imidazole, pyrrolidine, morpholine, piperazine residues, etc. Those nitrogen heterocyclic residues may also be attached via the ring nitrogen atom, in particular if the respective heterocyclic residue is bonded to a carbon atom. For example, a thienyl residue may be present as 2-thienyl or 3-thienyl, a piperidinyl residue as 1-piperidinyl (=piperidino), 2-piperidinyl, 3-piperidinyl or 4-piperidinyl. Suitable nitrogen heterocycles may also be present as N-oxides or as quarternary salts containing a counter ion which is derived from a physiologically acceptable acid. Pyridyl residues, for example, may be present as pyridine N-oxides. Suitable sulfur-containing heterocycles may be present as S-oxide or S,S-dioxide.

According to the present invention, aryl is a residue derived from mono- or bicyclic aromatics, which do not contain any ring heteroatoms. Where it is not a monocycle, the term aryl includes for its second cycle also its saturated form (perhydro form) or its partially unsaturated form (for example in the dihydro form or the tetrahydro form) where the respective forms are known and stable. The term aryl as used herein comprises therefore, for example, bicyclic residues in which both rings are aromatic as well as bicyclic residues in which only one ring is aromatic. Examples for aryl are: phenyl, naphthyl, indanyl, 1,2-dihydronaphthenyl, 1,4-dihydronaphthenyl, indenyl or 1,2,3,4-tetrahydronaphthyl.

Arylalkyl (such as aryl-($C_1$-$C_6$-alkyl)-) means an alkyl residue (such as $C_1$-$C_6$-alkyl) which in turn is substituted by an aryl radical. Heteroarylalkyl such as (heteroaryl-($C_1$-$C_6$-alkyl)-) means an alkyl residue (such as $C_1$-$C_6$-alkyl) which in turn is substituted by a heteroaryl residue. Heterocyclylalkyl (such as heterocyclyl-($C_1$-$C_6$-alkyl)-) means an alkyl residue (such as $C_1$-$C_6$-alkyl) which in turn is substituted by a heterocyclyl residue. Such arylalkyl, heteroarylalkyl or heterocyclylalkyl residues may in turn be a substituent of another substituent or fragment (such as heterocyclyl-($C_1$-$C_6$-alkyl)-NH—), meaning that a substituent or fragment (such as —NH—) may in turn be substituted by a heterocyclylalkyl residue (such as heterocyclyl-($C_1$-$C_6$-alkyl)-). Further possible substitution for an alkyl radical also include examples such as $H_2N$—($C_1$-$C_6$-alkyl)-, ($C_1$-$C_6$-alkyl)HN—($C_1$-$C_6$-alkyl)- or ($C_1$-$C_6$-alkyl)$_2$N—($C_1$-$C_6$-alkyl)-, meaning an alkyl residue (such as $C_1$-$C_6$-alkyl) which in turn is substituted by —$NH_2$, —NH($C_1$-$C_6$-alkyl) or —N($C_1$-$C_6$-alkyl)$_2$ respectively. In addition, a residue such as ($C_1$-$C_6$-alkyl)HN—($C_1$-$C_6$-alkyl)- itself be a substituent of another substituent or fragment (such as ($C_1$-$C_6$-alkyl)HN—($C_1$-$C_6$-alkyl)-O—), meaning that a substituent or fragment (such as —O—) in turn is substituted by a substituted alkyl radical (such as ($C_1$-$C_6$-alkyl)HN—($C_1$-$C_6$-alkyl)-). For the definitions and possible substitutions of alkyl, heteroaryl, heterocyclyl and aryl it is referred to the above-mentioned definitions.

Halogen is fluorine, chlorine, bromine or iodine, preferably fluorine, chlorine or bromine, most preferably fluorine or chlorine.

The present invention includes all stereoisomeric forms of the compounds of the formula (I). Asymmetrical carbon atoms that are present in the compounds of formula (I) all independently of one another have S configuration or R configuration. The invention includes all possible enantiomers and diastereomers and mixtures of two or more stereoisomers, for example mixtures of enantiomers and/or diastereomers, in all amounts and ratios. Thus, compounds according to the present invention which may exist as enantiomers may be present in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. All these forms are an object of the present invention. The preparation of individual stereoisomers may be carried out, if desired, by separation of a mixture by customary methods, for example by chromatography or crystallization, by the use of stereochemically uniform starting materials for the synthesis or by stereoselective synthesis. Optionally, a derivatization may be carried out before a separation of stereoisomers. The separation of a mixture of stereoisomers may be carried out at the stage of the compounds of the formula (I) or at the stage of an intermediate during the synthesis. The present invention also includes all tautomeric forms of the compounds of formula (I), in particular keto-enol tautomerism, i.e. the respective compounds may be present either in their keto form or in their enol form or in mixtures thereof in all ratios.

Where the compounds according to formula (I) contain one or more acidic or basic groups, the invention also comprises their corresponding physiologically or toxicologically acceptable salts.

Physiologically acceptable salts are particularly suitable for medical applications, due to their greater solubility in water compared with the starting or base compounds. Said salts must have a physiologically acceptable anion or cation. Suitable physiologically acceptable acid addition salts of the compounds of the invention are salts of inorganic acids such as hydrochloric acid, hydrobromic acid, phosphoric acid, metaphosphoric acid, nitric acid, sulfonic acid and sulfuric acid and also of organic acids such as, for example, acetic acid, theophyllineacetic acid, methylene-bis-b-oxynaphthoic acid, benzenesulfonic acid, benzoic acid, citric acid, ethanesulfonic acid, salicylic acid, fumaric acid, gluconic acid, glycolic acid, isethionic acid, lactic acid, lactobionic acid, maleic acid, malic acid, methane-sulfonic acid, succinic acid, p-toluenesulfonic acid, tartaric acid and trifluoroacetic acid. Suitable pharmaceutically acceptable basic salts are ammonium salts, alkali metal salts (such as sodium salts and potassium salts) and alkaline earth metal salts (such as magnesium salts and calcium salts).

Salts having a pharmaceutically unacceptable anion are likewise included within the scope of the present invention as useful intermediates for preparing or purifying pharmaceutically acceptable salts and/or for use in nontherapeutic applications, for example in-vitro applications.

If the compounds of the formula (I) simultaneously contain acidic and basic groups in the same molecule, the invention also includes, in addition to the salt forms mentioned, inner salts or betaines (zwitterions).

The respective salts of the compounds according to the formula (I) may be obtained by customary methods which are known to the person skilled in the art like, for example by reacting these with an organic or inorganic acid or base in a solvent or dispersant, or by anion exchange or cation exchange with other salts.

The present invention furthermore includes all solvates of compounds of the formula (I), for example hydrates or adducts with alcohols, active metabolites of the compounds of the formula (I), and also derivatives, which contain physiologically tolerable and cleavable groups, for example esters or amides.

The term "physiologically functional derivative" used herein relates to any physiologically acceptable derivative of an inventive compound of the formula I, for example an ester which on administration to a mammal, for example humans, is capable of forming (directly or indirectly) a compound of the formula I or an active metabolite thereof.

The physiologically functional derivatives also include prodrugs of the compounds of the invention. Such prodrugs may be metabolized in vivo to a compound of the invention. These prodrugs may or may not be active themselves and are also object of the present invention.

The compounds of the invention may also be present in various polymorphous forms, for example as amorphous and crystalline polymorphous forms. All polymorphous forms of the compounds of the invention are included within the scope of the invention and are another aspect of the invention.

Preferred compounds of the general formula (I) are the compounds in which one, more than one or all of the substituents $R^1$ to $R^8$, A, B, D, E, heteroaryl, heterocyclyl and aryl detailed above have independently of one another the meanings (definitions) detailed below, and the present invention relates to all possible combinations of preferred, more preferred, even more preferred, particularly preferred and very particularly preferred meanings (definitions), likewise in combination with the substituents in their basic meaning.

A is preferably $CR^3$;
B is preferably $CR^4$;
D is preferably $CR^5$;
E is preferably $CR^6$;

If not every one of the substituents A, B, D and E has its preferred meaning, preferably only two of the substituents A, B, D and E are equal to N; more preferably only one of the substituents A, B, D and E is equal to N; even more preferably, only the substituent B is equal to N.

$R^1$ is preferably:
  fluorine; chlorine; bromine;
  unsubstituted or at least monosubstituted $C_1$-$C_6$-alkyl,
    where the substituents are selected from the group consisting of: halogen, —$OR^7$, —$C(O)R^7$, —$C(O)OR^7$, —$NR^7H$, —$NR^7(C_1$-$C_6$-alkyl-), —$C(O)NR^7H$, —$SR^7$, aryl, heteroaryl, heterocyclyl, tri-fluoromethyl and tri-fluoromethoxy,
    and heterocyclyl, aryl and heteroaryl may in turn be at least monosubstituted by $C_1$-$C_6$-alkyl, $C_1$-$C_6$-alkoxy, halogen, tri-fluoromethyl, tri-fluoromethoxy or OH;
  or unsubstituted or at least monosubstituted hetercyclyl, aryl or heteroaryl,
    where the substituents are selected from the group consisting of: halogen, —$CH_2$—$R^7$, —$CH_2$—$NH_2$, —$CH_2$—$NH(C_1$-$C_6$-alkyl), —$CH_2$—$N(C_1$-$C_6$-alkyl)$_2$, —$CH_2$—OH, —$CH_2$—O—($C_1$-$C_6$-alkyl), —$OR^7$, —$C(O)R^7$, —$C(O)OR^7$, —$NR^7H$, —$NR^7(C_1$-$C_6$-alkyl-), —$C(O)NR^7H$, —$SR^7$, aryl, heteroaryl, tri-fluoromethyl and tri-fluoromethoxy,
    and aryl and heteroaryl may in turn be at least monosubstituted by $C_1$-$C_6$-alkyl, $C_1$-$C_6$-alkoxy, halogen, tri-fluoromethyl, tri-fluoromethoxy or OH;

$R^1$ is more preferably:
  chlorine;
  unsubstituted or at least monosubstituted or heterocyclyl, $C_1$-$C_6$-alkyl,
    where the substituents are selected from the group consisting of: fluorine, chlorine, —OH, $C_1$-$C_6$-alkoxy, —$NH_2$, —$NH(C_1$-$C_6$-alkyl), —$N(C_1$-$C_6$-alkyl)$_2$, heterocyclyl-($C_1$-$C_6$-alkyl)-NH—, aryl-($C_1$-$C_6$-alkyl)-NH—, heterocyclyl, aryl and heteroaryl, and the heterocyclyl, aryl and heteroaryl fragments of these substituents may in turn be at least monosubstituted by $C_1$-$C_4$-alkyl, $C_1$-$C_4$-alkoxy, fluorine, chlorine, tri-fluoromethyl, tri-fluoromethoxy or OH;

or unsubstituted or at least monosubstituted phenyl, pyridinyl, pyrimidinyl, pyrazolyl, thiophenyl, oxazolyl, isoxazolyl, thiazolyl, imidazolyl, morpholinyl, dihydropyridinonyl, benzo[b]thiophenyl, 1,3-benzodioxolyl or thiazolo[3,2-b][1,2,4]-triazolyl, where the substituents are selected from the group consisting of: halogen, —$CH_2$—$R^7$, —$CH_2$—$NH_2$, —$CH_2$—$NH(C_1$-$C_6$-alkyl), —$CH_2$—$N(C_1$-$C_6$-alkyl)$_2$, —$CH_2$—OH, —$CH_2$—O—($C_1$-$C_6$-alkyl), —$OR^7$, —$C(O)R^7$, —$C(O)OR^7$, —$NR^7H$, —$NR^7$($C_1$-$C_6$-alkyl-), —$C(O)NR^7H$, —$SR^7$, aryl, heteroaryl, tri-fluoromethyl and tri-fluoromethoxy, and aryl and heteroaryl may in turn be at least monosubstituted by $C_1$-$C_6$-alkyl, $C_1$-$C_6$-alkoxy, halogen, tri-fluoromethyl, tri-fluoromethoxy or OH;

$R^1$ is even more preferably:

unsubstituted or at least monosubstituted phenyl, pyridinyl, pyrimidinyl, pyrazolyl, thiophenyl, oxazolyl, isoxazolyl, thiazolyl, imidazolyl, morpholinyl, dihydropyridinonyl, benzo[b]thiophenyl, benzodioxolyl or thiazolo[3,2-b][1,2,4]-triazolyl, where the substituents are selected from the group consisting of: halogen, —$CH_2$—$R^7$, —$CH_2$—$NH_2$, —$CH_2$—$NH(C_1$-$C_6$-alkyl), —$CH_2$—$N(C_1$-$C_6$-alkyl)$_2$, —$CH_2$—OH, —$CH_2$—O—($C_1$-$C_6$-alkyl), —$OR^7$, —$C(O)R^7$, —$C(O)OR^7$, —$NR^7H$, —$NR^7$($C_1$-$C_6$-alkyl-), —$C(O)NR^7H$, —$SR^7$, aryl, heteroaryl, tri-fluoromethyl and tri-fluoromethoxy, and aryl and heteroaryl may in turn be at least monosubstituted by $C_1$-$C_6$-alkyl, $C_1$-$C_6$-alkoxy, halogen, tri-fluoromethyl, tri-fluoromethoxy or OH;

$R^1$ is much more preferably:

unsubstituted or at least monosubstituted phenyl, pyridinyl, pyrimidinyl, pyrazolyl, thiophenyl, oxazolyl, isoxazolyl, thiazolyl, imidazolyl, morpholinyl, dihydropyridinonyl, benzo[b]thiophenyl, benzodioxolyl or thiazolo[3,2-b][1,2,4]-triazolyl, where the substituents are selected from the group consisting of: halogen, $C_1$-$C_6$-alkyl, phenyl-($C_1$-$C_6$-alkyl)-, —OH, $C_1$-$C_6$-alkoxy, ($C_1$-$C_6$-alkyl)thio-, —O—phenyl, —$NH_2$, —$N(C_1$-$C_6$-alkyl)$_2$, —NH($C_1$-$C_6$-alkyl), HO(O)C—($C_1$-$C_6$-alkyl) NH—, ($C_1$-$C_6$-alkyl)-O(O)C—($C_1$-$C_6$-alkyl)-NH—, $H_2N(O)$C—($C_1$-$C_6$-alkyl)-NH—, ($C_1$-$C_6$-alkyl)HN(O)C—($C_1$-$C_6$-alkyl)-NH—, $H_2N$—($C_1$-$C_6$-alkyl)-, ($C_1$-$C_6$-alkyl)HN—($C_1$-$C_6$-alkyl)-, ($C_1$-$C_6$-alkyl)$_2$N—($C_1$-$C_6$-alkyl)-, heterocyclyl-($C_1$-$C_6$-alkyl)-O—, $H_2N$—($C_1$-$C_6$-alkyl)-NH—, ($C_1$-$C_6$-alkyl)HN—($C_1$-$C_6$-alkyl)-NH—, ($C_1$-$C_6$-alkyl)$_2$N—($C_1$-$C_6$-alkyl)-NH—, heterocyclyl-($C_1$-$C_6$-alkyl)-NH—, heteroaryl-($C_1$-$C_6$-alkyl)-NH—, phenyl-($C_1$-$C_6$-alkyl)-NH—, ($C_1$-$C_6$-alkyl)-O-($C_1$-$C_6$-alkyl)-NH—, HO—($C_1$-$C_6$-alkyl)-NH—, heterocyclyl-($C_1$-$C_6$-alkyl)-, tri-fluoromethyl, tri-fluoromethoxy, phenyl and heteroaryl, and the heterocyclyl, phenyl and heteroaryl fragments of these substituents may in turn be at least monosubstituted by $C_1$-$C_3$-alkyl, $C_1$-$C_3$-alkoxy, fluorine, chlorine, tri-fluoromethyl, tri-fluoromethoxy or OH;

$R^1$ is particularly preferably:

unsubstituted or at least monosubstituted phenyl, thiophenyl, pyridinyl or pyrimidinyl, where the substituents are selected from the group consisting of: $C_1$-$C_4$-alkyl, —$CH_2$—$NH(C_1$-$C_4$-alkyl), OH, $C_1$-$C_4$-alkoxy, ($C_1$-$C_4$-alkyl)thio-, tri-fluoromethyl, tri-fluoromethoxy and —$NH(C_1$-$C_4$-alkyl), and —$NH(C_1$-$C_4$-alkyl) may in turn be monosubstituted by phenyl, piperazinyl, piperidinyl or morpholinyl.

$R^1$ is very particularly preferably:

pyridin-4-yl, 4-hydroxy-3-methoxy-5-(methylaminomethyl)phenyl, 2-ethyl-aminopyrimidin-4-yl, 3,5-dimethyl-4-hydroxyphenyl, 2-(1-phenylethylamino)-pyrimidin-4-yl, 2-(2-morpholin-4-ylethylamino)pyrimidin-4-yl, 2-methylamino-pyrimidin-4-yl, 6-methyl-2-(2-morpholin-4-ylethylamino)pyrimidin-4-yl, 3-methoxy-4-hydroxyphenyl, 2-methylsulfanylpyrimidin-4-yl or 4-butylamino-pyrimidin-4-yl.

$R^2$ is preferably hydrogen or $C_1$-$C_6$-alkyl; $R^2$ is particularly preferably hydrogen.

$R^3$ is preferably selected from the group consisting of: hydrogen, halogen, —CN, —$CH_2$—$R^8$, —$CH_2$—$NH_2$, —$CH_2$—$NH(C_1$-$C_6$-alkyl), —$CH_2$—$N(C_1$-$C_6$-alkyl)$_2$, —$CH_2$—OH, —$CH_2$—O—($C_1$-$C_6$-alkyl), —$OR^8$, —$C(O)R^8$, —$C(O)OR^8$, —$NR^8H$, —$NR^8$($C_1$-$C_6$-alkyl-), —$C(O)NR^8H$, —$SR^8$, —$SO_2NR^8H$, —$SO_2R^8$, aryl, heteroaryl, heterocyclyl, tri-fluoromethyl and tri-fluoromethoxy, and heterocyclyl, aryl and heteroaryl may in turn be at least monosubstituted by $C_1$-$C_6$-alkyl, $C_1$-$C_6$-alkoxy, oxo, halogen, tri-fluoromethyl, tri-fluoromethoxy or OH;

$R^3$ is more preferably selected from the group consisting of:

hydrogen, fluorine, chlorine, bromine, —CN, —$CH_2$—$R^8$, —$CH_2$—$NH_2$, —$CH_2$—$NH(C_1$-$C_6$-alkyl), —$CH_2$—$N(C_1$-$C_6$-alkyl)$_2$, —$CH_2$—OH, —$CH_2$—O—($C_1$-$C_6$-alkyl), —$OR^8$, —$C(O)R^8$, —$C(O)OR^8$, —$NR^8H$, —$NR^8$($C_1$-$C_6$-alkyl-), —$C(O)NR^8H$, —$SR^8$, —$SO_2NR^8H$, —$SO_2$—$R^8$, heterocyclyl, tri-fluoromethyl and tri-fluoromethoxy, and heterocyclyl may in turn be at least monosubstituted by $C_1$-$C_6$-alkyl, $C_1$-$C_6$-alkoxy, halogen, tri-fluoromethyl, tri-fluoromethoxy or OH;

$R^3$ is much more preferably selected from the group consisting of:

hydrogen, fluorine, chlorine, bromine, —CN, $C_1$-$C_6$-alkyl, phenyl-($C_1$-$C_6$-alkyl)-, —OH, $C_1$-$C_6$-alkoxy, —O-phenyl, —C(O)OH, —C(O)O—($C_1$-$C_6$-alkyl), —$NR^8H$, —$NR^8$($C_1$-$C_6$-alkyl-), —$C(O)NR^8H$, heterocyclyl, tri-fluoromethyl and tri-fluoromethoxy, and the heterocyclyl and phenyl fragments of this group may in turn be at least monosubstituted by $C_1$-$C_6$-alkyl, $C_1$-$C_6$-alkoxy, halogen, tri-fluoromethoxy, tri-fluoromethoxy or OH;

$R^3$ is even much more preferably selected from the group consisting of:

hydrogen, fluorine, chlorine, bromine, —CN, $C_1$-$C_6$-alkyl, —OH, $C_1$-$C_6$-alkoxy, —C(O)OH, —C(O)O—($C_1$-$C_6$-alkyl), —$NH_2$, —$N(C_1$-$C_6$-alkyl)$_2$, —NH($C_1$-$C_6$-alkyl), $H_2N$—($C_1$-$C_6$-alkyl)-NH—, hydroxy-($C_1$-$C_6$-alkyl)-NH—, ($C_1$-$C_6$-alkyl)HN—($C_1$-$C_6$-alkyl)-NH—, ($C_1$-$C_6$-alkyl)$_2$N—($C_1$-$C_6$-alkyl)-NH—, heterocyclyl-($C_1$-$C_6$-alkyl)-NH, heteroaryl-($C_1$-$C_6$-alkyl)-NH—, phenyl-($C_1$-$C_6$-alkyl)-NH—, —C(O)$NH_2$, —C(O)N($C_1$-$C_6$-alkyl)$_2$, —C(O)NH($C_1$-$C_6$-alkyl), $H_2N$—($C_1$-$C_6$-alkyl)-NHC(O)—, hydroxy-($C_1$-$C_6$-alkyl)-NHC(O)—, ($C_1$-$C_6$-alkyl)HN—($C_1$-$C_6$- alkyl)-NHC(O)—, $(C_1$-$C_6$-alkyl)$_2$N—$(C_1$-$C_6$-alkyl)-NHC(O)—, heterocyclyl-$(C_1$-$C_6$-alkyl)-NHC(O)—, heteroaryl-$(C_1$-$C_6$-alkyl)-NHC(O)—, phenyl-$(C_1$-$C_6$-alkyl)-N HC(O)—, heterocyclyl, heterocyclyl-$(C_1$-$C_6$-alkyl)-, tri-fluoromethyl and tri-fluoromethoxy, and the heteroaryl, heterocyclyl and phenyl fragments of this group may in turn be at least monosubstituted by $C_1$-$C_6$-alkyl, $C_1$-$C_6$-alkoxy, halogen, tri-fluoromethoxy, tri-fluoromethoxy or OH;

$R^3$ is particularly preferably selected from the group consisting of:

hydrogen, fluorine, chlorine, bromine, —CN, —C(O)O-methyl, (2-diethylaminoethyl)-NHC(O)—, COOH, methoxy, ethoxy, (2-cyclohexylaminoethyl)-NHC(O)—, (3-(4-methylpiperazin-1-yl)propyl) -NHC(O)—, (3-hydroxypropyl)-NHC(O)—, (3-cyclohexylaminopropyl)-NHC(O)—, (3-imidazol-1-ylpropyl)-NHC(O)—, methyl, ethyl, 4-methylpiperazin-1-yl, tri-fluoromethoxy and tri-fluoromethoxy;

$R^3$ is very particularly preferably selected from the group consisting of:

hydrogen, fluorine, chlorine, bromine, methyl and ethyl;

$R^4$ is preferably selected from the group consisting of:

hydrogen, halogen, —CN, —CH$_2$—R$^8$, —CH$_2$—NH$_2$, —CH$_2$—NH(C$_1$-C$_6$-alkyl), —CH$_2$—N(C$_1$-C$_6$-alkyl)$_2$, —CH$_2$—OH, —CH$_2$—O—(C$_1$-C$_6$-alkyl), —OR$^8$, —C(O)R$^8$, —C(O)OR$^8$, —NR$^8$H, —NR$^8$(C$_1$-C$_6$-alkyl), —C(O)NR$^8$H, —SR$^8$, —SO$_2$NR$^8$H, —SO$_2$—R$^8$, aryl, heteroaryl, heterocyclyl, tri-fluoromethyl and tri-fluoromethoxy, and heterocyclyl, aryl and heteroaryl may in turn be at least monosubstituted by $C_1$-$C_6$-alkyl, $C_1$-$C_6$-alkoxy, oxo, halogen, tri-fluoromethyl, tri-fluoromethoxy or OH;

$R^4$ is more preferably selected from the group consisting of:

hydrogen, fluorine, chlorine, bromine, —CN, —SO$_2$NR$^8$H, —SO$_2$—R$^8$, —CH$_2$—R$^8$, —CH$_2$—NH$_2$, —CH$_2$—NH(C$_1$-C$_6$-alkyl), —CH$_2$—N(C$_1$-C$_6$-alkyl)$_2$, —CH$_2$—OH, —CH$_2$—O—(C$_1$-C$_6$-alkyl), —OR$^8$, —C(O)R$^8$, —C(O)OR$^8$, —NR$^8$H, —NR$^8$(C$_1$-C$_6$-alkyl), —C(O)NR$^8$H, —SR$^8$, heterocyclyl, tri-fluoromethyl and tri-fluoromethoxy, and heterocyclyl may in turn be at least monosubstituted by $C_1$-$C_6$-alkyl, $C_1$-$C_6$-alkoxy, halogen, tri-fluoromethyl, tri-fluoromethoxy or OH;

$R^4$ is much more preferably selected from the group consisting of:

hydrogen, fluorine, chlorine, bromine, —CN, $C_1$-$C_6$-alkyl, phenyl-$(C_1$-$C_6$-alkyl)-, —OH, $C_1$-$C_6$-alkoxy, —O-phenyl, —C(O)OH, —C(O)O—(C$_1$-C$_6$-alkyl), —NR$^8$H, —NR$^8$(C$_1$-C$_6$-alkyl-), —C(O)NR$^8$H, heterocyclyl, tri-fluoromethyl and tri-fluoromethoxy, and the heterocyclyl and phenyl fragments of this group may in turn be at least monosubstituted by $C_1$-$C_6$-alkyl, $C_1$-$C_6$-alkoxy, halogen, tri-fluoromethyl, tri-fluoromethoxy or OH;

$R^4$ is even much more preferably selected from the group consisting of:

hydrogen, fluorine, chlorine, bromine, —CN, $C_1$-$C_6$-alkyl, —OH, $C_1$-$C_6$-alkoxy, —C(O)OH, —C(O)O—(C$_1$-C$_6$-alkyl), —NH$_2$, —N(C$_1$-C$_6$-alkyl)$_2$, —NH(C$_1$-C$_6$-alkyl), H$_2$N—(C$_1$-C$_6$-alkyl)-NH—, hydroxy-(C$_1$-C$_6$-alkyl)-NH—, (C$_1$-C$_6$-alkyl)HN—(C$_1$-C$_6$-alkyl)-NH—, (C$_1$-C$_6$-alkyl)$_2$N—(C$_1$-C$_6$-alkyl)-NH—, heterocyclyl-(C$_1$-C$_6$-alkyl)-NH—, heteroaryl-$(C_1$-$C_6$-alkyl)-NH—, phenyl-$(C_1$-$C_6$-alkyl)-NH—, —C(O)NH$_2$, —C(O)N(C$_1$-C$_6$-alkyl)$_2$, —C(O)NH (C$_1$-C$_6$-alkyl), H$_2$N—(C$_1$-C$_6$-alkyl) -NHC(O)—, hydroxy-(C$_1$-C$_6$-alkyl)-NHC(O)—, (C$_1$-C$_6$-alkyl)HN—(C$_1$-C$_6$-alkyl) -NHC(O)—, (C$_1$-C$_6$-alkyl)$_2$N—(C$_1$-C$_6$-alkyl)-NHC(O)—, heterocyclyl-(C$_1$-C$_6$-alkyl) -NHC(O)—, heteroaryl-$(C_1$-$C_6$-alkyl)-NHC(O)—, phenyl-$(C_1$-$C_6$-alkyl)-NHC(O)—, heterocyclyl, heterocyclyl-$(C_1$-$C_6$-alkyl)-, tri-fluoromethyl and tri-fluoromethoxy, and the heteroaryl, heterocyclyl and phenyl fragments of this group may in turn be at least monosubstituted by $C_1$-$C_6$-alkyl, $C_1$-$C_6$-alkoxy, halogen, tri-fluoromethyl, tri-fluoromethoxy or OH;

$R^4$ is particularly preferably selected from the group consisting of:

hydrogen, fluorine, chlorine, bromine, —CN, —C(O)O-methyl, (2-diethylaminoethyl)-NHC(O)—, COOH, methoxy, ethoxy, (2-cyclohexylaminoethyl)-NHC(O)—, (3-(4-methylpiperazin-1-yl)propyl) -NHC(O)—, (3-hydroxypropyl)-NHC(O)—, (3-cyclohexylaminopropyl)-NHC(O)—, (3-imidazol-1-ylpropyl)-NHC(O)—, methyl, ethyl, 4-methylpiperazin-1-yl, tri-fluoromethyl and tri-fluoromethoxy;

$R^5$ is preferably selected from the group consisting of:

hydrogen, halogen, —CN, —CH$_2$—R$^8$, —CH$_2$—NH$_2$, —CH$_2$—NH(C$_1$-C$_6$-alkyl), —CH$_2$—N(C$_1$-C$_6$-alkyl)$_2$, —CH$_2$—OH, —CH$_2$—O—(C$_1$-C$_6$-alkyl), —OR$^8$, —C(O)R$^8$, —C(O)OR$^8$, —NR$^8$H, —NR$^8$(C$_1$-C$_6$-alkyl), —C(O)NR$^8$H, —SR$^8$, —SO$_2$NR$^8$H, —SO$_2$—R$^8$, aryl, heteroaryl, heterocyclyl, tri-fluoromethyl and tri-fluoromethoxy, and heterocyclyl, aryl and heteroaryl may in turn be at least monosubstituted by $C_1$-$C_6$-alkyl, $C_1$-$C_6$-alkoxy, oxo, halogen, tri-fluoromethyl, tri-fluoromethoxy or OH;

$R^5$ is more preferably selected from the group consisting of:

hydrogen, fluorine, chlorine, bromine, —CN, —CH$_2$—R$^8$, —CH$_2$—NH$_2$, —CH$_2$—NH(C$_1$-C$_6$-alkyl), —CH$_2$—N(C$_1$-C$_6$-alkyl)$_2$, —CH$_2$—OH, —CH$_2$—O—(C$_1$-C$_6$-alkyl), —OR$^8$, —C(O)R$^8$, —C(O)OR$^8$, —NR$^8$H, —NR$^8$(C$_1$-C$_6$-alkyl), —C(O)NR$^8$H, —SR$^8$, —SO$_2$NR$^8$H, —SO$_2$—R$^8$, heterocyclyl, tri-fluoromethyl and tri-fluoromethoxy, and heterocyclyl may in turn be at least monosubstituted by $C_1$-$C_6$-alkyl, $C_1$-$C_6$-alkoxy, halogen, tri-fluoromethyl, tri-fluoromethoxy or OH;

$R^5$ is much more preferably selected from the group consisting of:

hydrogen, fluorine, chlorine, bromine, —CN, $C_1$-$C_6$-alkyl, phenyl-$(C_1$-$C_6$-alkyl)-, —OH, $C_1$-$C_6$-alkoxy, —O-phenyl, —C(O)OH, —C(O)O—(C$_1$-C$_6$-alkyl), —NR$^8$H, —NR$^8$(C$_1$-C$_6$-alkyl), —C(O)NR$^8$H, heterocyclyl, tri-fluoromethyl and tri-fluoromethoxy, and the heterocyclyl and phenyl fragments of this group may in turn be at least monosubstituted by $C_1$-$C_6$-alkyl, $C_1$-$C_6$-alkoxy, halogen, tri-fluoromethyl, tri-fluoromethoxy or OH;

$R^5$ is even much more preferably selected from the group consisting of:

hydrogen, fluorine, chlorine, bromine, —CN, $C_1$-$C_6$-alkyl, —OH, $C_1$-$C_6$-alkoxy, —C(O)OH, —C(O)O—(C$_1$-C$_6$-alkyl), —NH$_2$, —N(C$_1$-C$_6$-alkyl)$_2$, —NH(C$_1$-C$_6$-alkyl), H$_2$N—(C$_1$-C$_6$-alkyl)-NH—, hydroxy-(C$_1$-C$_6$-alkyl)-NH—, (C$_1$-C$_6$-alkyl)HN—(C$_1$-C$_6$- alkyl)-NH—, ($C_1$-$C_6$-alkyl)$_2$N—($C_1$-$C_6$-alkyl)-NH—, heterocyclyl-($C_1$-$C_6$-alkyl), NH-heteroaryl-($C_1$-$C_6$-alkyl)-NH—, phenyl-($C_1$-$C_6$-alkyl)-NH—, —C(O)NH$_2$, —C(O)N($C_1$-$C_6$-alkyl)$_2$, —C(O)NH($C_1$-$C_6$-alkyl), H$_2$N—($C_1$-$C_6$-alkyl)-NHC(O)—, hydroxy-($C_1$-$C_6$-alkyl)-NHC(O)—, ($C_1$-$C_6$-alkyl)HN—($C_1$-$C_6$-alkyl)-NHC(O)—, ($C_1$-$C_6$-alkyl)$_2$N—($C_1$-$C_6$-alkyl)-NHC(O)—, heterocyclyl-($C_1$-$C_6$-alkyl)-NHC(O)—, heteroaryl-($C_1$-$C_6$-alkyl)-NHC(O)—, phenyl-($C_1$-$C_6$-alkyl)-NHC(O)—, heterocyclyl, heterocyclyl-($C_1$-$C_6$-alkyl)-, tri-fluoromethyl and tri-fluoromethoxy, and the heteroaryl, heterocyclyl and phenyl fragments of this group may in turn be at least monosubstituted by $C_1$-$C_6$-alkyl, $C_1$-$C_6$-alkoxy, halogen, tri-fluoromethyl, tri-fluoromethoxy or OH;

$R^5$ is particularly preferably selected from the group consisting of:

hydrogen, fluorine, chlorine, bromine, —CN, —C(O)O-methyl, (2-diethylaminoethyl)-NHC(O)—, COOH, methoxy, ethoxy, (2-cyclohexylaminoethyl)-NHC(O)—, (3-(4-methylpiperazin-1-yl)propyl)-NHC(O)—, (3-hydroxypropyl)-NHC(O)—, (3-cyclohexylaminopropyl)-NHC(O)—, (3-imidazol-1-ylpropyl)-NHC(O)—, methyl, ethyl, 4-methylpiperazin-1-yl, tri-fluoromethyl and tri-fluoromethoxy;

$R^6$ is preferably selected from the group consisting of:

hydrogen, halogen, —CN, —CH$_2$—$R^8$, —CH$_2$—NH$_2$, —CH$_2$—NH($C_1$-$C_6$-alkyl), —CH$_2$—N($C_1$-$C_6$-alkyl)$_2$, —CH$_2$—OH, —CH$_2$—O—($C_1$-$C_6$-alkyl), —OR$^8$, —C(O)R$^8$, —C(O)OR$^8$, —NR$^8$H, —NR$^8$($C_1$-$C_6$-alkyl), —C(O)NR$^8$H, —SR$^8$, —SO$_2$NR$^8$H, —SO$_2$—R$^8$, aryl, heteroaryl, heterocyclyl, tri-fluoromethyl and tri-fluoromethoxy, and heterocyclyl, aryl and heteroaryl may in turn be at least monosubstituted by $C_1$-$C_6$-alkyl, $C_1$-$C_6$-alkoxy, oxo, halogen, tri-fluoromethyl, tri-fluoromethoxy or OH;

$R^6$ is more preferably selected from the group consisting of:

hydrogen, fluorine, chlorine, bromine, —CN, —CH$_2$—R$^8$, —CH$_2$—NH$_2$, —CH$_2$—NH($C_1$-$C_6$-alkyl), —CH$_2$—N($C_1$-$C_6$-alkyl)$_2$, —CH$_2$—OH, —CH$_2$—O—($C_1$-$C_6$-alkyl), —OR$^8$, —C(O)R$^8$, —C(O)OR$^8$, —NR$^8$H, —NR$^8$($C_1$-$C_6$-alkyl), —C(O)NR$^8$H, —SR$^8$, —SO$_2$NR$^8$H, —SO$_2$—R$^8$, heterocyclyl, tri-fluoromethyl and tri-fluoromethoxy, and heterocyclyl may in turn be at least monosubstituted by $C_1$-$C_6$-alkyl, $C_1$-$C_6$-alkoxy, halogen, tri-fluoromethyl, tri-fluoromethoxy or OH;

$R^6$ is much more preferably selected from the group consisting of:

hydrogen, fluorine, chlorine, bromine, —CN, $C_1$-$C_6$-alkyl, phenyl-($C_1$-$C_6$-alkyl)-, —OH, $C_1$-$C_6$-alkoxy, —O-phenyl, —C(O)OH, —C(O)O—($C_1$-$C_6$-alkyl), —NR$^8$H, —NR$^8$($C_1$-$C_6$-alkyl-), —C(O)NR$^8$H, heterocyclyl, tri-fluoromethyl and tri-fluoromethoxy, and the heterocyclyl and phenyl fragments of this group may in turn be at least monosubstituted by $C_1$-$C_6$-alkyl, $C_1$-$C_6$-alkoxy, halogen, tri-fluoromethyl, tri-fluoromethoxy or OH;

$R^6$ is even more preferably selected from the group consisting of:

hydrogen, fluorine, chlorine, bromine, —CN, $C_1$-$C_6$-alkyl, —OH, $C_1$-$C_6$-alkoxy, —C(O)OH, —C(O)O—($C_1$-$C_6$-alkyl), —NH$_2$, —N($C_1$-$C_6$-alkyl)$_2$, —NH($C_1$-$C_6$-alkyl), H$_2$N—($C_1$-$C_6$-alkyl)-NH—, hydroxy-($C_1$-$C_6$-alkyl)-NH—, ($C_1$-$C_6$-alkyl)HN-($C_1$-$C_6$-alkyl)-NH—, ($C_1$-$C_6$-alkyl)$_2$N—($C_1$-$C_6$-alkyl)-NH—, heterocyclyl-($C_1$-$C_6$-alkyl)-NH, heteroaryl-($C_1$-$C_6$-alkyl)-NH—, phenyl-($C_1$-$C_6$-alkyl)-NH—, —C(O)NH$_2$, —C(O)N(($C_1$-$C_6$-alkyl)$_2$, —C(O)NH($C_1$-$C_6$-alkyl), H$_2$N—($C_1$-$C_6$-alkyl)-NHC(O)—, hydroxy-($C_1$-$C_6$-alkyl)-NHC(O)—, ($C_1$-$C_6$-alkyl)HN—($C_1$-$C_6$-alkyl)-NHC(O)—, ($C_1$-$C_6$-alkyl)$_2$N-($C_1$-$C_6$-alkyl)-NHC(O)—, heterocyclyl-($C_1$-$C_6$-alkyl)-NHC(O)—, heteroaryl-($C_1$-$C_6$-alkyl)-NHC(O)—, phenyl-($C_1$-$C_6$-alkyl)-NHC(O)—, heterocyclyl, heterocyclyl-($C_1$-$C_6$-alkyl)-, tri-fluoromethyl and tri-fluoromethoxy, and the heteroaryl, heterocyclyl and phenyl fragments of this group may in turn be at least monosubstituted by $C_1$-$C_6$-alkyl, $C_1$-$C_6$-alkoxy, halogen, tri-fluoromethyl, tri-fluoromethoxy or OH;

$R^6$ is particularly preferably selected from the group consisting of:

hydrogen, fluorine, chlorine, bromine, —CN, —C(O)O-methyl, (2-diethylaminoethyl)-NHC(O)—, COOH, methoxy, ethoxy, (2-cyclohexylaminoethyl)-NHC(O)—, (3-(4-methylpiperazin-1-yl)propyl) -NHC(O)—, (3-hydroxypropyl)-NHC(O)—, (3-cyclohexylaminopropyl)-NHC(O)—, (3-imidazol-1-ylpropyl)-NHC(O)—, methyl, ethyl, 4-methylpiperazin-1-yl, tri-fluoromethyl and tri-fluoromethoxy;

$R^6$ is very particularly preferably hydrogen;

$R^7$ is preferably:

H;

unsubstituted or at least monosubstituted $C_1$-$C_6$-alkyl, heterocyclyl, phenyl or heteroaryl, where the substituents are selected from the group consisting of: heteroaryl, heterocyclyl, phenyl, fluorine, chlorine, bromine, —OH, $C_1$-$C_6$-alkoxy, —C(O)OH, —C(O)O—($C_1$-$C_6$-alkyl), —C(O) NH$_2$, —C(O)NH($C_1$-$C_6$-alkyl), —C(O)N($C_1$-$C_{10}$-alkyl)$_2$, tri-fluoromethyl, tri-fluoromethoxy, —NH$_2$, —NH($C_1$-$C_6$-alkyl) and —N($C_1$-$C_6$-alkyl)$_2$, and heterocyclyl, phenyl and heteroaryl may in turn be at least monosubstituted by $C_1$-$C_3$-alkyl, $C_1$-$C_3$-alkoxy, oxo, tri-fluoromethyl, tri-fluoromethoxy, fluorine, chlorine or OH;

$R^7$ is more preferably:

unsubstituted or at least monosubstituted $C_1$-$C_6$-alkyl, where the substituents are selected from the group consisting of: heteroaryl, heterocyclyl, —OH, —C(O)OH, —C(O)O—($C_1$-$C_6$-alkyl), —C(O)NH$_2$, —C(O)NH($C_1$-$C_6$-alkyl), —C(O)N($C_1$-$C_{10}$-alkyl)$_2$, —NH$_2$, —NH($C_1$-$C_6$-alkyl) and —N($C_1$-$C_6$-alkyl)$_2$.

and heterocyclyl, and heteroaryl may in turn be at least monosubstituted by $C_1$-$C_3$-alkyl, $C_1$-$C_3$-alkoxy, tri-fluoromethyl, tri-fluoromethoxy, fluorine, chlorine or OH;

$R^7$ is particularly preferably:

unsubstituted or at least monosubstituted $C_1$-$C_4$-alkyl, where the substituents are selected from the group consisting of: morpholinyl, piperazinyl, piperidinyl, imidazolyl, —NH$_2$, —NH($C_1$-$C_6$-alkyl) and —N($C_1$-$C_6$-alkyl)$_2$, and morpholinyl, piperazinyl, piperidinyl and imidazolyl may in turn be monosubstituted by $C_1$-$C_3$-alkyl, $C_1$-$C_3$-alkoxy, tri-fluoromethyl, tri-fluoromethoxy, fluorine, chlorine or OH;

$R^8$ is preferably:
- H;
- unsubstituted or at least monosubstituted $C_1$-$C_6$-alkyl, heterocyclyl, phenyl or heteroaryl,
  where the substituents are selected from the group consisting of: heteroaryl, heterocyclyl, phenyl, fluorine, chlorine, bromine, —OH, $C_1$-$C_6$-alkoxy, —C(O)OH, —C(O)O—($C_1$-$C_6$-alkyl), —C(O)$NH_2$, —C(O)NH($C_1$-$C_6$-alkyl), —C(O)N($C_1$-$C_{10}$-alkyl)$_2$, tri-fluoromethyl, tri-fluoromethoxy, —$NH_2$, —NH($C_1$-$C_6$-alkyl) and —N($C_1$-$C_6$-alkyl)$_2$,
  and heterocyclyl, phenyl and heteroaryl may in turn be at least monosubstituted by $C_1$-$C_3$-alkyl, $C_1$-$C_3$-alkoxy, oxo, tri-fluoromethyl, tri-fluoromethoxy, fluorine, chlorine or OH;

$R^8$ is more preferably:
- unsubstituted or at least monosubstituted $C_1$-$C_6$-alkyl,
  where the substituents are selected from the group consisting of: heteroaryl, heterocyclyl, —OH, —C(O)OH, —C(O)O—($C_1$-$C_6$-alkyl), —C(O)$NH_2$, —C(O)NH($C_1$-$C_6$-alkyl), —C(O)N($C_1$-$C_{10}$-alkyl)$_2$, —$NH_2$, —NH($C_1$-$C_6$-alkyl) and —N($C_1$-$C_6$-alkyl)$_2$,
  and heterocyclyl, and heteroaryl may in turn be at least monosubstituted by $C_1$-$C_3$-alkyl, $C_1$-$C_3$-alkoxy, tri-fluoromethyl, tri-fluoromethoxy, fluorine, chlorine or OH;

$R^8$ is particularly preferably:
- unsubstituted or at least monosubstituted $C_1$-$C_4$-alkyl,
  where the substituents are selected from the group consisting of: morpholinyl, piperazinyl, piperidinyl, imidazolyl, —$NH_2$, —NH($C_1$-$C_6$-alkyl) and —N($C_1$-$C_6$-alkyl)$_2$,
  and morpholinyl, piperazinyl, piperidinyl and imidazolyl may in turn be monosubstituted by $C_1$-$C_3$-alkyl, $C_1$-$C_3$-alkoxy, tri-fluoromethyl, tri-fluoromethoxy, fluorine, chlorine or OH;

Heteroaryl is preferably imidazolyl, thiophenyl, furanyl, thiazolyl, imidazolyl, oxazolyl, isoxazolyl, pyridinyl, pyrimidinyl, pyrazolyl, benzo[b]thiophenyl, thiazolo[3,2-b][1,2,4]-triazolyl, pyrrolyl, quinolinyl, isoquinolinyl, 1,2,3,4-tetrahydroquinolinyl, benzoimidazolyl, indolyl or 1,3-benzodioxolyl; heteroaryl is particularly preferably pyridinyl, thiophenyl or pyrimidinyl;

Aryl is preferably naphthyl, indanyl or phenyl; Aryl is particularly preferably phenyl.

Heterocyclyl is preferably 2-oxo-azepanyl, 1,4-oxazepanyl, dihydropyridinonyl, tetrahydrofuranyl, 1,3-dioxolanyl, morpholinyl, pyrrolidinyl, piperazinyl or piperidinyl; heterocyclyl is particularly preferably piperidinyl, morpholinyl or piperazinyl;

Examples of embodiments with preferred compounds of the general formula (I) with reference to the meanings (definitions) described above are:

i) $R^1$, $R^2$, $R^3$, $R^4$, $R^5$, $R^6$, $R^7$, $R^8$, A, B, D, E, heteroaryl, heterocyclyl and aryl have their preferred meaning; or
ii) $R^1$ has its preferred meaning and all other substituents have their basic meaning; or
iii) $R^2$ has its preferred meaning and all other substituents have their basic meaning; or
iv) $R^3$ has its preferred meaning and all other substituents have their basic meaning; or
v) $R^4$ has its preferred meaning and all other substituents have their basic meaning; or
vi) $R^5$ has its preferred meaning and all other substituents have their basic meaning; or
vii) $R^6$ has its preferred meaning and all other substituents have their basic meaning; or
viii) $R^7$ has its preferred meaning and all other substituents have their basic meaning; or
ix) $R^8$ has its preferred meaning and all other substituents have their basic meaning; or
x) A has its preferred meaning and all other substituents have their basic meaning; or
xi) B has its preferred meaning and all other substituents have their basic meaning; or
xii) D has its preferred meaning and all other substituents have their basic meaning; or
xiii) E has its preferred meaning and all other substituents have their basic meaning; or
xiv) heteroaryl has its preferred meaning and all other substituents have their basic meaning; or
xv) heterocyclyl has its preferred meaning and all other substituents have their basic meaning; or
xvi) aryl has its preferred meaning and all other substituents have their basic meaning; or
xvii) $R^1$, $R^2$, $R^3$, $R^4$, $R^5$, $R^6$, $R^7$, $R^8$, A, E, heteroaryl, heterocyclyl and aryl have their preferred meaning and B and D have their basic meaning; or
xviii) $R^1$, $R^3$, $R^4$, $R^5$ and $R^6$ have their more preferred meaning, $R^7$, $R^8$, A, D, E, heteroaryl, heterocyclyl and aryl have their preferred meaning, $R^2$ has its particularly preferred meaning and B has its basic meaning; or
xix) $R^1$ has its much more preferred meaning, $R^3$, $R^4$, $R^5$ and $R^6$ have their even much more preferred meaning, A, D, E, heteroaryl and heterocyclyl have their preferred meaning, $R^2$ has its particularly preferred meaning and B has its basic meaning; or
xx) $R^1$ has its very particularly preferred meaning, $R^2$, $R^3$, $R^4$, $R^5$ and $R^6$ have their particularly preferred meaning, A, D and E have their preferred meaning, and B has its basic meaning; or
xxi) $R^1$, $R^3$ and $R^6$ have their very particularly preferred meaning, $R^2$, $R^4$ and $R^5$ have their particularly preferred meaning, A, D and E have their preferred meaning, and B has its basic meaning; or
xxii) $R^3$ and $R^6$ have their very particularly preferred meaning, $R^1$, $R^2$, $R^4$ and $R^5$ have their particularly preferred meaning, A, D and E have their preferred meaning, and B has its basic meaning; or
xxiii) $R^1$, $R^2$, $R^3$, $R^4$, $R^5$ and $R^6$ have their particularly preferred meaning, A, D and E have their preferred meaning, and B has its basic meaning; or
xxiv) $R^1$ has its much more preferred meaning, $R^2$, $R^3$, $R^4$, $R^5$ and $R^6$ have their particularly preferred meaning, A, D, E, heteroaryl and heterocyclyl have their preferred meaning and B has its basic meaning; or
xxv) $R^1$ has its much more preferred meaning, $R^3$ and $R^6$ have their very particularly preferred meaning, $R^2$, $R^4$ and $R^5$ have their particularly preferred meaning, A, D, E, heteroaryl and heterocyclyl have their preferred meaning and B has its basic meaning; or
xxvi) $R^1$ has its much more preferred meaning, $R^3$ and $R^6$ have their very particularly preferred meaning, $R^2$, $R^4$, $R^5$, heteroaryl and heterocyclyl have their particularly preferred meaning, A, D and E have their preferred meaning and B has its basic meaning; or
xxvii) $R^1$ has its much more preferred meaning, $R^2$, $R^3$, $R^4$, $R^5$, $R^6$, heteroaryl and heterocyclyl have their particularly preferred meaning, A, D and E have their preferred meaning and B has its basic meaning; or
xxviii) $R^1$ has its much more preferred meaning, $R^3$, $R^4$, $R^5$, $R^6$, heteroaryl and heterocyclyl have their particularly preferred meaning, $R^2$, A, D and E have their preferred meaning and B has its basic meaning; or xxix) $R^1$, $R^4$, $R^5$, $R^7$, $R^8$, A, E, heteroaryl, heterocyclyl and aryl have their preferred meaning, $R^3$ and $R^6$ have their very particularly preferred meaning, $R^2$ has its particularly preferred meaning and B and D have their basic meaning; or xxx) $R^1$, $R^3$, $R^4$, $R^5$, $R^6$, A, E, heteroaryl, heterocyclyl and aryl have their preferred meaning, $R^7$ and $R^8$ have their more preferred meaning, $R^2$ has its particularly preferred meaning and B and D have their basic meaning; or xxxi) $R^1$, $R^3$, $R^4$, $R^5$, $R^6$ have their more preferred meaning, $R^2$, A, D, E, heteroaryl, heterocyclyl and aryl have their preferred meaning, $R^7$ and $R^8$ have their particularly preferred meaning and B has its basic meaning; or xxxii) $R^1$, $R^3$, $R^4$, $R^5$, $R^6$ have their more preferred meaning, A, D, E, heteroaryl, heterocyclyl and aryl have their preferred meaning, $R^2$, $R^7$ and $R^8$ have their particularly preferred meaning and B and D have their basic meaning; or xxxiii) $R^1$ has its more preferred meaning, $R^7$, A, D, E, heteroaryl, heterocyclyl and aryl have their preferred meaning, $R^4$ and $R^5$ have their even much more preferred meaning, $R^3$ and $R^6$ have their very particularly preferred meaning, $R^2$ has its particularly preferred meaning and B and D have their basic meaning; or xxxiv) $R^1$ has its much more preferred meaning, $R^3$, $R^4$, $R^5$ and $R^6$ have their more preferred meaning, $R^8$, A, D, E, heteroaryl, heterocyclyl and aryl have their preferred meaning, $R^2$ has its particularly preferred meaning and B has its basic meaning; or xxxv) $R^1$ has its much more preferred meaning, $R^3$, $R^4$, $R^5$ and $R^6$ have their even much more preferred meaning, B, D, E, heteroaryl and heterocyclyl have their preferred meaning, $R^2$ has its particularly preferred meaning and A has its basic meaning; or xxxvi) $R^1$ has its very particularly preferred meaning, $R^2$, $R^3$, $R^4$, $R^5$ and $R^6$ have their particularly preferred meaning, B, D and E have their preferred meaning, and A has its basic meaning;

As stated above, the preferred compounds of the general formula (I) are not confined to the aforementioned examples. On the contrary, all combinations of the individual substituents in their basic meaning with the preferred, more preferred, even more preferred, much more preferred, even much more preferred, particularly preferred or very particularly preferred meanings of the other substituents or all combinations of the preferred, more preferred, even more preferred, much more preferred, even much more preferred, particularly preferred or very particularly preferred meanings of the individual substituents which are not mentioned above as example are also an aspect of this invention. This only applies, of course, to the extent that the definitions of the respective substituents permit such a combination.

Particularly preferred compounds of the general formula (I) are selected from the group consisting of: 4-(1H-benzimidazol-2-yl)-6-(4-hydroxy-3-methoxy-5-methylaminomethylphenyl)-2H-pyridazin-3-one, 2-(3-oxo-6-pyridin-4-yl-2,3-dihydropyridazin-4-yl)-1H-benzimidazole-5-carboxylic acid (2-diethylaminoethyl)-amide, 4-(6-tri-fluoromethyl-1H-benzimidazole-2-yl)-6-pyridin-4-yl-2H-pyridazin-3-one, 4-(6-methoxy-1H-benzimidazol-2-yl)-6-pyridin-4-yl-2H-pyridazin-3-one, 4-(5-chloro-1H-benzimidazol-2-yl)-6-methyl-2H-pyridazin-3-one, 4-(6-chloro-1H-benzimidazol-2-yl)-6-(4-hydroxy-3,5-dimethylphenyl)-2H-pyridazin-3-one, 4-(5-fluoro-1H-benzimidazol-2-yl)-6-pyridin-4-yl-2H-pyridazin-3-one, 6-(4-hydroxy-3-methoxyphenyl)-4-(6-tri-fluoromethyl-1H-benzimidazol-2-yl)-2H-pyridazin-3-one, 6-(2-butylaminopyrimidin-4-yl)-4-(6-chloro-1H-benzimidazol-2-yl)-2H-pyridazin-3-one, 4-(1H-benzimidazol-2-yl)-6-pyridin-4-yl-2H-pyridazin-3-one, 6-[2-(2-morpholin-4-yl-ethylamino)pyrimidin-4-yl]-4-(6-tri-fluoromethyl-1H-benzimidazol-2-yl)-2H-pyridazin-3-one and 4-(3H-imidazol[4,5-c]pyridin-2-yl)-6-pyridin-4-yl-2H-pyridazin-3-one;

It is expressly pointed out once again that the above statements concerning the salts, stereoisomers, prodrugs, N-oxides etc. apply also to the preferred and particularly preferred compounds of formula (I); in particular, the respective physiologically tolerated salts are also included.

In a further embodiment of the present invention, the compounds of formula (I) are defined as follows:

A is $CR^3$ or N;
B is $Cr^4$ or N;
D is $CR^5$ or N;
E is $CR^6$ or N;
where a maximum three of the substituents A, B, D and E can simultaneously be N;

$R^1$ is halogen;
  unsubstituted or at least monosubstituted $C_1$-$C_{10}$-alkyl,
  where the substituents are selected from the group consisting of: halogen, —CN, $NO_2$, —$OR^7$, —$C(O)R^7$, —$C(O)OR^7$, —O—$C(O)R^7$, —$NR^7R^8$, —NHC(O)$R^7$, —$C(O)NR^7R^8$, —NHC(S)$R^7$, —$C(S)NR^7R^8$, —$SR^7$, —$S(O)R^7$, —$SO_2R^7$, —$NHSO_2R^7$, —$SO_2NR^7R^8$, —O—$SO_2R^7$, —$SO_2$—O—$R^7$, aryl, heteroaryl, heterocyclyl, tri-fluoromethyl and tri-fluoromethoxy,
  and heterocyclyl, aryl and heteroaryl may in turn be at least monosubstituted by $C_1$-$C_6$-alkyl, $C_1$-$C_6$-alkoxy, halogen, tri-fluoromethyl, tri-fluoromethoxy or OH;
  unsubstituted or at least monosubstituted aryl or heteroaryl,
  where the substituents are selected from the group consisting of: halogen, —CN, $NO_2$, —$CH_2$—$R^7$, —$OR^7$, —$C(O)R^7$, —$C(O)OR^7$, —O—$C(O)R^7$, —$NR^7R^8$, —NHC(O)$R^7$, —$C(O)NR^7R^8$, —NHC(S)$R^7$, —$C(S)NR^7R^8$, —$SR^7$, —$S(O)R^7$, —$SO_2R^7$, —$NHSO_2R^7$, —$SO_2NR^7R^8$, —O—$SO_2R^7$, —$SO_2$—O—$R^7$, aryl, heteroaryl, tri-fluoromethyl and tri-fluoromethoxy,
  and aryl and heteroaryl may in turn be at least monosubstituted by $C_1$-$C_6$-alkyl, $C_1$-$C_6$-alkoxy, halogen, tri-fluoromethyl, tri-fluoromethoxy or OH;

$R^2$ is hydrogen or $C_1$-$C_{10}$-alkyl;
$R^3$, $R^4$, $R^5$ and $R^6$ are independently of one another selected from the group consisting of: hydrogen, halogen, —CN, $NO_2$, —$CH_2$—$R^8$, —$OR^8$, —$C(O)R^8$, —$C(O)OR^8$, —O—$C(O)R^8$, —$NR^7R^8$; —NHC(O)$R^8$, —$C(O)NR^7R^8$, —NHC(S)$R^8$, —$C(S)NR^7R^8$, —$SR^8$, —$S(O)R^8$, —$SO_2R^8$, —$NHSO_2R^8$, —$SO_2NR^7R^8$, —O—$SO_2R^8$, —$SO_2$—O—$R^8$, aryl, heteroaryl, heterocyclyl, tri-fluoromethyl and tri-fluoromethoxy,
  and heterocyclyl, aryl and heteroaryl may in turn be at least monosubstituted by $C_1$-$C_6$-alkyl, $C_1$-$C_6$-alkoxy, oxo, halogen, tri-fluoromethyl, tri-fluoromethoxy or OH;

$R^7$ and $R^8$ are independently of one another:
  H;
  unsubstituted or at least monosubstituted $C_1$-$C_{10}$-alkyl, $C_2$-$C_{10}$-alkenyl, $C_2$-$C_{10}$-alkynyl, heterocyclyl, aryl or heteroaryl,
  where the substituents are selected from the group consisting of: heteroaryl, heterocyclyl, aryl, halogen, OH, oxo, $C_1$-$C_{10}$-alkoxy, ($C_1$-$C_{10}$-alkyl)thio-, COOH, —COO—($C_1$-$C_6$-alkyl), —$CONH_2$, tri-fluoromethyl, tri-fluoromethoxy; CN, $NH_2$, ($C_1$-$C_{10}$-alkyl)amino- and di-($C_{61}$-$C_{10}$-alkyl)amino-, and heterocyclyl, aryl and heteroaryl may in turn be at least monosubstituted by $C_1$-$C_6$-alkyl, $C_1$-$C_6$-alkoxy, oxo, tri-fluoromethyl, tri-fluoromethoxy, fluorine, chlorine or OH;

heteroaryl is a 5 to 10-membered, aromatic, mono- or bicyclic heterocycle which comprises one or more heteroatoms selected from N, O and S;

aryl is a 5 to 10-membered, aromatic, mono- or bicyclic system.

Heterocyclyl is a 5 to 10-membered, nonaromatic, mono- or bicyclic heterocycle which comprises one or more heteroatoms selected from N, O and S;

or a physiologically tolerated salt thereof.

In this further embodiment, $R^1$ is preferably not unsubstituted or at least monosubstituted pyrazolo[1,5-a]pyridinyl.

More preferred compounds of this further embodiment are defined as follows:

A is $CR^3$;
B is $CR^4$ or N;
D is $CR^5$;
E is $CR^6$;
$R^1$ is unsubstituted or at least monosubstituted phenyl, pyridinyl, pyrimidinyl, pyrazolyl, thiophenyl, oxazolyl, isoxazolyl, benzo[b]thiophenyl, benzodioxolyl or thiazolo[3,2-b][1,2,4]-triazolyl, where the substituents are selected from the group consisting of: halogen, $C_1$-$C_6$-alkyl, phenyl-($C_1$-$C_6$-alkyl)-, OH, $C_1$-$C_6$-alkoxy, ($C_1$-$C_6$-alkyl)thio-, —O-phenyl, —$NH_2$, —N($C_1$-$C_6$-alkyl)$_2$, —NH($C_1$-$C_6$-alkyl), —NH(amino-($C_1$-$C_6$-alkyl-)), —NH(($C_1$-$C_6$-alkyl)amino-($C_1$-$C_6$-alkyl-)), —NH(di-($C_1$-$C_6$-alkyl)amino-($C_1$-$C_6$-alkyl-)), —NH(heterocyclyl-($C_1$-$C_6$-alkyl-)), —NH(heteroaryl-($C_1$-$C_6$-alkyl-)), —NH(phenyl-($C_1$-$C_6$-alkyl-)), tri-fluoromethyl, tri-fluoromethoxy, phenyl and heteroaryl, and heterocyclyl, phenyl and heteroaryl may in turn be at least monosubstituted by $C_1$-$C_3$-alkyl, $C_1$-$C_3$-alkoxy, fluorine, chlorine, tri-fluoromethyl, tri-fluoromethoxy or OH;

$R^2$ is hydrogen;

$R^3$, $R^4$, $R^5$ and $R^6$ are independently of one another selected from the group consisting of:

hydrogen, fluorine, chlorine, bromine, —CN, $C_1$-$C_6$-alkyl, —OH, $C_1$-$C_6$-alkoxy, —C(O)OH, —C(O)O—($C_1$-$C_6$-alkyl), —$NH_2$, —N($C_1$-$C_6$-alkyl)$_2$, —NH($C_1$-$C_6$-alkyl), —NH(amino-($C_1$-$C_6$-alkyl-)), —NH(hydroxy-($C_1$-$C_6$-alkyl-)), —NH(($C_1$-$C_6$-alkyl)amino-($C_1$-$C_6$-alkyl-)), —NH(di-($C_1$-$C_6$-alkyl)amino-($C_1$-$C_6$-alkyl-)), —NH(heterocyclyl-($C_1$-$C_6$-alkyl-)), —NH(heteroaryl-($C_1$-$C_6$-alkyl-)), —NH(phenyl-($C_1$-$C_6$-alkyl-)), —C(O)$NH_2$, —C(O)NH—($C_1$-$C_6$-alkyl), —C(O)N($C_1$-$C_6$-alkyl)$_2$, —C(O)NH($C_1$-$C_6$-alkyl), —C(O)NH(amino-($C_1$-$C_6$-alkyl-)), —C(O)NH(hydroxy-($C_1$-$C_6$-alkyl-)), —C(O)NH(($C_1$-$C_6$-alkyl)amino-($C_1$-$C_6$-alkyl-)), —C(O)NH(di-($C_1$-$C_6$-alkyl)amino-($C_1$-$C_6$-alkyl-)), —C(O)NH(heterocyclyl-($C_1$-$C_6$-alkyl-)), —C(O)NH(heteroaryl-($C_1$-$C_6$-alkyl-)), —C(O)NH(phenyl-($C_1$-$C_6$-alkyl-)), heterocyclyl, tri-fluoromethyl and tri-fluoromethoxy, and heteroaryl, heterocyclyl and phenyl may in turn be at least monosubstituted by $C_1$-$C_6$-alkyl, $C_1$-$C_6$-alkoxy, halogen, tri-fluoromethyl, tri-fluoromethoxy or OH;

heteroaryl is imidazolyl, thiophenyl, furanyl, oxazolyl, isoxazolyl, pyridinyl, pyrimidinyl, pyrazolyl, benzo[b]thiophenyl, thiazolo[3,2-b][1,2,4]-triazolyl, pyrrolyl, quinolinyl, isoquinolinyl, 1,2,3,4-tetrahydroquinolinyl, benzoimidazolyl, indolyl or 1,3-benzodioxolyl;

heterocyclyl is 2-oxoazepanyl, tetrahydrofuranyl, 1,3-dioxolanyl, morpholinyl, pyrrolidinyl, piperazinyl or piperidinyl;

or a physiologically tolerated salt thereof.

The compounds are prepared according to processes known per se by preparing the monoacyl derivatives (IV) from active acid derivatives of the formula (II), where Y is a leaving group, preferably —OH, $C_1$-$C_{10}$-alkoxy, chlorine, —O—C(O)—($C_1$-$C_{10}$-alkyl or —O—C(O)—O—($C_1$-$C_{10}$-alkyl), and 1,2-diaminophenyl or 1,2-diaminoheterocyclyl derivatives of the formula (III), and cyclizing the monoacyl derivatives in a suitable manner. Suitable cyclizing agents may be acids such as glacial acetic acid, hydrochloric acid, sulfuric acid, phosphoric acid or dehydrating agents such as phosphorus pentoxide. After the cyclization, the substituents A, B, D, E, $R^1$ and $R^2$ (and the other substituents) can where appropriate be modified by known processes to give the claimed compounds of the formula (I).

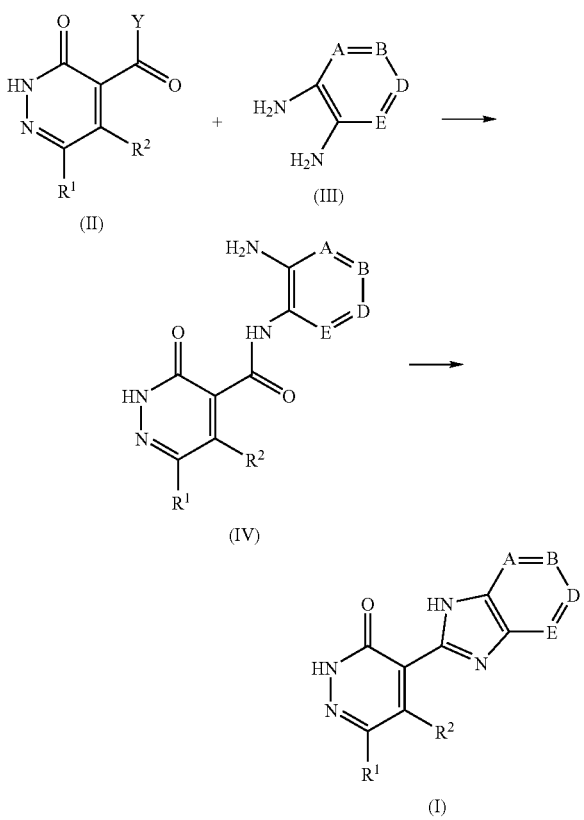

A further known preparation method consists of reacting aldehyde, i.e. Y in formula (II) equals hydrogen, with the compounds of the formula (III), in which case the initially formed dihydro compounds are converted by air or (pure) oxygen or other oxidants into the compounds of the formula (I).

A further possibility is to prepare the compounds of the general formula (I) by palladium-catalyzed coupling in a Suzuki reaction (I. Parrot et al., Synthesis; 7; 1999; 1163 to 1168). In this case, a compound of the formula (VI), where Y1 equals halogen, B(OH)$_2$ or Sn(C$_1$-C$_{10}$-alkyl) and Y2 equals H or a protective group, is reacted with a compound of the formula (V).

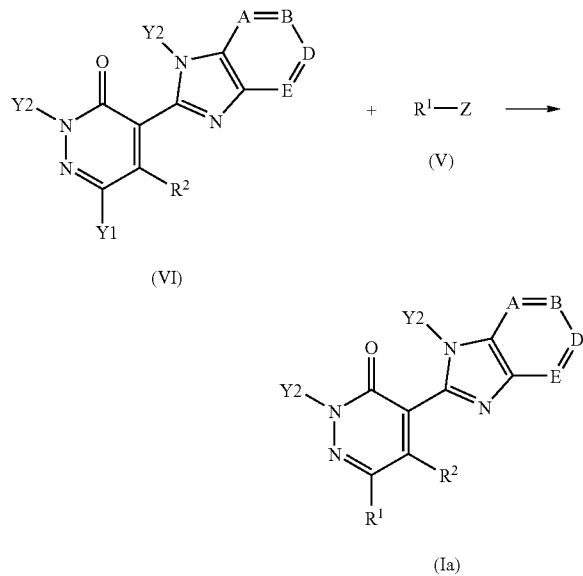

R$^1$ in formula (V) equals unsubstituted or at least monosubstituted aryl or heteroaryl as defined for formula (I). Z can be, for example, B(OH)$_2$, B(C$_1$-C$_{10}$-alkyl)$_2$, Sn—(C$_1$-C$_{10}$-alkyl)$_3$, Zn—(C$_1$-C$_{10}$-alkyl) or halogen. Where Y2 is a protective group, the latter is removed again by methods known to the skilled worker following the reaction of (VI) with (V). All protective groups known to the skilled worker can be used as protective group, preferably trimethylsilylethoxymethyl-. All palladium complexes known to the skilled worker are suitable for carrying out the palladium-catalyzed coupling, with preference for the use of Pd(triphenylphosphine)$_4$ (Pd-tetrakis catalyst), which is preferably formed in situ from palladium acetate. Formula (Ia) corresponds to formula (I) for Y2═H and R$^1$ equal to unsubstituted or at least monosubstituted aryl or heteroaryl. All synthetic reactions for compounds of the formula (I) are known in principle to the skilled worker and can accordingly be carried out under standard conditions (identical or with slight modifications) as described in the literature (see, for example, in Houben-Weyl, Methoden der organischen Chemie, Thieme-Verlag, Stuttgart or Organic Reactions, John Wiley & Sons, New York). Based on the circumstances in the individual case, it may, in order to avoid side reactions during the preparation for compounds of formula (I), be necessary or advantageous to block functional groups temporarily through the introduction of protective groups, and to remove them again later. It is also possible where appropriate for functional groups to be introduced in the form of precursor groups, in which case the latter are converted in a later reaction step into the desired functional group. Such synthetic strategies, protective groups and precursor groups suitable for the individual case are known to the skilled worker. Where necessary, the compounds of formula (I) can be purified by known workup methods, for example by recrystallization or chromatography. The starting materials for preparing compounds of formula (I) are either commercially available or they can be prepared by processes known from the literature. Compounds and intermediates prepared by the synthetic processes described above are a further aspect of the present invention.

The present invention also relates to the use of compounds of the general formula (I) as pharmaceutical or medicament. Concerning the definition of the substituents A, B, D, E, R$^1$ and R$^2$ (and the other substituents defined via the aforementioned substituents), reference is made to the statements concerning the compounds as such.

The use of compounds of the general formula (I) as pharmaceuticals, where one, more than one or all of the aforementioned substituents have the abovementioned preferred, more preferred, even more preferred, much more preferred, even much more preferred, particularly preferred or very particularly preferred meaning, including all combinations with one another, is likewise an aspect of the present invention.

The compounds of general formula (I) are kinase inhibitors and can therefore be employed for the treatment of diseases, which may result from an abnormal activity of kinases. As abnormal kinase activity, there may be mentioned, for example, that of PI3K, AkT, GSK-3β and the like.

In particular, compounds according to the present invention can be used for the inhibition of the kinase GSK-3β. This effect is particularly relevant for the treatment of metabolic diseases such as type II diabetes or neurodegenerative diseases such as Alzheimer's disease.

Furthermore, compounds according to the general formula (I) have an inhibitory effect in respect of the phosphorylation of the tau-protein. This effect is particularly relevant for the treatment of neurodegenerative diseases such as Alzheimer's disease.

Examples of diseases which can be treated with the compounds according to the present invention, include: neurodegenerative diseases, strokes, cranial and spinal traumas and peripheral neuropathies, obesity, metabolic diseases, type II diabetes, essential hypertension, atherosclerotic cardiovascular diseases, polycystic ovary syndrome, syndrome X, immunodeficiency or cancer. Neurodegenerative diseases are preferably: Alzheimer's disease, Parkinson's disease, frontoparietal dementia, corticobasal degeneration and Pick's disease.

Compounds according to the present invention are preferably employed for the treatment of metabolic diseases, in particular of type II diabetes.

In another embodiment of the present invention, the compounds according to the general formula (I) are preferably employed for the treatment of neurodegenerative diseases, in particular of Alzheimer's disease.

In the above statements the term treatment also includes prophylaxis, therapy or curing of the abovementioned diseases.

All references to "compound(s) according to formula (I)" refer hereinbelow to a compound/compounds of the formula (I) as described above and also to their salts, solvates and physiologically functional derivatives as described herein.

The compounds of the formula (I) can be administered to animals and humans, preferably to mammals and humans, and in particular to humans. The compounds of the formula (I) can be administered as pharmaceuticals by themselves, in mixtures with one another or in mixtures with other pharmaceuticals or in the form of pharmaceutical preparations. Further subjects of the present invention therefore also are the use of the compounds of the formula (I) for preparing one or more medicaments for prophylaxis and/or treatment of the abovementioned diseases, pharmaceutical preparations (or pharmaceutical compositions) comprising an effective dose of at least one compound of the formula (I) as well as pharmaceutical preparations comprising an effective dose of at least one compound of the formula (I) for prophylaxis and/or treatment of the abovementioned diseases.

The amount of a compound according to formula (I) which is required in order to attain the desired biological effect depends on a number of factors, for example the specific compound selected, the intended use, the type of administration and the clinical state of the patient. In general, the daily dose is in the range from 0.3 mg to 100 mg (typically from 3 mg to 50 mg) per day per kilogram of body weight, for example 3-10 mg/kg/day. An intravenous dose can be, for example, in the range from 0.3 mg to 1.0 mg/kg and can be administered in a suitable manner as an infusion of 10 ng to 100 ng per kilogram per minute. Suitable infusion solutions for these purposes may contain, for example, from 0.1 ng to 10 mg, typically from 1 ng to 10 mg per milliliter. Individual doses may contain, for example, from 1 mg to 10 g of the active compound. Thus, ampoules for injections can contain, for example, from 1 mg to 100 mg, and orally administerable individual dose formulations such as, for example, tablets or capsules can contain, for example, from 1.0 to 1000 mg, typically from 10 to 600 mg. In the case of pharmaceutically acceptable salts, the abovementioned masses relate to the mass of the free compound on which the salt is based. The compound used for the prophylaxis or therapy of the abovementioned conditions may be the compounds according to formula (I) themselves, but they are preferably present in the form of a pharmaceutical composition together with an acceptable carrier. The carrier must be naturally acceptable, in the sense that it is compatible with the other ingredients of said composition and is not harmful to the patient's health (physiologically tolerable). The carrier may be a solid or a liquid or both and is preferably formulated with the compound as an individual dose, for example as a tablet which may contain from 0.05% to 95% by weight of the active compound. Further pharmaceutically active substances may also be present, including further compounds according to formula (I). The pharmaceutical compositions of the invention may be prepared according to any of the known pharmaceutical methods which essentially comprise mixing the ingredients with pharmacologically acceptable carriers and/or excipients.

Besides at least one compound according to formula (I) as well as one or more carriers, the pharmaceutical preparations according to the invention can also contain additives. As additives can be employed, for example: fillers, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The pharmaceutical compositions of the invention may be in the form of a pill, tablet, coated tablet, lozenge, granule, capsule, hard or soft gelatin capsule, aqueous solution, alcoholic solution, oily solution, syrup, emulsion, suspension, suppository, pastille, solution for injection or infusion, ointment, tincture, cream, lotion, powder, spray, transdermal therapeutic systems, nasal spray, aerosol, aerosol mixture, microcapsule, implant, rod or patch.

Pharmaceutical compositions of the invention are those which are suitable for oral, rectal, topical, peroral (e.g. sublingual) and parenteral (e.g. subcutaneous, intramuscular, intradermal or intravenous) administration, although the most suitable manner of administration depends in each individual case on the nature and severity of the condition to be treated and on the nature of the compound according to formula (I) used in each case. Sugar-coated formulations and sugar-coated delayed-release formulations, too, are included within the scope of the invention. Preference is given to acid-resistant and enteric formulations. Suitable enteric coatings include cellulose acetate phthalate, polyvinyl acetate phthalate, hydroxypropyl-methylcellulose phthalate and anionic polymers of methacrylic acid and methyl methacrylate.

Suitable pharmaceutical compounds for oral administration may be present in separate units such as, for example, capsules, cachets, lozenges or tablets, which in each case contain a particular amount of the compound according to formula (I); as powders (gelatin capsules or cachets) or granules; as solution or suspension in an aqueous or nonaqueous liquid; or as an oil-in-water or water-in-oil emulsion. As already mentioned, said compositions can be prepared according to any suitable pharmaceutical method which includes a step in which the active compound and the carrier (which may comprise one or more additional components) are contacted. In general, the compositions are prepared by uniform and homogeneous mixing of the active compound with a liquid and/or finely dispersed solid carrier, after which the product is shaped, if necessary. Thus a tablet, for example, may be prepared by pressing or shaping a powder or granules of the compound, where appropriate with one or more additional components. Pressed tablets can be prepared by tableting the compound in free-flowing form, for example a powder or granules, mixed, where appropriate, with a binder, lubricant, inert diluent and/or one or more surface active/dispersing agents in a suitable machine. Shaped tablets can be prepared by shaping the pulverulent compound, moistened with an inert liquid diluent, in a suitable machine. As diluents can be used, for example, starch, cellulose, sucrose, lactose or silica. The pharmaceutical compositions of the invention may also comprise substances other than diluents, for example one or more lubricants such as magnesium stearate or talc, a coloring, a coating (sugar-coated tablets) or a varnish.

Pharmaceutical compositions which are suitable for peroral (sublingual) administration include lozenges which contain a compound according to formula (I) with a flavoring, usually sucrose and gum arabic or tragacanth, and pastilles which comprise the compound in an inert base such as gelatin and glycerol or sucrose and gum arabic.

Suitable pharmaceutical compositions for parenteral administration preferably comprise sterile aqueous preparations of a compound according to formula (I) which are preferably isotonic with the blood of the intended recipient. These preparations are preferably administered intravenously, although they may also be administered subcutaneously, intramuscularly or intradermally as an injection. Said preparations may preferably be prepared by mixing the compound with water and rendering the obtained solution sterile and isotonic with the blood. Injectable compositions of the invention generally contain from 0.1 to 5% by weight of the active compound.

These sterile compositions for parenteral administration may be preferably solutions which are aqueous or nonaqueous, suspensions or emulsions. As solvent or vehicle, there may be used water, propylene glycol, polyethylene glycol, vegetable oils, in particular olive oil, organic esters for injection, for example ethyl oleate or other suitable organic solvents. These compositions may also contain adjuvants, in particular wetting, isotonicizing, emulsifying, dispersing and stabilizing media. The sterilization may be carried out in several ways, for example by an aseptic filtration, by incorporating sterilizing agents into the composition, by irradiation or by heating. They may also be prepared in the form of sterile solid compositions which may be dissolved at the time of use in sterile water or in any other sterile medium for injection.

Suitable pharmaceutical compositions for rectal administration are preferably present as individual dose suppositories. These may be prepared by mixing a compound according to formula (I) with one or more conventional solid carriers, for example cocoa butter, and shaping the resulting mixture.

Suitable pharmaceutical compositions for topical application to the skin are preferably present as ointment, cream, lotion, paste, spray, aerosol or oil. Carriers which may be used are petroleum jelly, lanolin, polyethylene glycols, alcohols and combinations of two or more of these substances. In general, the active compound is present at a concentration of from 0.1 to 15%, for example from 0.5 to 2%, by weight of the composition.

Transdermal administration is also possible. Suitable pharmaceutical compositions for transdermal administration may be present as individual patches which are suitable for long-term close contact with the epidermis of the patient. Such patches suitably contain the active compound in an optionally buffered aqueous solution, dissolved and/or dispersed in an adhesive or dispersed in a polymer. A suitable active compound concentration is from approx. 1% to 35%, preferably approx. 3% to 15%. A particular possibility is the release of the active compound by electro-transport or iontophoresis, as described, for example, in Pharmaceutical Research, 2(6): 318 (1986).

The following examples illustrate the pharmaceutical compositions according to the invention:

EXAMPLE A

Gelatin capsules containing a dose of 50 mg of active compound and having the following composition are prepared according to the usual technique:

| | |
|---|---|
| Compound of formula (I) | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE B

Gelatin capsules (tablet) containing a dose of 50 mg of active compound and having the following composition are prepared according to the usual technique:

| | |
|---|---|
| Compound of formula (I) | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |

Mixture of hydroxymethylcellulose, glycerin, titanium oxide (72-3.5-24.5) qs 1 finished film-coated tablet of 245 mg

EXAMPLE C

A solution for injection containing 10 mg of active compound and having the following composition is prepared:

| | |
|---|---|
| Compound of formula (I) | 10 mg |
| Benzoic acid | 80 mg |
| Benzyl alcohol | 0.06 ml |
| Sodium benzoate | 80 mg |
| Ethanol at 95% | 0.4 ml |
| Sodium hydroxide | 24 mg |
| Propylene glycol | 1.6 ml |
| Water | qs 4 ml |

Another aspect of the present invention is the combination of compounds of the formula (I) with other pharmaceutically active substances not covered by formula (I).

The compounds of the formula (I) are distinguished by beneficial actions on the metabolism of lipids, and they are particularly suitable for weight reduction and, after weight reduction, for maintaining a reduced weight in mammals and as anorectic agents. The compounds are distinguished by their low toxicity and their few side effects.

The compounds may be employed alone or in combination with other weight-reducing or anorectic active compounds. Further anorectic active compounds of this kind are mentioned, for example, in the Rote Liste, Chapter 01 under weight-reducing agents/appetite suppressants, and may also include those active compounds which increase the energy turnover of the organism and thus lead to weight reduction or else those which influence the general metabolism of said organism such that increased calorie intake does not cause an enlargement of the fat depots and a normal calorie intake causes a reduction in the fat depots of said organism. The compounds are suitable for the prophylaxis and, in particular, for the treatment of problems of excess weight or obesity.

The compounds of formula (I) have a beneficial effect on the glucose metabolism, they particularly lower the blood-sugar level and can be used for treatment of type I and type II diabetes. The compounds can therefore be used alone or in combination with other blood-sugar lowering active compounds (antidiabetics). In a further aspect of the invention, the compounds of the formula I may be administered in combination with one or more further pharmacologically active substances which may be selected, for example, from the group consisting of antidiabetics, antiadipose agents, blood-pressure-lowering active compounds, lipid reducers and active compounds for the treatment and/or prevention of complications caused by diabetes or associated with diabetes.

Suitable anti-diabetics include insulins, amylin, GLP-1 and GLP-2 derivatives such as, for example, those disclosed by Novo Nordisk A/S in WO 98/08871 and also oral hypoglycemic active compounds.

Said oral hypoglycemic active compounds preferably include sulfonylureas, biguanides, meglitinides, oxadiazolidinediones, thiazolidinediones, glucosidase inhibitors, glucagon receptor antagonists, GLP-1 agonists, potassium channel openers such as, for example, those disclosed by Novo Nordisk A/S in WO 97/26265 and WO 99/03861, insulin sensitizers, activators of insulin receptor kinase, inhibitors of liver enzymes involved in the stimulation of gluconeogenesis and/or glycogenolysis, for example glycogen phosphorylase inhibitors, modulators of glucose uptake and glucose elimination, lipid metabolism-modifying compounds such as antihyperlipidemic active compounds and antilipidemic active compounds, for example HMGCoA-reductase inhibitors, inhibitors of cholesterol transport/cholesterol uptake, inhibitors of bile acid reabsorption or inhibitors of microsomal triglyceride transfer protein (MTP), compounds which reduce food intake, PPAR and RXR agonists and active compounds which act on the ATP-dependent potassium channel of beta cells.

In one embodiment of the present invention, the present compounds are administered in combination with insulin.

In another embodiment, the compounds of the present invention are administered in combination with a sulfonylurea such as, for example, tolbutamide, glibenclamide, glimepiride, glipizide, gliquidone, glisoxepide, glibornuride or gliclazide. In another embodiment, the compounds of the present invention are administered in combination with a biguanide such as, for example, metformin. In another embodiment, the compounds of the present invention are administered in combination with a meglitinide such as, for example, repaglinide. In yet another embodiment, the compounds of the present invention are administered in combination with a thiazolidinedione such as, for example, troglitazone, ciglitazone, pioglitazone, rosiglitazone or the compounds disclosed by Dr. Reddy's Research Foundation in WO 97/41097, in particular 5-[[4-[(3,4-dihydro-3-methyl-4-oxo-2-quinazolinylmethoxy]phenyl]methyl]-2,4-thiazolidinedione.

In another embodiment, the compounds of the present invention are administered in combination with an α-glucosidase inhibitor such as, for example, miglitol or acarbose.

In another embodiment, the compounds of the present invention are administered in combination with an active compound which acts on the ATP-dependent potassium channel of the beta cells, such as, for example, tolbutamide, glibenclamide, glimepiride, glipizide, gliclazide or repaglinide. In yet another embodiment, the compounds of the present invention are administered in combination with an antihyperlipidemic active compound or an antilipidemic active compound such as, for example, cholestyramine, colestipol, clofibrate, fenofibrate, gemfibrozil, lovastatin, pravastatin, simvastatin, atorvastatin, cerivastatin, fluvastatin, probucol, ezetimibe or dextrothyroxine.

In another embodiment, the compounds of the present invention are administered in combination with more than one of the aforementioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

Furthermore, the compounds of the invention may be administered in combination with one or more antiobesity agents or appetite-controlling active compounds.

Such active compounds may be selected from the group consisting of CART agonists, NPY antagonists, MC4 agonists, orexin antagonists, H3 agonists, TNF agonists, CRF agonists, CRF BP antagonists, urocortin agonists, β3 agonists, MSH (melanocyte-stimulating hormone) agonists, CCK agonists, serotonin re-uptake inhibitors, mixed serotonin and noradrenaline reuptake inhibitors, 5HT modulators, MAO inhibitors, bombesin agonists, galanin antagonists, growth hormone, growth-hormone-releasing compounds, TRH agonists, uncoupling protein 2 or 3 modulators, leptin agonists, dopamine agonists (bromocriptine, Doprexin), lipase/amylase inhibitors, cannabinoid receptor 1 antagonists, modulators of acylation-stimulating protein (ASP), PPAR modulators, RXR modulators, hCNTF mimetics or TR-β agonists.

In one embodiment of the invention, the antiobesity agent is leptin or modified leptin. In another embodiment, the antiobesity agent is dexamphetamine or amphetamine. In another embodiment, the antiobesity agent is fenfluramine or dexfenfluramine. In yet another embodiment, the antiobesity agent is sibutramine or the mono- and bis-demethylated active metabolites of sibutramine. In another embodiment, the antiobesity agent is orlistat. In another embodiment, the antiobesity agent is mazindol, diethylpropion or phentermine.

Furthermore, the compounds of the present invention may be administered in combination with one or more antihypertensive active compounds. Examples of antihypertensive active compounds are betablockers such as alprenolol, atenol, timolol, pindolol, propranolol and metoprolol, ACE (angiotensin-converting enzyme) inhibitors such as, for example, benazepril, captopril, enalapril, fosinopril, lisinopril, quinapril and ramipril, calcium channel blockers such as nifedipine, felodipine, nicardipine, isradipine, nimodipine, diltiazem and verapamil, and also alphablockers such as doxazosin, urapidil, prazosin and terazosin. Furthermore, reference may be made to Remington: The Science and Practice of Pharmacy, 19th edition, Gennaro, editor, Mack Publishing Co., Easton, Pa., 1995.

It is self-evident that every suitable combination of the compounds of the invention with one or more of the aforementioned compounds and optionally one or more other pharmacologically active substances is to be regarded as covered by the scope of the present claimed invention. The following examples are provided to more specifically define and describe particular embodiments of the claimed invention. They are for illustrative purposes only and should not be construed as limiting the spirit and scope of the invention as later defined by the claims that follow.

EXAMPLE 1

Methyl 2-(3-oxo-6-pyridin-4-yl-2,3-dihydropyridazin-4-yl)-1H-benzimidazole-5-carboxylate

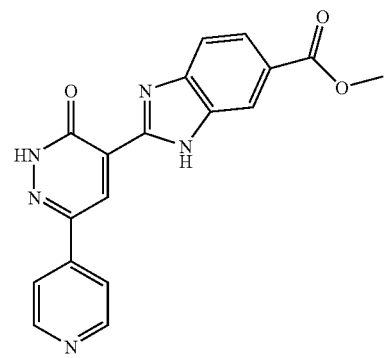

a) Methyl 4-amino-3-[(3-oxo-6-pyridin-4-yl-2,3-dihydropyridazine-4-carbonyl)-amino]benzoate A mixture consisting of 2.1 g of 3-oxo-6-pyridin-4-yl-2,3-dihydropyridazine-4-carboxylic acid, 4 ml of thionyl chloride and 20 ml of dimethoxyethane is stirred at 100° C. for 5 hours and then evaporated to dryness in vacuo. The residue is suspended in 20 ml of dimethoxyethane, mixed with 3 g of triethylamine and 1.7 g of methyl 3,4-diaminobenzoate and stirred at room temperature overnight. The volatile constituents are stripped off in vacuo, and the residue is stirred with 10 ml of saturated sodium bicarbonate solution and filtered off with suction.

Yield: 1.3 g m.p.: 352° C.

b) Methyl 2-(3-oxo-6-pyridin-4-yl-2,3-dihydro-pyridazin-4-yl)-1H-benzimidazole-5-carboxylate A mixture of 1.3 g of methyl 4-amino-3-[(3-oxo-6-pyridin-4-yl-2,3-dihydro-pyridazine-4-carbonyl)amino]benzoate and 20 ml of glacial acetic acid is heated with stirring at 100° C. for 10 hours. The precipitate which has formed is filtered off with suction, washed with water and dried in vacuo at 50° C.

Yield: 1.07 g m.p.: >300° C. (decomp.)

EXAMPLE 2

2-(3-Oxo-6-pyridin-4-yl-2,3-dihydropyridazin-4-yl)-1H-benzimidazole-5-carboxylic acid

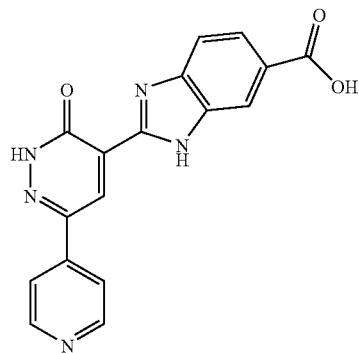

A mixture consisting of 500 mg of methyl 4-amino-3-[(3-oxo-6-pyridin-4-yl-2,3-dihydropyridazine-4-carbonyl) amino]benzoate, 6 ml of tetrahydrofuran (THF), 6 ml of methanol, 6 ml of water and 173 mg of lithium hydroxide is stirred at 50° C. for 5 hours. After cooling to room temperature, the pH is adjusted to 4-5 with 1N HCl, whereupon a precipitate separates out and is filtered off with suction and then washed with water and dried in vacuo.

Yield: 380 mg m.p.: >300° C.

EXAMPLE 3

2-(3-Oxo-6-pyridin-4-yl-2,3-dihydropyridazin-4-yl)-1H-benzimidazole-5-carboxylic acid (2-diethylaminoethyl)amide

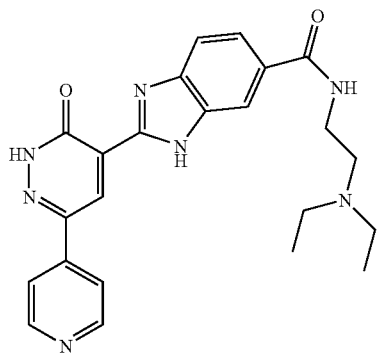

A mixture consisting of 50 mg of 2-(3-oxo-6-pyridin-4-yl-2,3-dihydropyridazin-4-yl)-1H-benzoimidazole-5-carboxylic acid, 0.065 ml of triethylamine and 1.5 ml of dimethylformamide (DMF) is stirred at room temperature for 10 minutes, mixed with 68.4 mg of O-(7-azabenzotriazol-1-yl)-N,N,N',N'-tetramethyluronium hexafluorophosphate (Hatu) and stirred at room temperature for a further 30 minutes. Then 21 mg of diethylaminoethylamine are added, and the mixture is stirred at 50° C. for 3 hours. After cooling, it is diluted with 5 ml of water, and the precipitate is filtered off with suction and stirred with isopropanol at 60° C., filtered off with suction and dried in vacuo.

Yield: 53 mg m.p.: 263° C.

EXAMPLE 4

4-(5-Chloro-1H-benzimidazol-2-yl)-6-(2-ethylaminopyrimidin-4-yl)-2H-pyridazin-3-one

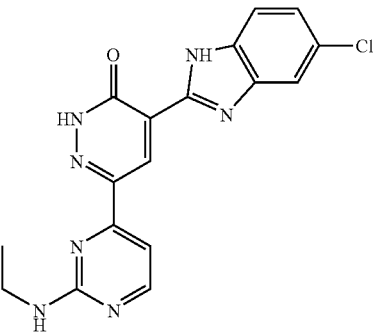

a) 1-(2-Ethylaminopyrimidin-4-yl)ethanone

A mixture of 6 g of 1-dimethylamino-4,4-dimethoxypent-1-en-3-one, 3.96 g of N-ethylguanidine hydrochloride and 26 ml of 20% strength ethanolic sodium ethoxide solution is heated under reflux for 2 hours. After cooling, the solid is filtered off with suction, and the filtrate is concentrated in vacuo and mixed with 20 ml of trifluoroacetic acid and 2 ml of water and stirred at room temperature overnight. Then 50 ml of water are added, the pH is adjusted to 10 with sodium carbonate, and the mixture is extracted twice with 25 ml of ethyl acetate each time. The organic phase is dried over sodium sulfate and concentrated. The resulting oily residue is purified by column chromatography (silica gel, mobile phase: methylene chloride:methanol=98:2).

Yield: 1.9 g m.p.: 70.9° C.

b) Diethyl 2-[2-(2-ethylaminopyrimidin-4-yl)-2-oxoethyl]-2-hydroxy-malonate

A mixture consisting of 1.9 g of 1-(2-ethylaminopyrimidin-4-yl)ethanone and 1.86 ml of diethyl ketomalonate is heated at 110° C. for 18 hours. The mixture is purified by column chromatography (silica gel, mobile phase:methylene chloride:methanol=98:2).

Yield: 2 g m.p.: resin c) Ethyl 6-(2-ethylaminopyrimidin-4-yl)-3-oxo-2,3-dihydropyridazine-4-carboxylate A mixture of 2 g of diethyl 2-[2-(2-ethylaminopyrimidin-4-yl)-2-oxo-ethyl]-2-hydroxy-malonate, 485 mg of hydrazine hydrochloride and 20 ml of ethanol is stirred under reflux for 24 hours. After cooling while stirring, the precipitate is filtered off with suction, heated in 4 ml of N-methylpyrrolidinone (NMP) at 130° C. for 3 hours and, after cooling, mixed with 15 ml of n-heptane and stirred. The precipitate is then filtered off with suction and stirred with methylene chloride, again filtered off with suction and dried.

Yield: 660 mg m.p.: 234° C.

d) 6-(2-Ethylaminopyrimidin-4-yl)-3-oxo-2,3-dihydropyridazine-4-carboxylic acid A mixture of 400 mg of ethyl 6-(2-ethylaminopyrimidin-4-yl)-3-oxo-2,3-dihydro-pyridazine-4-carboxylate, 2 ml of THF, 2 ml of water, 2 ml of methanol and 100 mg of lithium hydroxide is stirred at room temperature for 1 hour, and the volatile constituents are removed in vacuo. A pH of 4 is adjusted by dropwise addition of 2N hydrochloric acid, and the precipitate which has formed is filtered off with suction, stirred with 10 ml of isopropanol and filtered off with suction and dried.

Yield: 200 mg m.p.: 322° C.

e) 6-(2-Ethylaminopyrimidin-4-yl)-3-oxo-2,3-dihydropyridazine-4-carboxylic acid (2-amino-4-chlorophenyl)amide A solution of 110 mg of 6-(2-ethylaminopyrimidin-4-yl)-3-oxo-2,3-dihydropyridazine-4-carboxylic acid, 2 ml of DMF and 0.17 ml of triethylamine is mixed with 192 mg of Hatu and stirred at room temperature for 30 minutes. Then 66 mg of 4-chloro-phenylenediamine are added, and the mixture is stirred at room temperature overnight. 5 ml of water are added to the mixture, and the precipitate is briefly stirred and then filtered off with suction and dried.

Yield: 57 mg m.p.: >300° C. (decomp.)

f) 4-(5-Chloro-1H-benzoimidazol-2-yl)-6-(2-ethylaminopyrimidin-4-yl)-2H-pyridazin-3-one 6-(2-Ethylaminopyrimidin-4-yl)-3-oxo-2,3-dihydropyridazine-4-carboxylic acid (2-amino-4-chlorophenyl)amide (50 mg) are stirred in 1 ml of glacial acetic acid at 100° C. for 3 hours. After cooling, the precipitate is filtered off with suction, stirred with aqueous sodium bicarbonate solution and again filtered off with suction, washed with water and dried in vacuo.

Yield: 15 mg m.p. >300° C. (decomp.)

EXAMPLE 5

4-(6-Chloro-1H-benzimidazol-2-yl)-6-pyridin-4-yl-2H-pyridazin-3-one

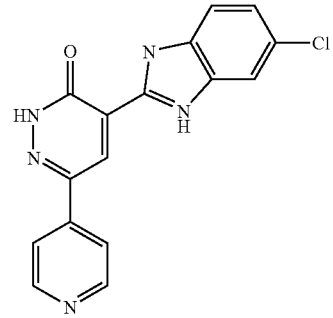

Example 5 is prepared as in example 1.
m.p. >300° C. (decomp.)

EXAMPLE 6

4-(6-Tri-fluoromethyl-1H-benzimidazol-2-yl)-6-pyridin-4-yl-2H-pyridazin-3-one

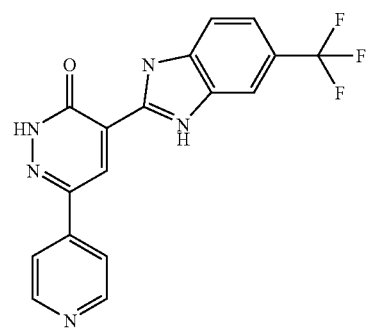

m.p. >300° C. (decomp.)
Example 6 is prepared as in example 1.

EXAMPLE 7

4-(6-Methoxy-1H-benzimidazol-2-yl)-6-pyridin-4-yl-2H-pyridazin-3-one

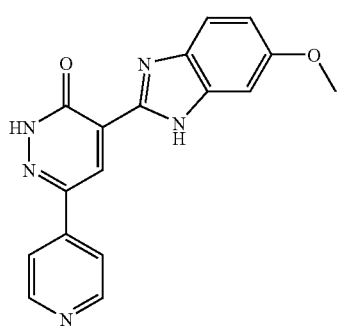

m.p. >300° C. (decomp.)

Example 7 is prepared as in example 1.

EXAMPLE 8

2-(3-Oxo-6-pyridin-4-yl-2,3-dihydropyridazin-4-yl)-1H-benzimidazole-5-carboxylic acid (2-cyclohexylaminoethyl)amide

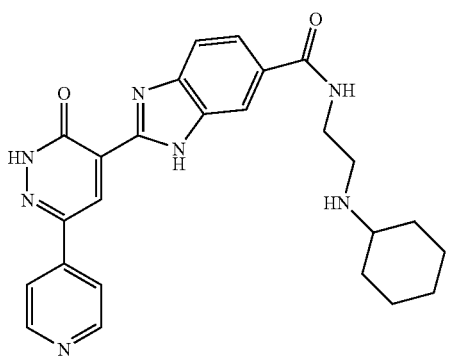

m.p. 271° C.

Example 8 is prepared as in example 3.

EXAMPLE 9

2-(3-Oxo-6-pyridin-4-yl-2,3-dihydropyridazin-4-yl)-1H-benzimidazole-5-carboxylic acid [3-(4-methylpiperazin-1-yl)propyl]amide

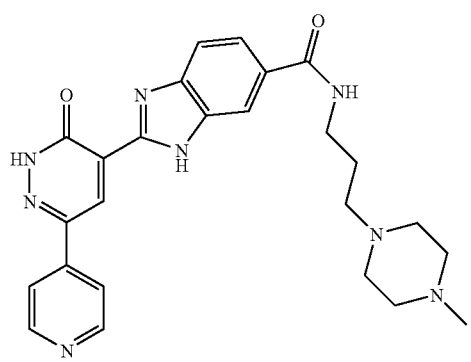

m.p. >30° C. (decomp.)

Example 9 is prepared as in example 3.

EXAMPLE 10

2-(3-Oxo-6-pyridin-4-yl-2,3-dihydropyridazin-4-yl)-1H-benzimidazole-5-carboxylic acid (3-hydroxypropyl)amide m.p. >300° C. (decomp.)

Example 10 is prepared as in example 3.

EXAMPLE 11

4-(5-Chloro-1H-benzimidazol-2-yl)-6-methyl-2H-pyridazin-3-one

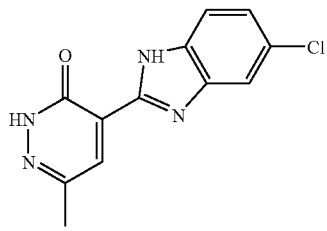

m.p. >300° C. (decomp.)
Example 11 is prepared as in example 1.

EXAMPLE 12
2-(3-Oxo-6-pyridin-4-yl-2,3-dihydropyridazin-4-yl)-1H-benzimidazole-5-carboxylic acid (3-cyclohexylaminopropyl)amide

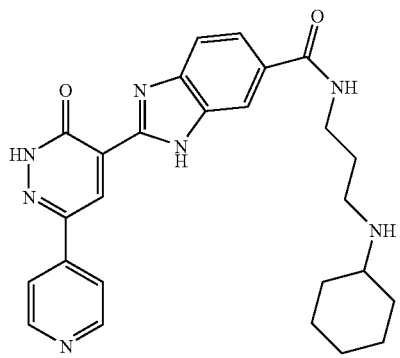

m.p.: resin
Example 12 is prepared as in example 3.

EXAMPLE 13
2-(3-Oxo-6-pyridin-4-yl-2,3-dihydropyridazin-4-yl)-1H-benzimidazole-5-carboxylic acid (3-imidazol-1-yl-propyl)amide

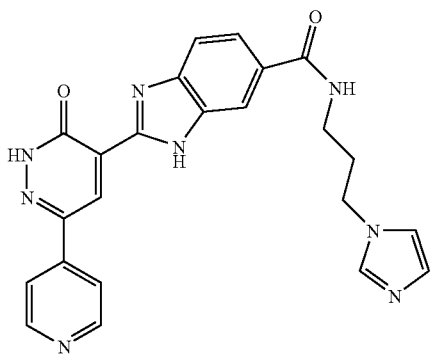

m.p.: resin
Example 13 is prepared as in example 3.

EXAMPLE 14
4-(5-Chloro-1H-benzimidazol-2-yl)-6-(2-methylaminopyrimidin-4-yl)-2H-pyridazin-3-one

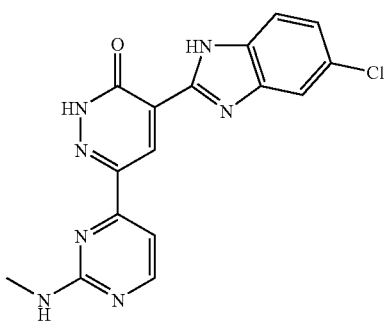

m.p.: >300° C. (decomp.)
Example 14 is prepared as in example 4.

EXAMPLE 15

4-(6-Chloro-1H-benzimidazol-2-yl)-6-(4-hydroxy-3,5-dimethylphenyl)-2H-pyridazin-3-one

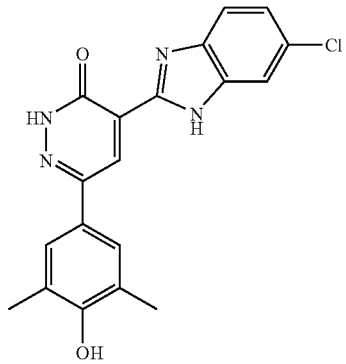

a) Mixture of 6-chloro-3-oxo-2,3-dihydropyridazine-4-carboxylic acid (2-amino-5-chlorophenyl)amide and 6-chloro-3-oxo-2,3-dihydropyridazine-4-carboxylic acid (2-amino-4-chlorophenyl)amide 6-Chloro-3-oxo-2,3-dihydropyridazine-4-carboxylic acid (5 g; 28.6 mmol) is dissolved in a mixture of tetrahydrofuran (250 ml) and DMF (1 ml) and cooled to 8° C. in an ice bath, and oxalyl chloride (19.42 g; 153 mmol) is added dropwise. The mixture is stirred at RT for 2 h, and the solvent is stripped off in vacuo. The residue is dissolved in THF, and the volatile constituents are again stripped off in vacuo at RT. The residue is dissolved in tetrahydrofuran/DMF, and 4-chloro-phenylenediamine (4.08 g; 28.6 mmol) and potassium carbonate (7.92 g; 57.3 mmol) are added. After stirring at RT for 16 hours, the volatile constituents are removed in vacuo, the residue is taken up in water, and the solution is adjusted to pH 2 with 2N hydrochloric acid. The precipitate is filtered off with suction, and the product is purified by column chromatography (silica gel, ethyl acetate/n-heptane, gradient 0-80%).

Yield: 1.0 g.

b) 6-Chloro-4-(6-chloro-1H-benzimidazol-2-yl)-2H-pyridazin-3-one

A mixture of 6-chloro-3-oxo-2,3-dihydropyridazine-4-carboxylic acid (2-amino-5-chlorophenyl)amide and 6-chloro-3-oxo-2,3-dihydropyridazine-4-carboxylic acid (2-amino-4-chlorophenyl)amide (1.0 g; 1.67 mmol) is dissolved in 100 ml of glacial acetic acid and heated at 120° C.

for 90 min. A precipitate separates out on cooling and is filtered off with suction and dried in vacuo at 40° C.

Yield: 315 mg.

c) 6-Chloro-4-[6-chloro-1-(2-trimethylsilanylethoxymethyl)-1H-benzimidazol-2-yl]-2-(2-trimethylsilanylethoxymethyl)-2H-pyridazin-3-one 6-Chloro-4-(6-chloro-1H-benzimidazol-2-yl)-2H-pyridazin-3-one (315 mg; 1.12 mmol) is dissolved in DMF (8.3 ml), cesium carbonate (1.1 g; 3.36 mmol) and (2-chloromethoxyethyl)trimethylsilane (467 mg; 2.8 mmol) are added, and the mixture is stirred at 60° C. for 2 h, cooled and filtered, and the product is purified by column chromatography (RP-HPLC, gradient of 0-100% acetonitrile in water (+0.01% trifluoroacetic acid)).

Yield: 513 mg.

d) 4-[6-Chloro-1-(2-trimethylsilanylethoxymethyl)-1H-benzimidazol-2-yl]-6-(4-hydroxy-3,5-dimethyl phenyl)-2-(2-trimethylsilanylethoxymethyl)-2H-pyridazin-3-one 6-Chloro-4-[6-chloro-1-(2-trimethylsilanylethoxymethyl)-1H-benzimidazol-2-yl]-2-(2-trimethylsilanylethoxymethyl)-2H-pyridazin-3-one (100 mg; 0.185 mmol) and tetrakis(triphenylphosphine) palladium(0) (0.15 equivalents) are dissolved in DME, and argon is passed in for 10 min. 2,6-Dimethyl-4-(4,4,5,5-tetramethyl-1,3,2-dioxaborolan-2-yl)phenol (1 equivalent) and 2M aqueous sodium carbonate solution (2 equivalents) are added and the mixture is heated at 95° C. for 5 hours. The volatile constituents are removed in vacuo, the residue is taken up in DMF, and the product is purified by column chromatography (RP-HPLC, gradient of 0-100% acetonitrile in water (+0.01% trifluoroacetic acid)).

Yield: 64 mg e) 4-(6-Chloro-1H-benzimidazol-2-yl)-6-(4-hydroxy-3,5-dimethylphenyl)-2H-pyridazin-3-one 4-[6-Chloro-1-(2-trimethylsilanylethoxymethyl)-1H-benzimidazol-2-yl]-6-(4-hydroxy-3,5-dimethylphenyl)-2-(2-trimethylsilanylethoxymethyl)-2H-pyridazin-3-one is stirred in dichloromethane:trifluoroacetic acid/1:1 at RT for 30 min. The solvent is stripped off in vacuo, and the residue is dissolved in methanol, and 2M sodium hydroxide solution is added. The solution is stirred at RT for 30 min. After the reaction is complete, water is added and 2N hydrochloric acid is used for acidification. The precipitated product is filtered off with suction and purified by column chromatography (RP-HPLC, gradient of 0-100% acetonitrile in water (+0.01% trifluoroacetic acid)).

Yield: 12.5 mg. MS (ES+) m/z 367 (M+H).

EXAMPLE 16

4-(6-Chloro-1H-benzimidazol-2-yl)-6-(4-hydroxy-3-methoxyphenyl)-2H-pyridazin-3-one

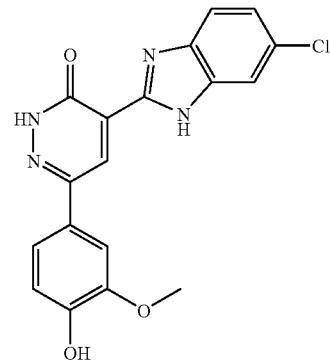

MS (ES+) m/z 369 (M+H).
Example 16 is prepared as in example 15.

EXAMPLE 17

4-(7-Methyl-1H-benzimidazol-2-yl)-6-pyridin-4-yl-2H-pyridazin-3-one

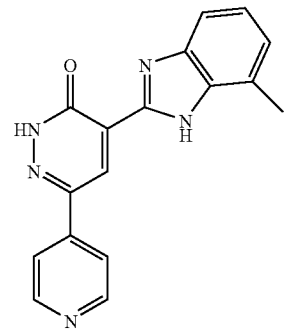

m.p.: >350° C. (decomp.)
Example 17 is prepared as in example 1.

EXAMPLE 18

4-(5,6-Dimethyl-1H-benzimidazol-2-yl)-6-pyridin-4-yl-2H-pyridazin-3-one

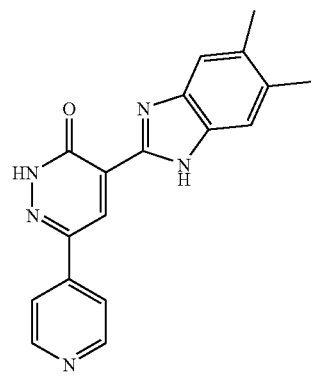

m.p.: >350° C. (decomp.)
Example 18 is prepared as in example 1.

EXAMPLE 19

4-[5-(4-Methylpiperazin-1-yl)-1H-benzimidazol-2-yl]-6-pyridin-4-yl-2H-pyridazin-3-one

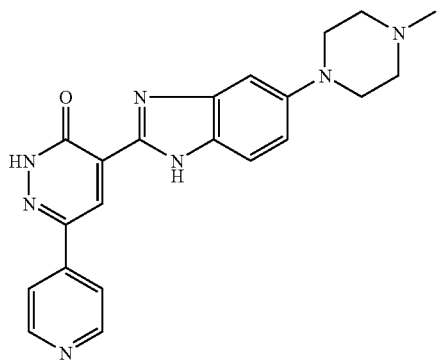

m.p.: >350° C. (decomp.)
Example 19 is prepared as in example 1.

EXAMPLE 20

4-(5-Fluoro-1H-benzimidazol-2-yl)-6-pyridin-4-yl-2H-pyridazin-3-one

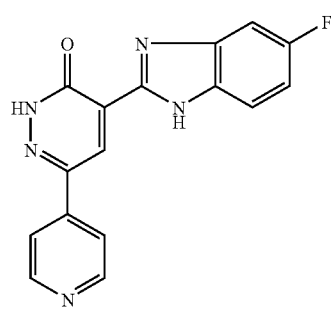

m.p.: >350° C. (decomp.)
Example 20 is prepared as in example 1.

EXAMPLE 21

4-(5-Cyano-1H-benzimidazol-2-yl)-6-pyridin-4-yl-2H-pyridazin-3-one

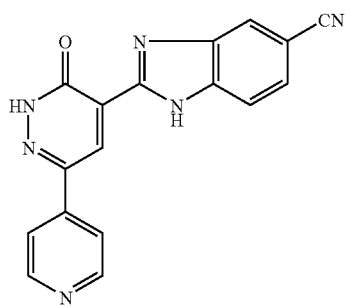

m.p.: >350° C. (decomp.)
Example 21 is prepared as in example 1.

EXAMPLE 22

4-(5-Bromo-1H-benzimidazol-2-yl)-6-pyridin-4-yl-2H-pyridazin-3-one

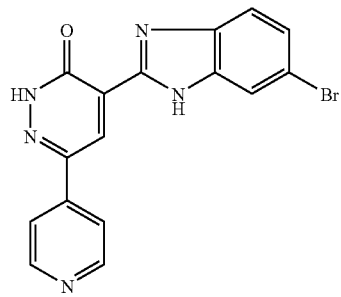

m.p.: >350° C. (decomp.)
Example 22 is prepared as in example 1.

EXAMPLE 23

6-Chloro-4-(3H-imidazo[4,5-c]pyridin-2-yl)-2H-pyridazin-3-one

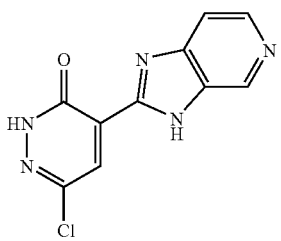

MS (ES+) m/z 248 (M+H).
Example 23 is prepared as in example 1.

EXAMPLE 24

6-(4-Hydroxy-3-methoxyphenyl)-4-(6-tri-fluoromethyl-1H-benzimidazol-2-yl)-2H-pyridazin-3-one

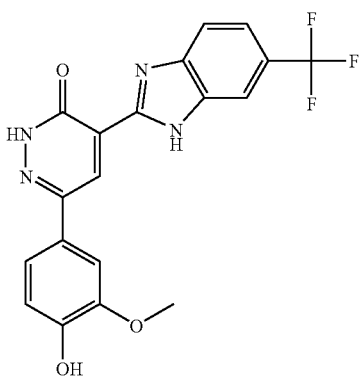

MS (ES+) m/z 403 (M+H).
Example 24 is prepared as in example 15.

EXAMPLE 25

6-(4-Hydroxy-3,5-dimethylphenyl)-4-(6-tri-fluoromethyl-1H-benzimidazol-2-yl)-2H-pyridazin-3-one

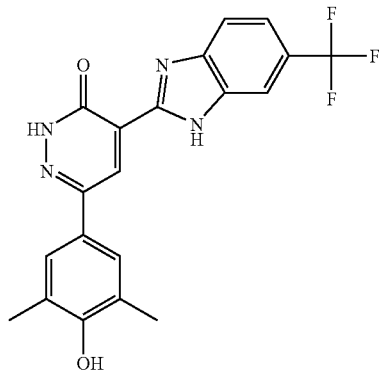

MS (ES+) m/z 401 (M+H).
Example 25 is prepared as in example 15.

EXAMPLE 26

6-(2-Butylaminopyrimidin-4-yl)-4-(6-chloro-1H-benzimidazol-2-yl)-2H-pyridazin-3-one

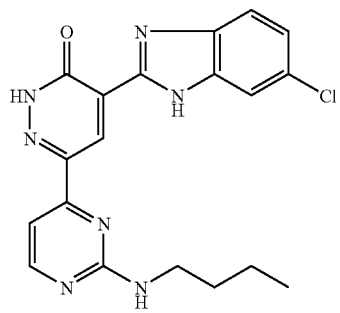

m.p.: 305° C.
Example 26 is prepared as in example 4.

EXAMPLE 27

6-(2-Butylaminopyrimidin-4-yl)-4-(6-tri-fluoromethyl-1H-benzimidazol-2-yl)-2H-pyridazin-3-one

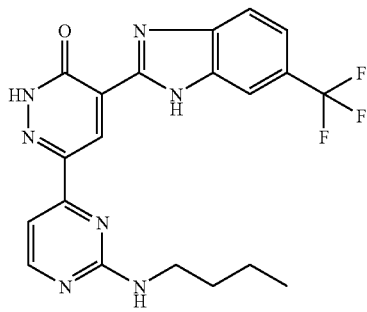

m.p.: 288° C.
Example 27 is prepared as in example 4.

EXAMPLE 28

4-(1H-Benzimidazol-2-yl)-6-pyridin-4-yl-2H-pyridazin-3-one

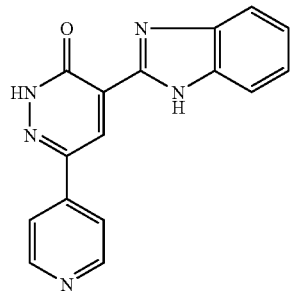

m.p.: >350° C. (decomp.)
Example 28 is prepared as in example 1.

EXAMPLE 29

4-(6-Chloro-1H-benzimidazol-2-yl)-6-[2-((R)-1-phenylethylamino)pyrimidin-4-yl]-2H-pyridazin-3-one

CHRAL

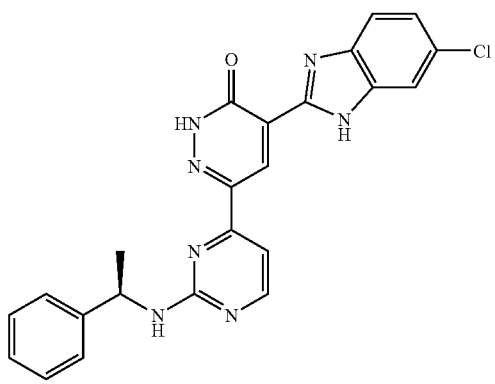

MS (ES+) m/z 444 (M+H)
Example 29 is prepared as in example 4.

EXAMPLE 30

4-(5,6-Dichloro-1H-benzimidazol-2-yl)-6-pyridin-4-yl-2H-pyridazin-3-one; compound with acetic acid

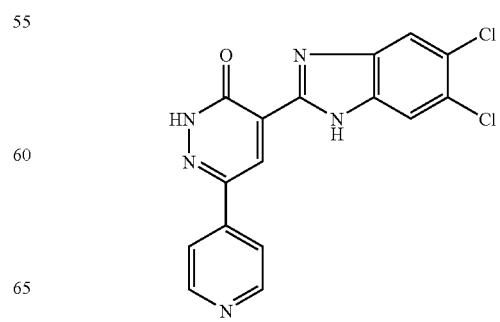

MS (ES+) m/z 358 (M+H)
Example 30 is prepared as in example 1.

EXAMPLE 31

4-(6-Chloro-5-fluoro-1H-benzimidazol-2-yl)-6-pyridin-4-yl-2H-pyridazin-3-one; compound with acetic acid

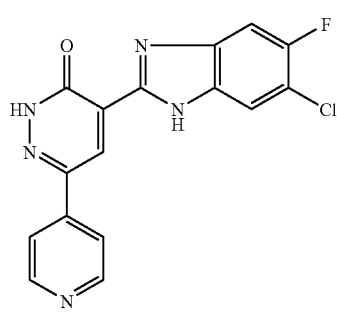

MS (ES+) m/z 342 (M+H)
Example 31 is prepared as in example 1.

EXAMPLE 32

4-(6-Chloro-5-methyl-1H-benzimidazol-2-yl)-6-pyridin-4-yl-2H-pyridazin-3-one; compound with acetic acid

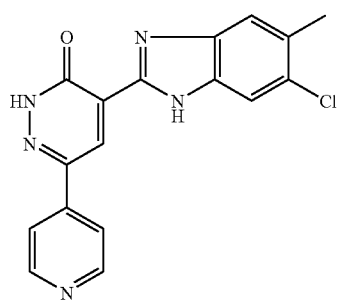

MS (ES+) m/z 338 (M+H)
Example 32 is prepared as in example 1.

EXAMPLE 33

4-(5,7-Difluoro-1H-benzimidazol-2-yl)-6-pyridin-4-yl-2H-pyridazin-3-one; compound with acetic acid

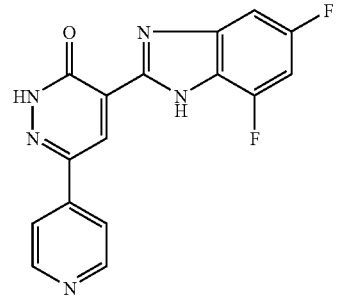

MS (ES+) m/z 326 (M+H)
Example 33 is prepared as in example 1.

EXAMPLE 34

4-(5-Chloro-6-methyl-1H-benzimidazol-2-yl)-6-(4-hydroxy-3-methoxyphenyl)-2H-pyridazin-3-one

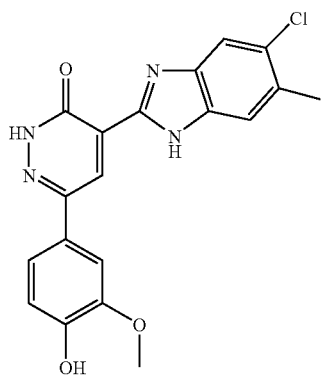

MS (ES+) m/z 383 (M+H)
Example 34 is prepared as in example 15.

EXAMPLE 35

6-[2-(2-Morpholin-4-yl-ethylamino)pyrimidin-4-yl]-4-(6-tri-fluoromethyl-1H-benzimidazol-2-yl)-2H-pyridazin-3-one; compound with trifluoroacetic acid

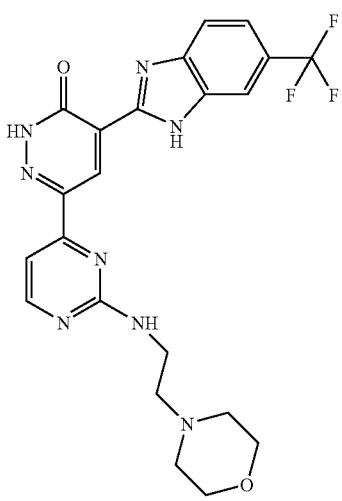

a) 6-Oxo-5-[6-tri-fluoromethyl-1-(2-trimethylsilanylethoxymethyl)-1H-benzimidazol-2-yl]-1-(2-trimethylsilanylethoxymethyl)-1,6-dihydropyridazine-3-boronic acid 6-Chloro-4-[6-trifluormethyl-1-(2-trimethylsilanylethoxymethyl)-1H-benzimidazol-2-yl]-2-(2-trimethylsilanylethoxymethyl)-2H-pyridazin-3-one (prepared in analogy to example 15b), bis(pinacolato)diboron, (1,1'-bis(diphenylphosphine)ferrocene)-palladium(II) chloride-dichloromethane complex and potassium acetate are dissolved in DMSO. The solution is degassed with argon and heated at 95° C. for 2.5 hours. The reaction solution is filtered through silica gel, and the latter is washed with dichloromethane. The solvent is removed in a rotary evaporator, and the crude product is purified by RP-HPLC (0-100% acetonitrile in water (+0.01% trifluoroacetic acid)). MS (ES+) m/z 585 (M+H).

b) 6-(2-Chloropyrimidin-4-yl)-4-[6-tri-fluoromethyl-1-(2-trimethylsilanyl-ethoxymethyl)-1H-benzimidazol-2-yl]-2-(2-trimethylsilanylethoxymethyl)-2H-pyridazin-3-one 6-Oxo-5-[6-tri-fluoromethyl-1-(2-trimethylsilanylethoxymethyl)-1H-benzimidazol-2-yl]-1-(2-trimethylsilanylethoxymethyl)-1,6-dihydropyridazine-3-boronic acid, 2,4-di-chloropyrimidine, potassium fluoride and tris(dibenzylideneacetone)dipalladium(0) are dissolved in dry THF and degassed with argon for 10 minutes. Tri-tert-butyl-phosphonium tetrafluoroborate is added, and the reaction mixture is stirred at room temperature for 16 hours. LC-MS analysis shows complete conversion. The solvent is removed in a rotary evaporator, the residue is dissolved in DMF and the crude product is purified by preparative RP-HPLC (0-100% acetonitrile in water (+0.01% trifluoroacetic acid)). MS (ES+) m/z 653 (M+H).

c) 6-[2-(2-Morpholin-4-ylethylamino)pyrimidin-4-yl]-4-[6-tri-fluoromethyl-1-(2-trimethylsilanylethoxymethyl)-1H-benzimidazol-2-yl]-2-(2-trimethyl-silanylethoxymethyl)-2H-pyridazin-3-one 6-(2-Chloropyrimidin-4-yl)-4-[6-tri-fluoromethyl-1-(2-trimethylsilanylethoxymethyl)-1H-benzimidazol-2-yl]-2-(2-trimethylsilanylethoxymethyl)-2H-pyridazin-3-one is suspended in N-(2-aminoethyl)morpholine, and the reaction mixture is heated at 100° C. in a microwave for 20 minutes. The product is filtered through a reversed phase C18 silica gel cartridge and eluted with water/acetonitrile. The product is purified by preparative RP-HPLC (0-100% acetonitrile in water (+0.01% trifluoroacetic acid)). MS (ES+) m/z 747 (M+H).

d) 6-[2-(2-Morpholin-4-ylethylamino)pyrimidin-4-yl]-4-(6-tri-fluoromethyl-1H-benzimidazol-2-yl)-2H-pyridazin-3-one 6-[2-(2-Morpholin-4-ylethylamino)pyrimidin-4-yl]-4-[6-tri-fluoromethyl-1-(2-trimethyl-silanylethoxymethyl)-1H-benzimidazol-2-yl]-2-(2-trimethylsilanylethoxymethyl)-2H-pyridazin-3-one was reacted in analogy to example 15. MS (ES+) m/z 487 (M+H). NMR (500 MHz; DMSO-d6) 14.25 (s, 1H), 9.25 (s, 1H), 8.51 (d, 1H), 8.11 (s, 1H), 7.95 (d, 1H), 7.61 (d, 1H), 7.35 (d, 1H), 4.02 (brs), 3.75 (brs), 3.40 (brs).

EXAMPLE 36

4-(5,6-Dichloro-1H-benzimidazol-2-yl)-6-(4-hydroxy-3-methoxyphenyl)-2H-pyridazin-3-one

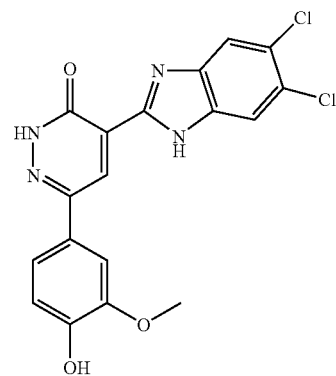

MS (ES+) m/z 403 (M+H)
Example 36 is prepared as in example 15.

EXAMPLE 37

2-[6-(4-Hydroxy-3-methoxyphenyl)-3-oxo-2,3-dihydropyridazin-4-yl]-3H-benzimidazole-5-carboxylic acid

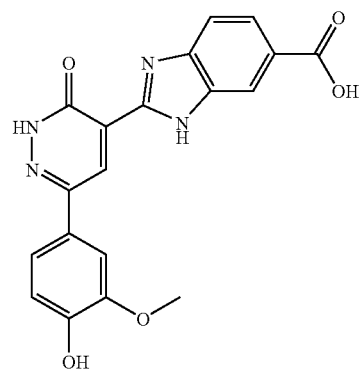

MS (ES+) m/z 379 (M+H)
Example 37 is prepared as in example 15.

EXAMPLE 38

4-(3H-imidazol[4,5-c]pyridin-2-yl)-6-pyridin-4-yl-2H-pyridazin-3-one

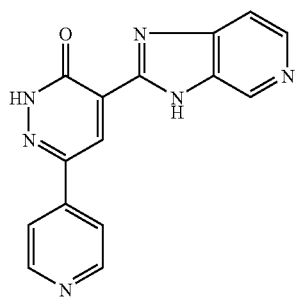

MS (ES+) m/z 291 (M+H)
Example 38 is prepared as in example 1.

EXAMPLE 39
6-[6-Methyl-2-(2-morpholin-4-yl-ethylamino)pyrimidin-4-yl]-4-(6-tri-fluoromethyl-1H-benzimidazol-2-yl)-2H-pyridazin-3-one

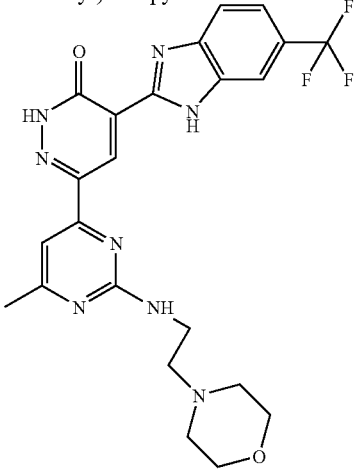

MS (ES+) m/z 501 (M+H)
Example 39 is prepared in analogy to example 35.

EXAMPLE 40
4-(6-Chloro-1H-benzimidazol-2-yl)-6-(2-methylsulfanylpyrimidin-4-yl)-2H-pyridazin-3-one

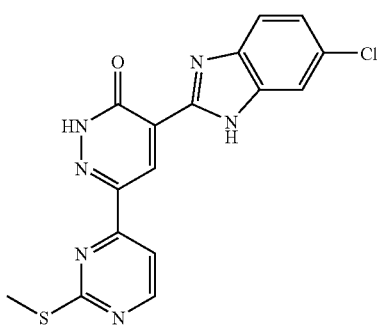

MS (ES+) m/z 371 (M+H)
Example 40 is prepared as in example 4.

EXAMPLE 41
6-(4-Hydroxy-3,5-dimethylphenyl)-4-(7-methyl-1H-benzimidazol-2-yl)-2H-pyridazin-3-one

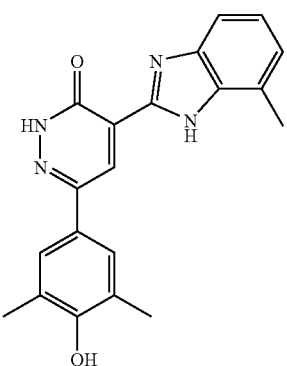

a) 6-Chloro-3-methoxypyridazine-4-carbaldehyde n-Butyllithium is added dropwise at −75° C. to a solution of 2,2,6,6-tetramethyl-piperidine in THF. The solution is stirred at 0° C. for 30 minutes. After cooling to −75° C., a solution, precooled to −75° C., of 3-chloro-6-methoxypyridazine in THF is added dropwise. The reaction is stirred at −75° C. for 30 minutes. Subsequently, DMF precooled to −75° C. is added dropwise, and the mixture is stirred at −75° C. for a further 90 minutes. A mixture of conc. aqueous HCl (5 ml), ethanol (20 ml) and THF (25 ml), is added to the reaction mixture, which is warmed to room temperature, and saturated aqueous NaHCO$_3$ solution is slowly added. THF is removed in a rotary evaporator, and the aqueous phase is extracted three times with dichloromethane. The combined organic phases are dried with MgSO4 and filtered, and the solvent is removed in a rotary evaporator. The residue is purified on silica gel (eluent ethyl acetate in heptane). MS (Cl+) m/z 172 (M+).

b) 2-(6-Chloro-3-methoxypyridazin-4-yl)-7-methyl-1H-benzimidazole

6-Chloro-3-methoxypyridazine-4-carbaldehyde is dissolved in DMF, und 2,3-diaminotoluene is added. The reaction solution is heated at 120° C. in a microwave for 30 minutes. The crude product is purified on silica gel (eluent ethyl acetate in heptane). MS (ES+) m/z 275 (M+H).

c) 4-[6-Methoxy-5-(7-methyl-1H-benzimidazol-2-yl)pyridazin-3-yl]-2,6-dimethylphenol 2-(6-Chloro-3-methoxypyridazin-4-yl)-7-methyl-1H-benzimidazole is reacted in analogy to example 15c) with 2,6-dimethylphenol-4-boronic acid pinacol ester. MS (ES+) m/z 361 (M+H).

d) 6-(4-Hydroxy-3,5-dimethylphenyl)-4-(7-methyl-1H-benzimidazol-2-yl)-2H-pyridazin-3-one 4-[6-Methoxy-5-(7-methyl-1H-benzimidazol-2-yl)-pyridazin-3-yl]-2,6-dimethylphenol is reacted in analogy to example 15e). Purification takes place by preparative RP-HPLC (gradient 0-100% acetonitrile in water (+0.01% trifluoroacetic acid). MS (ES+) m/z 347 (M+H). NMR(500 MHz; DMSO-d6) 13.83 (s, 1H), 8.77 (s, 1H), 8.75 (brs, 1H), 7.65 (d, 1H), 7.54 (s, 2H), 7.26 (t, 1H), 7.17 (m, 1H), 2.65 (s, 3H), 2.27 (s, 6H).

EXAMPLE 42

4-[6-(4-Methylpiperazin-1-ylmethyl)-1H-benzimidazol-2-yl]-6-pyridin-4-yl-2H-pyridazin-3-one

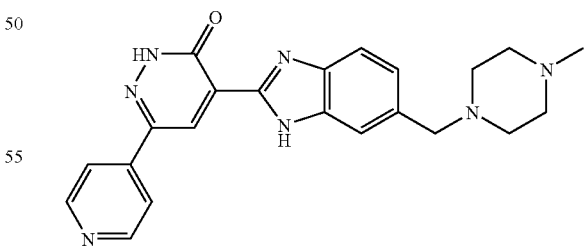

a) 6-Chloro-4-(6-methoxycarbonyl-1-(2-trimethylsilanylethoxymethyl)-1H-benzimidazol-2-yl]-2-(2-trimethylsilanylethoxymethyl)-2H-pyridazin-3-one The compound is prepared in analogy to example 15c) starting from 6-chloro-3-oxo-2,3-dihydro-pyridazine-4-carboxylic acid and methyl 3,4-diaminobenzoate.

b) 6-Chloro-4-(6-formyl-1-(2-trimethylsilanylethoxymethyl)-1H-benz-imidazol-2-yl]-2-(2-trimethylsilanylethoxymethyl)-2H-pyridazin-3-one 6-Chloro-4-(6-methoxycarbonyl-1-(2-trimethylsilanylethoxymethyl)-1H-benzimidazol-2-yl]-2-(2-trimethylsilanylethoxymethyl)-2H-pyridazin-3-one (3.0 g, 5.3 mmol) is dissolved in dichloromethane, and the solution is cooled to 0° C. 15% DIBA1H in toluene is added dropwise, and the reaction mixture is stirred at room temperature for 1 hour. A further 15% DIBA1H in toluene is then added dropwise at 0° C. and stirred at room temperature for 1 hour. Manganese(IV) oxide is then added directly and the reaction solution is heated to reflux for 3 hours. Additional manganese oxide is added every 3 hours until the conversion is complete according to LC-MS. The reaction solution is filtered through kieselguhr, the residue is washed several times with dichloromethane, and the solvent is removed in a rotary evaporator.

MS (ES+) m/z 565 (M+H).

c) 6-Chloro-4-(6-(4-methylpiperazin-1-ylmethyl)-1-(2-trimethylsilanyl-ethoxymethyl)-1H-benzimidazol-2-yl]-2-(2-trimethylsilanylethoxymethyl)-2H-pyridazin-3-one 6-Chloro-4-(6-formyl-1-(2-trimethylsilanylethoxymethyl)-1H-benzimidazol-2-yl]-2-(2-trimethylsilanylethoxymethyl)-2H-pyridazin-3-one is dissolved in dichloro-methane. 4-Methylpiperazine and acetic acid are added. After 15 minutes, sodium triacetoxyborohydride is added in several portions over the course of 3 hours. After conversion is complete, saturated aqueous $NaHCO_3$ solution is added and the reaction solution is stirred until no further $CO_2$ evolution is observed. It is diluted with dichloromethane, and the aqueous phase is extracted with dichloromethane. The combined organic phases are dried with $MgSO_4$, and the solvent is removed in a rotary evaporator.

MS (ES+) m/z 535 (M+H).

d) 4-[6-(4-Methylpiperazin-1-yl methyl)-1-(2-trimethylsilanylethoxymethyl)-1H-benzimidazol-2-yl]-6-pyridin-4-yl-]-2-(2-trimethylsilanylethoxymethyl)-2H-pyridazin-3-one 6-Chloro-4-(6-(4-methylpiperazin-1-ylmethyl)-1-(2-trimethylsilanylethoxymethyl)-1H-benzimidazol-2-yl]-2-(2-trimethylsilanylethoxymethyl)-2H-pyridazin-3-one is reacted in analogy to example 15d) with pyridine-4-boronic acid pinacol ester. The crude product obtained by removing the solvent is employed directly in the next step.

MS (ES+) m/z 661 (M+H).

e) 4-[6-(4-Methylpiperazin-1-ylmethyl)-1H-benzimidazol-2-yl]-6-pyridin-4-yl-2H-pyridazin-3-one Crude 4-[6-(4-methylpiperazin-1-ylmethyl)-1-(2-trimethylsilanylethoxymethyl)-1H-benzimidazol-2-yl]-6-pyridin-4-yl]-2-(2-trimethylsilanylethoxymethyl)-2H-pyridazin-3-one is reacted in analogy to example 15e).

MS (ES+) m/z 402.27 (M+H).

EXAMPLE 43

6-(4-Hydroxy-3,5-dimethylphenyl)-4-[6-(4-methylpiperazin-1-ylmethyl)-1H-benzimidazol-2-yl]-2H-pyridazin-3-one

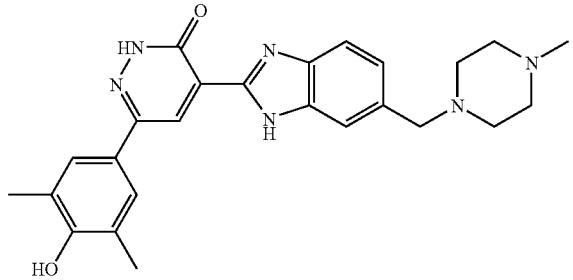

MS (ES+) m/z 445 (M+H).
Example 43 is prepared in accordance with example 42.

EXAMPLE 44

2-[6-(4-Hydroxy-3,5-dimethylphenyl)-3-oxo-2,3-dihydropyridazin-4-yl]-3H-benzimidazole-5-carboxylic acid

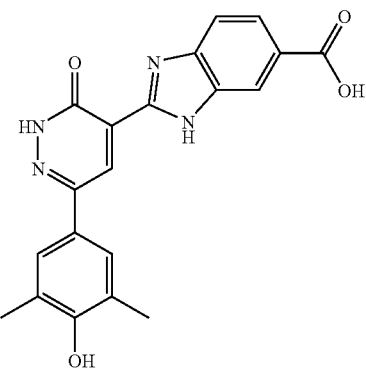

MS (ES+) m/z 377 (M+H).
Example 44 is prepared in accordance with example 15.

EXAMPLE 45

4-(1H-Benzimidazol-2-yl)-6-chlor-2H-pyridazin-3-one

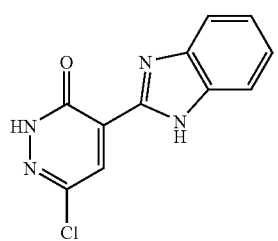

a) 6-Chloro-3-oxo-2,3-dihydropyridazine-4-carboxylic acid (2-amino-phenyl)amide 30.5 g of 6-chloro-3-oxo-2,3-dihydropyridazine-4-carboxylic acid, 18 g of ortho-phenylenediamine and 2 g of DMAP are dissolved in 800 ml of DMF, at room temperature 32.2 g of 1-ethyl-3-(3-dimethylaminopropyl)carbodiimide hydrochloride are added, and the resulting solution is stirred at room temperature for 4 hours. For workup, the solvent is distilled off and the residue is suspended in water at 70° C. The precipitate is filtered off, washed several times with water and then dried in vacuo.

MS (ES+) m/z 265 (M+H).

b) 4-(1H-Benzimidazol-2-yl)-6-chloro-2H-pyridazin-3-one

A solution of 26.4 g of 6-chloro-3-oxo-2,3-dihydropyridazine-4-carboxylic acid (2-aminophenyl)amide in 500 ml of acetic acid is stirred at 110° C. for 2.5 hours and then the solvent is distilled off. The crude product obtained in this way is employed without further purification.

MS (ES+) m/z 247 (M+H).

EXAMPLE 46

4-(1H-Benzimidazol-2-yl)-6-thiophen-3-yl-2H-pyridazin-3-one

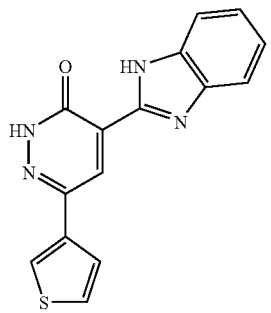

a) 6-Chloro-2-(2-trimethylsilanylethoxymethyl)-4-[1-(2-trimethylsilanyl-ethoxymethyl)-1H-benzimidazol-2-yl]-2H-pyridazin-3-one 6-Chloro-4-(1H-benzimidazol-2-yl)-2H-pyridazin-3-one (7 g; 28.4 mmol, example 45) is dissolved in DMF (175 ml), cesium carbonate (37 g; 113 mmol) and (2-chloromethoxyethyl)trimethylsilane (15.8 g; 85 mmol) are added, and the mixture is stirred at room temperature for 12 h. For workup, it is diluted with 800 ml of water and extracted several times with ethyl acetate, and the organic phases are washed with saturated NaCl solution and dried over magnesium sulphate. After the solvent has been evaporated off, the crude product is purified by silica gel chromatography.

Yield: 10.5 g.

b) 6-Thiophen-3-yl-2-(2-trimethylsilanylethoxymethyl)-4-[1-(2-trimethylsilanyl-ethoxymethyl)-1H-benzimidazol-2-yl]-2H-pyridazin-3-one 44 mg of 6-chloro-2-(2-trimethylsilanylethoxymethyl)-4-[1-(2-trimethylsilanyl-ethoxymethyl)-1H-benzimidazol-2-yl]-2H-pyridazin-3-one, 14 mg of thiophene-3-boronic acid and 36 mg of potassium carbonate are dissolved 1.5 ml of a 1:2 mixture of water and dimethoxyethane, and argon is passed through the solution for degassing. Addition of 7 mg of (1,1'-bis(diphenylphosphine) -ferrocene)palladium(II) chloride-dichloromethane complex is followed by stirring at 85° C. for 4 hours. For workup, it is diluted with water and extracted several times with ethyl acetate. The combined organic phases are dried using a silica gel cartridge, and the solvent is distilled off. The crude product is purified by silica gel chromatography (n-heptane/ethyl acetate).

Yield: 32 mg c) 4-(1H-Benzimidazol-2-yl)-6-thiophen-3-yl-2H-pyridazin-3-one 30 mg of 6-thiophen-3-yl-2-(2-trimethylsilanylethoxymethyl)-4-[1-(2-trimethylsilanyl -ethoxymethyl)-1H-benzimidazol-2-yl]-2H-pyridazin-3-one is dissolved in a mixture of dichloromethane (1 ml) and trifluoroacetic acid (1 ml), 18 μl of ethanedithiol are added, and the resulting solution is stirred at room temperature for 18 hours. After the solvent has been distilled off, the crude product is purified by preparative RP-HPLC (0-100% acetonitrile (+0.05% formic acid) in water (+0.05% formic acid)).

Yield: 32 mg MS (ES+) m/z 295 (M+H).

EXAMPLE 47

4-(1H-Benzimidazol-2-yl)-6-thiazol-2-yl-2H-pyridazin-3-one

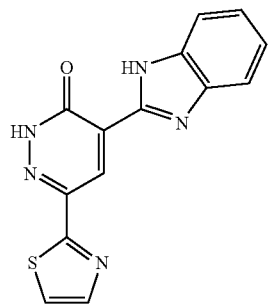

MS (ES+) m/z 296 (M+H).

Example 47 is prepared in accordance with example 46.

EXAMPLE 48

4-(1H-Benzimidazol-2-yl)-6-cyclopropyl-2H-pyridazin-3-one

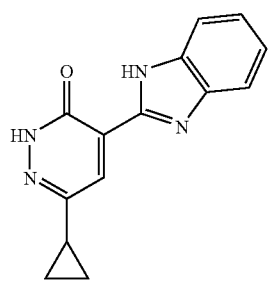

MS (ES+) m/z 253 (M+H).
Example 48 is prepared in accordance with example 46.

EXAMPLE 49

4-[6-(4-Methylpiperazin-1-ylmethyl)-1H-benzimidazol-2-yl]-6-thiophen-3-yl-2H-pyridazin-3-one

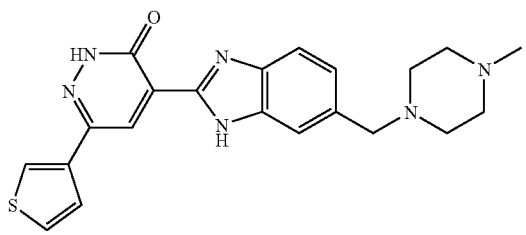

MS (ES+) m/z 407 (M+H).
Example 49 is prepared in accordance with example 42.

EXAMPLE 50

4-(1H-Benzimidazol-2-yl)-6-(1-methyl-6-oxo-1,6-dihydropyridin-3-yl)-2H-pyridazin-3-one

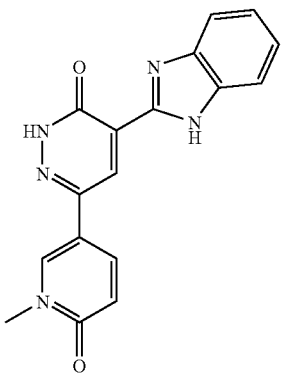

MS (ES+) m/z 320 (M+H).
Example 50 is prepared in accordance with example 46.

EXAMPLE 51

4-(1H-Benzimidazol-2-yl)-6-(3-fluoropyridin-4-yl)-2H-pyridazin-3-one

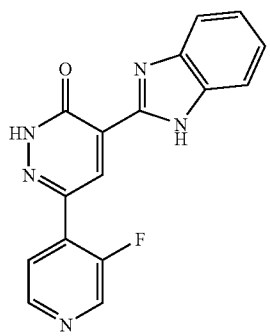

MS (ES+) m/z 308 (M+H).
Example 51 is prepared in accordance with example 46.

EXAMPLE 52

2-[6-(2-Methylsulfanylpyrimidin-4-yl)-3-oxo-2,3-dihydropyridazin-4-yl]-3H-benzimidazole-5-carboxylic acid

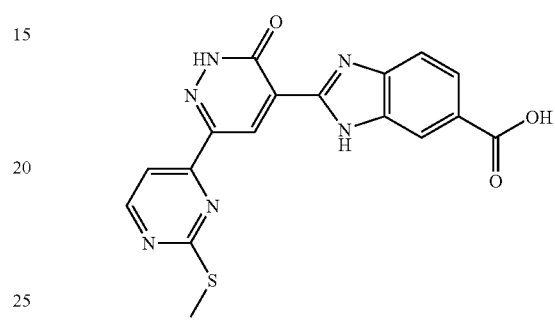

The compound is prepared in analogy to example 15. A Stille coupling is carried out instead of the Suzuki coupling. This entails dissolving 6-chloro-4-[5-methoxycarbonyl-1-(2-trimethylsilanylethoxymethyl)-1H-benzimidazol-2-yl]-2-(2-trimethylsilanylethoxymethyl)-2H-pyridazin-3-one, 2-methylsulfanyl-4-tributyl-stannylpyrimidine, tetraethylammonium chloride and bis(triphenyl-phosphine)palladium (II) chloride in DMF under argon and heating at 80° C. for 6 hours. After cooling to room temperature, 30% aqueous potassium fluoride solution is added, and the mixture is stirred for 30 minutes. Extraction with ethyl acetate and drying on a drying column afford after purification on SiO₂ 4-[5-methoxycarbonyl-1-(2-trimethylsilanylethoxymethyl)-1H-benzimidazol-2-yl]-6-(2-methylsulfanylpyrimidin-4-yl)-2-(2-trimethylsilanylethoxymethyl)-2H-pyridazin-3-one which is reacted further in analogy to example 15.

MS (ES+) m/z 381 (M+H).

EXAMPLE 53

4-[6-(4-Methylpiperazin-1-ylmethyl)-1H-benzimidazol-2-yl]-6-phenyl-2H-pyridazin-3-one

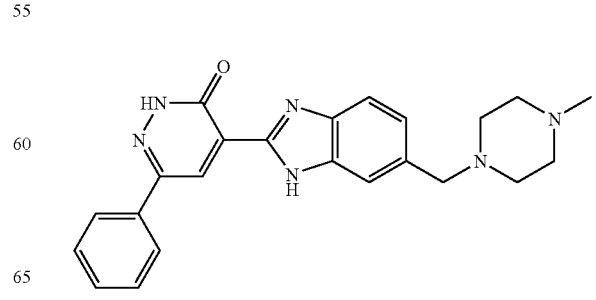

MS (ES+) m/z 401 (M+H).

Example 53 is prepared in accordance with example 42.

EXAMPLE 54

6-(3-Hydroxyphenyl)-4-[6-(4-methylpiperazin-1-ylmethyl)-1H-benzimidazol-2-yl]-2H-pyridazin-3-one

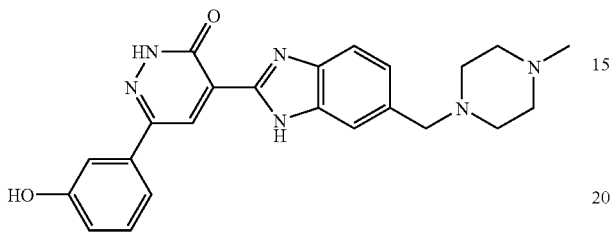

MS (ES+) m/z 417 (M+H).

Example 54 is prepared in accordance with example 42.

EXAMPLE 55

4-(1H-Benzimidazol-2-yl)-6-[2-(2-morpholin-4-yl-ethylamino)pyrimidin-4-yl]-2H-pyridazin-3-one

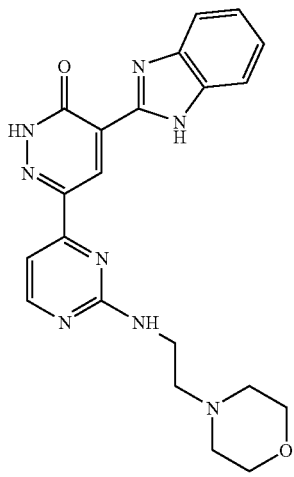

a) 6-Oxo-1-(2-trimethylsilanylethoxymethyl)-5-[1-(2-trimethylsilanyl-ethoxymethyl)-1H-benzimidazol-2-yl]-1,6-dihydropyridazine-3-boronic acid 4 g of 6-chloro-2-(2-trimethylsilanylethoxymethyl)-4-[1-(2-trimethylsilanylethoxy-methyl)-1H-benzimidazol-2-yl]-2H-pyridazin-3-one (example 46), 4.1 g of bis(pinacolato) diboron, 0.19 g of (1,1'-bis(diphenylphosphine)-ferrocene) palladium(II) chloride-dichloromethane complex and 2.3 g of potassium acetate are dissolved in 60 ml of DMSO. The solution is degassed with argon and heated at 95° C. for 2.5 hours. For workup, 600 ml of water are added, the mixture is extracted several times with dichloromethane and the organic phase is washed with saturated sodium chloride solution and dried using a phase separator cartridge. After the solvent has been distilled off, the crude product is purified by preparative RP-HPLC (0-100% acetonitrile in water (+0.01% trifluoroacetic acid)).

Yield: 3.75 g b) 6-(2-Chloropyrimidin-4-yl)-2-(2-trimethylsilanylethoxymethyl)-4-[1-(2-trimethylsilanylethoxymethyl)-1H-benzimidazol-2-yl]-2H-pyridazin-3-one 1.32 g of 6-oxo-1-(2-trimethylsilanylethoxymethyl)-5-[1-(2-trimethylsilanylethoxy-methyl)-1H-benzimidazol-2-yl]-1,6-dihydropyridazine-3-boronic acid, 583 mg of 2,4-dichloropyrimidine and 3,3 g of cesium carbonate are dissolved in 17 ml of a 1:4 mixture of water and dioxane, and argon is passed through the solution for degassing. After addition of 125 mg of (1,1'-bis(diphenyl-phosphine)ferrocene)palladium(II) chloride-dichloromethane complex, the solution is stirred at 97° C. for 3 hours. For workup, it is diluted with 50 ml of water and extracted several times with ethyl acetate. The combined organic phases are dried using a silica gel cartridge, and the solvent is distilled off. The crude product is purified by preparative RP-HPLC (0-100% acetonitrile in water (+0.01% trifluoroacetic acid)).

Yield: 1 g c) 6-[2-(2-Morpholin-4-ylethylamino)pyrimidin-4-yl]-2-(2-trimethylsilanyl-ethoxymethyl)-4-[1-(2-trimethylsilanylethoxymethyl)-1H-benzimidazol-2-yl]-2H-pyridazin-3-one 100 mg of 6-(2-chloropyrimidin-4-yl)-2-(2-trimethylsilanylethoxymethyl)-4-[1-(2-trimethylsilanylethoxymethyl)-1H-benzimidazol-2-yl]-2H-pyridazin-3-one are suspended in 0.5 ml of N-(2-aminoethyl)morpholine, and the reaction mixture is heated at 100° C. in a microwave for 20 minutes. The product is purified by preparative RP-HPLC (0-100% acetonitrile (+0.05% formic acid) in water (+0.05% formic acid)).

Yield: 91 mg d) 4-(1H-Benzimidazol-2-yl)-6-[2-(2-morpholin-4-ylethylamino)pyrimidin-4-yl]-2H-pyridazin-3-one 88 mg of 6-[2-(2-morpholin-4-ylethylamino)pyrimidin-4-yl]-2-(2-trimethylsilanyl-ethoxymethyl)-4-[1-(2-trimethylsilanylethoxymethyl)-1H-benzimidazol-2-yl]-2H-pyridazin-3-one are dissolved in 2 ml of a 1:1 mixture of dichloromethane and trifluoroacetic acid, and the mixture is stirred at room temperature for 2 hours. The volatile components are then distilled off, the residue is dissolved in 1 ml of methanol, and 1 ml of a two molar aqueous sodium hydroxide solution is added. The solution is stirred at room temperature for 12 hours and then put directly onto the preparative RP-HPLC (0-100% acetonitrile (+0.05% formic acid) in water (+0.05% formic acid)) to isolate the product.

Yield: 43 mg MS (ES+) m/z 419 (M+H).

EXAMPLE 56

4-(1H-Benzimidazol-2-yl)-6-[1-(2-morpholin-4-ylethyl)-6-oxo-1,6-dihydro-pyridin-3-yl]-2H-pyridazin-3-one

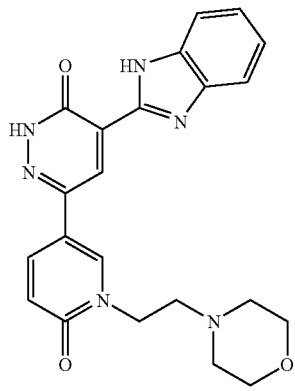

MS (ES+) m/z 419 (M+H).

Example 56 is prepared in accordance with example 55d.

EXAMPLE 57

6-(3-Amino-1-methyl-1H-pyrazol-4-yl)-4-(1H-benzimidazol-2-yl)-2H-pyridazin-3-one

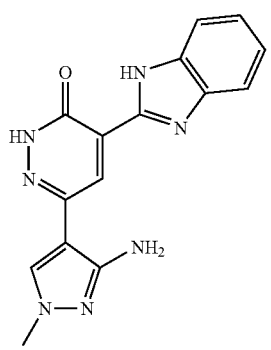

MS (ES+) m/z 308 (M+H).

Example 57 is synthesized in accordance with example 55d.

EXAMPLE 58

4-(1H-Benzimidazol-2-yl)-6-(2-cyclopropylaminopyrimidin-4-yl)-2H-pyridazin-3-one

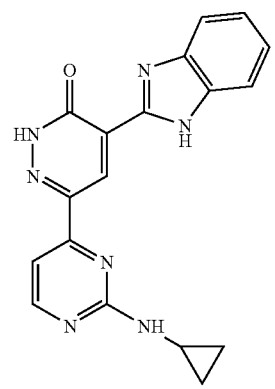

MS (ES+) m/z 346 (M+H).

Example 58 is synthesized in accordance with example 55.

EXAMPLE 59

4-(1H-Benzimidazol-2-yl)-6-[2-(2-hydroxy-1,1-dimethylethylamino)pyrimidin-4-yl]-2H-pyridazin-3-one

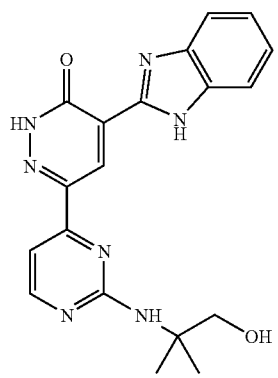

MS (ES+) m/z 378 (M+H).
Example 59 is synthesized in accordance with example 55.

EXAMPLE 60

4-(1H-Benzimidazol-2-yl)-6-(2-dimethylaminopyrimidin-4-yl)-2H-pyridazin-3-one

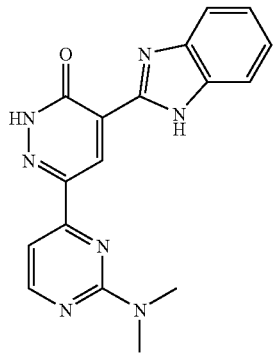

MS (ES+) m/z 334 (M+H).
Example 60 is synthesized in accordance with example 55.

EXAMPLE 61

4-(1H-Benzimidazol-2-yl)-6-[2-(2-methoxyethylamino)pyrimidin-4-yl]-2H-pyridazin-3-one

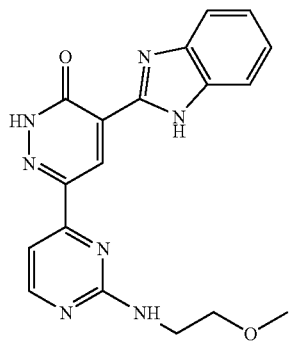

MS (ES+) m/z 364 (M+H).
Example 61 is synthesized in accordance with example 55.

EXAMPLE 62

{4-[5-(1H-Benzimidazol-2-yl)-6-oxo-1,6-dihydropyridazin-3-yl]pyrimidin-2-ylamino}acetic acid

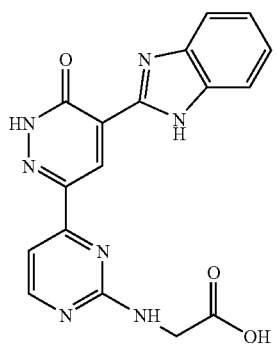

MS (ES+) m/z 364 (M+H).
Example 62 is synthesized in accordance with example 55.

EXAMPLE 63

3-{4-[5-(1H-Benzimidazol-2-yl)-6-oxo-1,6-dihydropyridazin-3-yl]pyrimidin-2-ylamino}propionic acid

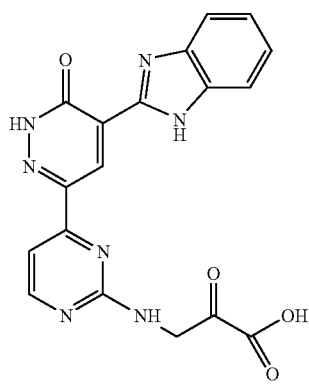

MS (ES+) m/z 378 (M+H).

Example 63 is synthesized in accordance with example 55.

EXAMPLE 64

4-(1H-Benzimidazol-2-yl)-6-morpholin-4-yl-2H-pyridazin-3-one

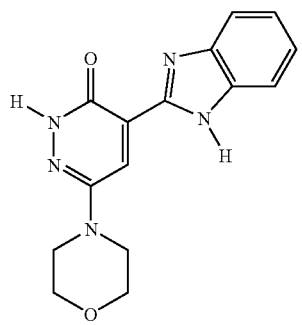

a) 6-Morpholin-4-yl-2-(2-trimethylsilanylethoxymethyl)-4-[1-(2-trimethyl-silanylethoxymethyl)-1H-benzoimidazol-2-yl]-2H-pyridazin-3-one 120 mg of 6-chloro-2-(2-trimethysilanylethoxymethyl)-4-[1-(2-trimethylsilanyl-ethoxymethyl)-1H-benzimidazol-2-yl]-2H-pyridazin-3-one are dissolved in 0.5 ml of morpholine and heated in a microwave at 150° C. for 1 hour and at 170° C. for 1 hour. The final product is isolated by RP-HPLC (water (0.05% HCOOH), acetonitrile (0.05% HCOOH)).

Yield: 76 mg b) 4-(1H-Benzimidazol-2-yl)-6-morpholin-4-yl-2H-pyridazin-3-one

This compound is prepared in accordance with 55d from 6-morpholin-4-yl-2-(2-trimethylsilanylethoxymethyl)-4-[1-(2-trimethylsilanylethoxymethyl)-1H-benzoimidazol-2-yl]-2H-pyridazin-3-one.
Yield: 41.5 mg MS (ES+) m/z 298 (M+H)

EXAMPLE 65

4-(1H-Benzimidazol-2-yl)-6-[2-methylsulfanyl pyrimidin-4-yl]-2H-pyridazin-3-one

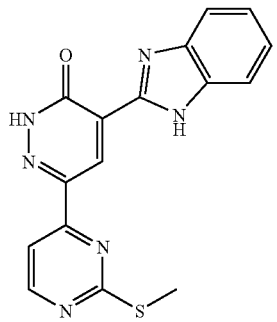

The compound is prepared in analogy to example 15. A Stille coupling is carried out instead of the Suzuki coupling. This entails dissolving 6-chloro-4-[1-(2-trimethylsilanylethoxymethyl)-1H-benzimidazol-2-yl]-2-(2-trimethylsilanylethoxy-methyl)-2H-pyridazin-3-one, 2-methylsulfanyl-4-tributylstannylpyrimidine, tetra-ethylammonium chloride and bis(triphenylphosphine)palladium(II) chloride in DMF under argon and heating at 80° C. for 6 hours. After cooling to room temperature, 30% aqueous potassium fluoride solution is added, and the mixture is stirred for 30 minutes. Extraction with ethyl acetate and drying on a drying column afford after purification on SiO₂ 4-[1-(2-trimethylsilanylethoxymethyl)-1H-benzimidazol-2-yl]-6-(2-methyisulfanylpyrimidin-4-yl)-2-(2-trimethylsilanylethoxymethyl)-2H-pyridazin-3-one which is reacted further in analogy to example 15.
MS (ES+) m/z 337 (M+H).

EXAMPLE 66

6-(4-Hydroxy-3,5-dimethylphenyl)-4-(6-[1,4]oxazepan-4-ylmethyl-1H-benz-imidazol-2-yl)-2H-pyridazin-3-one

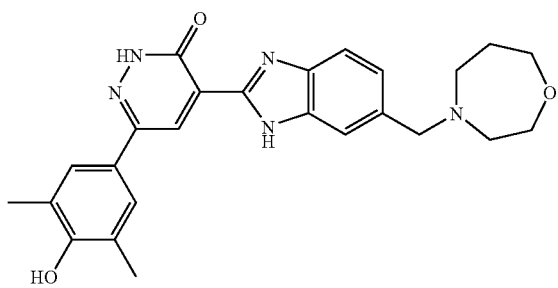

MS (ES+) m/z 446 (M+H).

Example 66 is synthesized in accordance with example 42.

EXAMPLE 67

4-(1H-Benzimidazol-2-yl)-6-(1,5-dimethyl-6-oxo-1,6-dihydropyridin-3-yl)-2-H-pyridazin-3-one

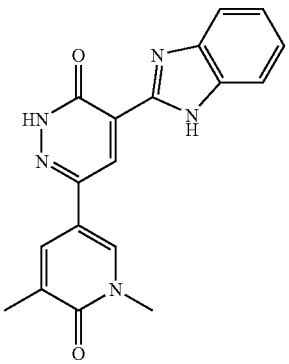

MS (ES+) m/z 334 (M+H).

Example 67 is synthesized in accordance with example 55d.

EXAMPLE 68

4-(1H-Benzimidazol-2-yl)-6-imidazol-1-yl-2H-pyridazin-3-one

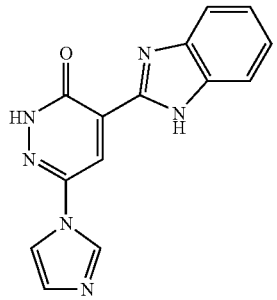

a) 4-[1-(2-Dimethylsilanylethoxymethyl)-1H-benzimidazol-2-yl]-6-imidazol-1-yl-2-(2-trimethylsilanylethoxymethyl)-2H-pyridazin-3-one 100 mg of 6-oxo-1-(2-trimethylsilanylethoxymethyl)-5-[1-(2-trimethylsilanyl-ethoxymethyl)-1H-benzimidazol-2-yl]-1,6-dihydropyridazine-3-boronic acid (example 55), 35.5 mg of copper(II) acetate and 20 mg of imidazole are dissolved in dry pyridine, and the solution is stirred at 80° C. for 3 hours. For workup, it is diluted with 20 ml of water and extracted several times with ethyl acetate, the organic phases are dried using a silica gel cartridge, and the volatile components are distilled off. The crude product is purified by preparative RP-HPLC (0-100% acetonitrile (+0.05% formic acid) in water (+0.05% formic acid)).
Yield: 21 mg b) 4-(1H-Benzimidazol-2-yl)-6-imidazol-1-y-2H-pyridazin-3-one 40 mg of 4-[1-(2-dimethylsilanylethoxymethyl)-1H-benzimidazol-2-yl]-6-imidazol-1-yl-2-(2-trimethylsilanylethoxymethyl)-2H-pyridazin-3-one are dissolved in 2 ml of a 1:1 mixture of dichloromethane and trifluoroacetic acid, and the mixture is stirred at room temperature for 2 hours. The volatile components are then distilled off, the residue is dissolved in 1 ml of methanol, and 1 ml of a two molar aqueous sodium hydroxide solution is added. The solution is stirred at room temperature for 12 hours and then put directly onto the preparative RP-HPLC (0-100% acetonitrile (+0.05% formic acid) in water (+0.05% formic acid)) to isolate the product.
Yield: 19.3 mg MS (ES+) m/z 279 (M+H).

EXAMPLE 69

4-(6-Chloro-3H-imidazo[4,5-b]pyridin-2-yl)-6-(4-hydroxy-3,5-dimethylphenyl)-2H-pyridazin-3-one

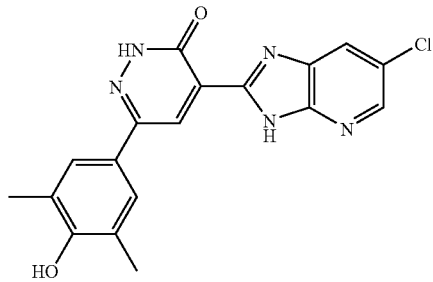

MS (ES+) m/z 368 (M+H).

Example 75 is synthesized in accordance with examples 45 and 15.

EXAMPLE 70

6-Chloro-4-(5-hydroxy-1H-benzimidazol-2-yl)-2H-pyridazin-3-one

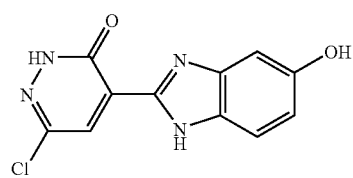

MS (ES+) m/z 263 (M+H).
Example 75 is synthesized in accordance with example 45.

EXAMPLE 71

4-(1H-Benzimidazol-2-yl)-6-pyrazol-1-yl-2H-pyridazin-3-one

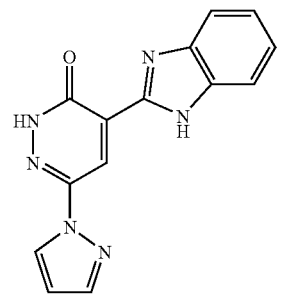

MS (ES+) m/z 279 (M+H).
Example 71 is prepared in accordance with example 68.

EXAMPLE 72

4-(1H-Benzimidazol-2-yl)-6-thiazol-4-yl-2H-pyridazin-3-one

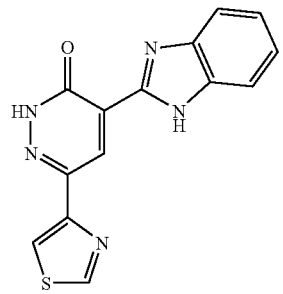

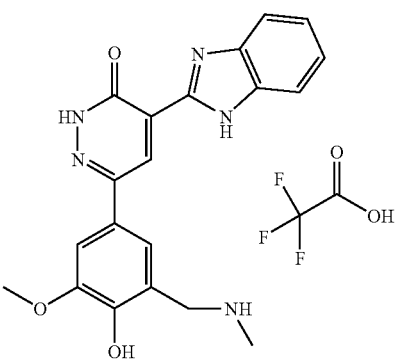

Example 72 is prepared in accordance with example 55d.

EXAMPLE 73

4-(1H-Benzimidazol-2-yl)-6-(4-hydroxy-3-methoxy-5-methylaminomethyl-phenyl)-2H-pyridazin-3-one (a) 5-Bromo-3-methoxy-2-(2-trimethylsilanylethoxymethoxy)benzaldehyde 10 g of 5-bromo-2-hydroxy-3-methoxybenzaldehyde, 23.9 g of potassium carbonate and 12.2 g of (2-chloromethoxyethyl)trimethylsilane is suspended in 500 ml of DMF and stirred at room temperature for 48 hours. The DMF is distilled off in vacuo, the residue is dissolved in ethyl acetate, and the resulting solution is extracted with water. It is then dried over magnesium sulphate and filtered, and the solvent is distilled off. The crude product is purified by silica gel chromatography (heptane/ethyl acetate).
Yield: 15.3 g.

(b) 3-Methoxy-5-(4,4,5,5-tetramethyl-[1,3,2]dioxaborolan-2-yl)-2-(2-trimethylsilanylethoxymethoxy)benzaldehyde 5 g of 5-bromo-3-methoxy-2-(2-trimethylsilanylethoxymethoxy)benzaldehyde, 1.013 g of (1,1'-bis(diphenylphosphino)ferrocene)palladium(II) chloride and 767.3 mg of 1,1'-bis(diphenylphosphino)ferrocene are dissolved in 400 ml of dioxane, and argon is passed through the solution. Then 5.27 g of bis(pinacolato)diboron and 4.075 g of potassium acetate are added, and the mixture is stirred at 80° C. for 16 hours. For workup, the solvent is distilled off, the residue is dissolved in dichloromethane, the solution is filtered and the solvent is distilled off. The crude product is purified by silica gel chromatography (heptane/ethyl acetate).
Yield: 5.47 g.

(c) Methoxy-5-{6-oxo-1-(2-trimethylsilanylethoxymethyl)-5-[1-(2-trimethyl-silanylethoxymethyl)-1H-benzimidazol-2-yl]-1,6-dihydropyridazin-3-yl}-2-(2-trimethylsilanylethoxymethoxy)benzaldehyde This compound is synthesized in accordance with example 15(d) starting from 402 mg of 3-methoxy-5-(4,4,5,5-tetramethyl-[1,3,2]dioxaborolan-2-yl)-2-(2-trimethylsilanylethoxymethoxy)benzaldehyde and 500 mg of 6-chloro-2-(2-trimethylsilanylethoxymethyl)-4-[1-(2-trimethylsilanylethoxymethyl)-1H-benz-imidazol-2-yl]-2H-pyridazin-3-one.
Yield 565 mg. MS (ES+) m/z 753 (M+H).

(d) 6-[3-Methoxy-5-methylaminomethyl-4-(2-trimethylsilanylethoxy-methoxy)phenyl]-2-(2-trimethylsilanylethoxymethyl)-4-[1-(2-trimethylsilanylethoxymethyl)-1H-benzimidazol-2-yl]-2H-pyridazin-3-one 200 mg of methoxy-5-{6-oxo-1-(2-trimethylsilanylethoxymethyl)-5-[1-(2-trimethylsilanylethoxymethyl)-1H-benzimidazol-2-yl]-1,6-dihydropyridazin-3-yl}-2-(2-trimethylsilanylethoxymethoxy)benzaldehyde are dissolved in 4.5 ml of methanol and methylamine (0.146 ml of a THF solution), and 18.4 mg of sodium cyanoborohydride are added, followed by 17 mg of acetic acid. After stirring at room temperature for 16 hours, the volatile components are distilled off and the crude product is employed without further purification for the next reaction.

(e) 4-(1H-Benzimidazol-2-yl)-6-(4-hydroxy-3-methoxy-5-methylamino-methylphenyl)-2H-pyridazin-3-one 180 mg of 6-[3-methoxy-5-methylaminomethyl-4-(2-trimethylsilanyl-ethoxy-methoxy)-phenyl]-2-(2-trimethylsilanylethoxymethyl)-4-[1-(2-trimethylsilanyl-ethoxymethyl)-1H-benzimidazol-2-yl]-2H-pyridazin-3-one are dissolved in a 1:1 mixture of trifluoroacetic acid and dichloromethane, and the reaction mixture is stirred at room temperature for 5 hours. The volatile components are then distilled off, and the residue is dissolved in a 1:1 mixture of methanol and 2N NaOH. After stirring at room temperature for 2 hours, the solution is neutralized with 2N HCl, the solution is evaporated to dryness, and the residue is purified by RP-HPLC (acetonitrile/water (+0.1% TFA)).
Yield 29 mg. MS (ES+) m/z 378 (M+H).

EXAMPLE 74

4-(1H-Benzimidazol-2-yl)-6-(1-methyl-1H-imidazol-4-yl)-2H-pyridazin-3-one

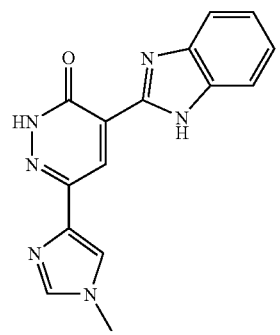

Example 74 is synthesized in accordance with example 55d

EXAMPLE 75

6-(4-Hydroxy-3,5-dimethylphenyl)-4-(3H-imidazo[4,5-c]pyridin-2-yl)-2H-pyridazin-3-one

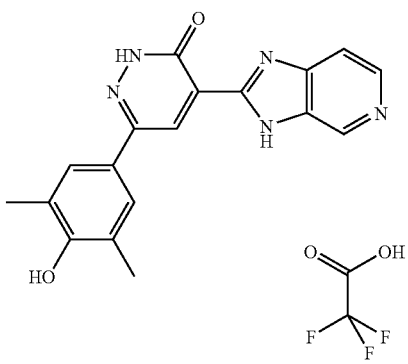

MS (ES+) m/z 344 (M+H).

Example 75 is synthesized in accordance with example 15.

EXAMPLE 76

6-(4-Hydroxy-3,5-dimethylphenyl)-4-(3H-imidazo[4,5-b]pyridin-2-yl)-2H-pyridazin-3-one

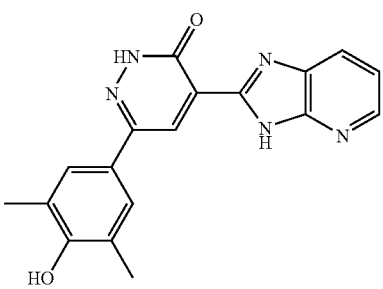

MS (ES+) m/z 344 (M+H).

Example 76 is synthesized in accordance with example 15.

EXAMPLE 77

4-(1H-Benzimidazol-2-yl)-6-[6-(2-morpholin-4-ylethylamino)pyrimidin-4-yl]-2H-pyridazin-3-one

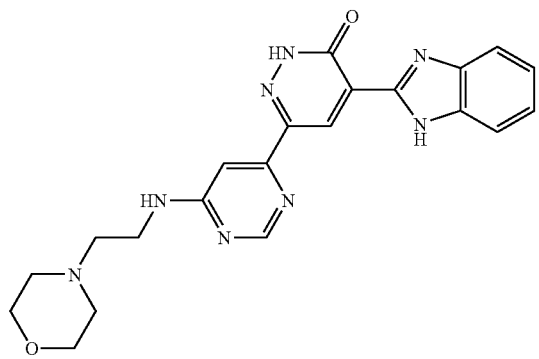

MS (ES+) m/z 419 (M+H).

Example 77 is synthesized in accordance with example 55.

EXAMPLE 78

4-(1H-Benzimidazol-2-yl)-6-[6-(2-methoxyethylamino)pyrimidin-4-yl]-2H-pyridazin-3-one

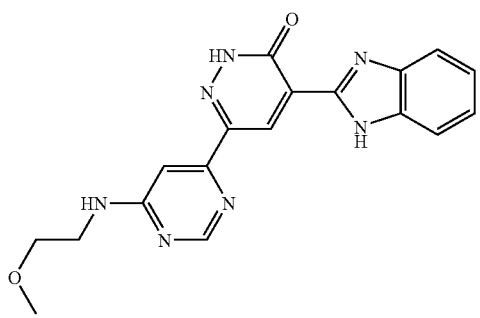

MS (ES+) m/z 364 (M+H).

Example 78 is synthesized in accordance with example 55.

EXAMPLE 79

4-(1H-Benzimidazol-2-yl)-6-[6-(2-hydroxy-1,1-dimethylethylamino)pyrimidin-4-yl]-2H-pyridazin-3-one

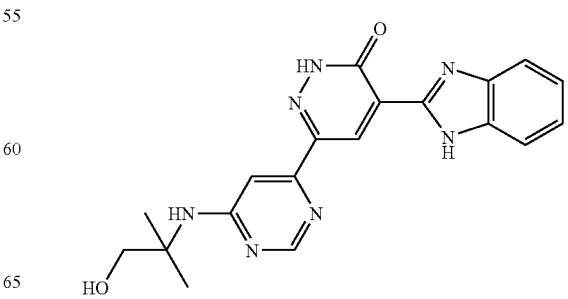

MS (ES+) m/z 378 (M+H).
Example 79 is synthesized in accordance with example 55.

EXAMPLE 80

Methyl 2-[6-(2-methyl-6-methylaminopyrimidin-4-yl)-3-oxo-2,3-dihydro-pyridazin-4-yl]-3H-benzimidazole-5-carboxylate

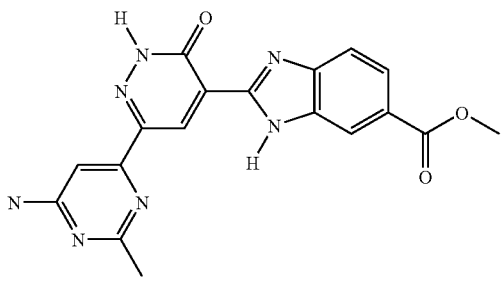

MS (ES+) m/z 392 (M+H).
Example 80 is synthesized in accordance with example 55 starting from 6-chloro-4-(6-methoxycarbonyl-1-(2-trimethylsilanylethoxymethyl)-1H-benzimidazol-2-yl]-2-(2-trimethylsilanylethoxymethyl)-2H-pyridazin-3-one (example 42a).

EXAMPLE 81

4-(1H-Benzimidazol-2-yl)-6-(2-methoxypyrimidin-4-yl)-2H-pyridazin-3-one

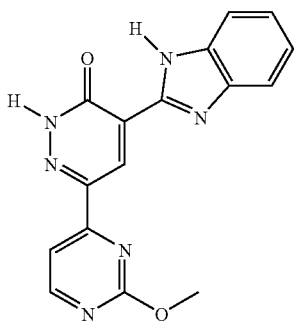

MS (ES+) m/z 321 (M+H)
Example 81 is synthesized in analogy to example 55.

EXAMPLE 82
4-(1H-Benzimidazol-2-yl)-6-(4-hydroxy-3-methoxy-5-oxazol-5-ylphenyl)-2H-pyridazin-3-one

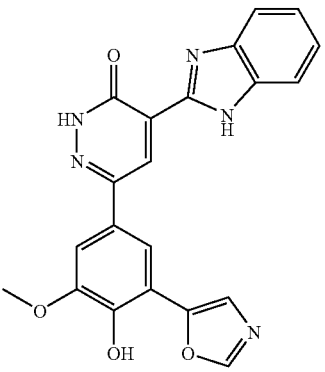

MS (ES+) m/z 402 (M+H)

(a) 5-[5-Bromo-3-methoxy-2-(2-trimethylsilanylethoxymethoxy)-phenyl]oxazole 1 g of 5-bromo-3-methoxy-2-(2-trimethylsilanylethoxymethoxy)benzaldehyde and 0.54 g of p-toluenesulfonylmethyl isocyanide are dissolved in 40 ml of methanol, 0.38 g of o-potassiumcarbonate is added in portions, and the reaction mixture is heated to reflux for 18 h. The solvent is then distilled off, and the crude product is purified by silica gel chromatography (ethyl acetate/heptane).
Yield 600 mg MS (ES+) m/z 401 (M+H)

(b) 6-(3-Methoxy-5-oxazol-5-yl-4-(2-trimethylsilanylethoxymethoxy)-phenyl]-2-(2-trimethylsilanylethoxymethyl)-4-[1-(2-trimethylsilanyl-ethoxymethyl)-1H-benzimidazol-2-yl]-2H-pyridazin-3-one This compound is synthesized in accordance with example 35(b) from 360 mg of 5-[5-bromo-3-methoxy-2-(2-trimethylsilanylethoxymethoxy)phenyl]oxazole and 310 mg of 2-(2-trimethylsilanylethoxymethyl)-4-[1-(2-trimethylsilanylethoxymethyl)-1H-benzimidazol-2-yl]-2H-pyridazin-3-one-6-boronic acid.
Yield: 135 mg. MS (ES+) m/z 792 (M+H).

(c) 4-(1H-benzimidazol-2-yl)-6-(4-hydroxy-3-methoxy-5-oxazol-5-ylphenyl)-2H-pyridazin-3-one This compound is prepared in accordance with example 15(e).
Yield: 40 mg. MS (ES+) m/z 402 (M+H).

EXAMPLE 83

6-(3-Chlorophenyl)-4-[6-(4-methylpiperazin-1-yl methyl)-1H-benzimidazol-2-yl]-2H-pyridazin-3-one

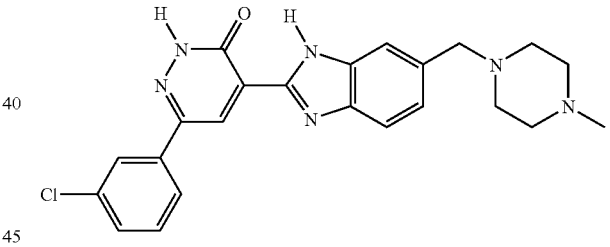

MS (ES+) m/z 435 (M+H).
Example 83 is synthesized in accordance with example 55.

EXAMPLE 84

4-(1H-Benzimidazol-2-yl)-6-[2-(2-morpholin-4-ylethoxy)pyrimidin-4-yl]-2H-pyridazin-3-one

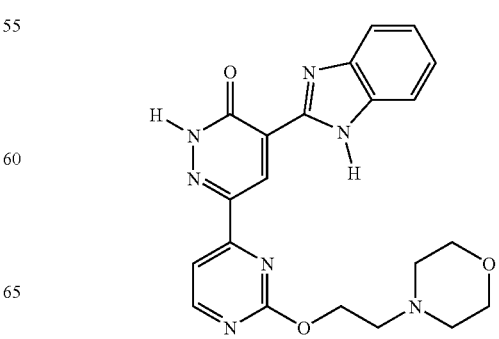

MS (ES+) m/z 420 (M+H).
Example 84 is synthesized in analogy to example 55.

EXAMPLE 85

4-(1H-Benzimidazol-2-yl)-6-[2-(2-diethylaminoethylamino)pyrimidin-4-yl]-2H-pyridazin-3-one

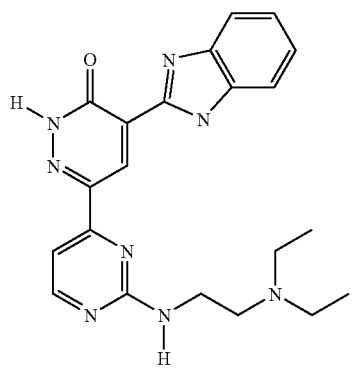

MS (ES+) m/z 405 (M+H).
Example 85 is synthesized in analogy to example 55.

EXAMPLE 86

4-(1H-Benzimidazol-2-yl)-6-(2-cyclopropylpyrimidin-4-yl)-2H-pyridazin-3-one

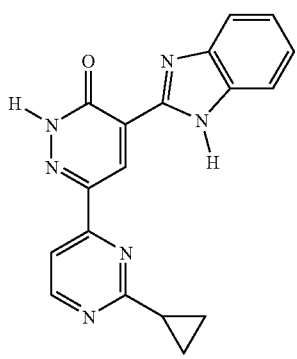

a) 6-(2-Cyclopropylpyrimidin-4-yl)-2-(2-trimethylsilanylethoxymethyl)-4-[1-(2-trimethylsilanylethoxymethyl)-1H-benzimidazol-2-yl]-2H-pyridazin-3-one 100 mg of 6-(2-chloropyrimidin-4-yl)-2-(2-trimethylsilanylethoxymethyl)-4-[1-(2-trimethylsilanylethoxymethyl)-1H-benzimidazol-2-yl]-2H-pyridazin-3-one, 29.2 mg of cyclopropylboronic acid and 138 mg of potassium phosphate are dissolved in 1 ml of toluene and 0.05 ml of water and, under an argon atmosphere, 17 mg of 1,1'-bis(diphenylphosphino)ferrocenepalladium(II) chloride (1:1 complex with CH2Cl2) are added. The mixture is stirred at 100° C. for 9 h. After cooling to room temperature, it is diluted with 15 ml of water and extracted several times with ethyl acetate, and the combined organic phases are extracted once more with saturated sodium chloride solution and dried using a Varian Chem Elut CE 1005 cartridge. The crude product is purified by RP HPLC (acetonitrile (+0.05% HCOOH)/water (+0.05% HCOOH)).
Yield 28.4 mg b) 4-(1H-Benzimidazol-2-yl)-6-(2-cyclopropylpyrimidin-4-yl)-2H-pyridazin-3-one 27 mg of 6-(2-cyclopropylpyrimidin-4-yl)-2-(2-trimethylsilanylethoxymethyl)-4-[1-(2-trimethylsilanylethoxymethyl)-1H-benzimidazol-2-yl]-2H-pyridazin-3-one are dissolved in 2.5 ml of 4M hydrochloric acid solution in dioxane and 1 ml of ethanol and stirred at room temperature for 2 days. The solvent is then distilled off, and the residue is dissolved in 2 ml of dichloromethane and 1 ml of trifluoroacetic acid and again stirred at room temperature for 3 h. Distillation off is then repeated, and the residue is dissolved in 1 ml of 2M sodium hydroxide solution and 2 ml of water, and the mixture is stirred at room temperature for 10 h. For workup, it is neutralized with 2M hydrochloric acid, the volatile components are distilled off, and the crude product is purified by RP HPLC (acetonitrile (+0.05% HCOOH)/water (+0.05% HCOOH)).
MS (ES+) m/z 331 (M+H).
Yield 9.2 mg

EXAMPLE 87
4-(1H-Benzimidazol-2-yl)-6-pyrimidin-2-yl-2H-pyridazin-3-one

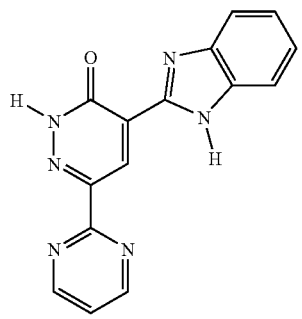

MS (ES+) m/z 291 (M+H).
Example 87 is synthesized in accordance with example 55b.

EXAMPLE 88
4-(1H-Benzimidazol-2-yl)-6-(4-methoxypyrimidin-2-yl)-2H-pyridazin-3-one

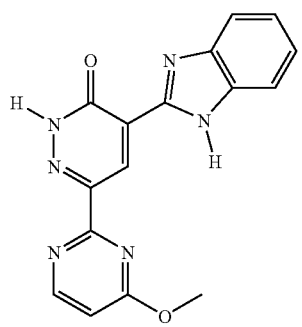

MS (ES+) m/z 321 (M+H).

Example 88 is synthesized in accordance with example 55b.

EXAMPLE 89

4-(1H-Benzimidazol-2yl)-6-(4-dimethylaminopyrimidin-2-yl)-2H-pyridazin-3-one

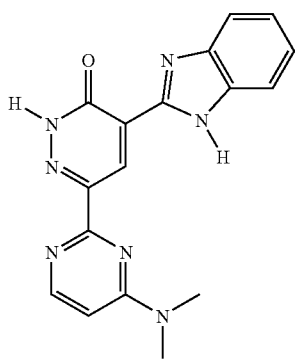

MS (ES+) m/z 334 (M+H).

Example 89 is synthesized in accordance with Example 55b.

EXAMPLE 90

4-(1H-Benzimidazol-2-yl)-6-[2-(2-diethylaminoethylsulfanyl)pyrimidin-4-yl]-2H-pyridazin-3-one

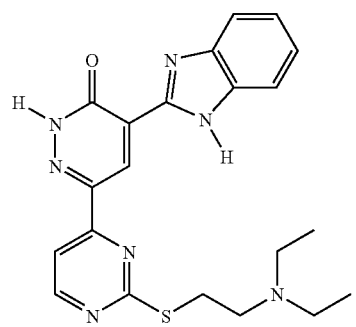

MS (ES+) m/z 422 (M+H).

Example 90 is synthesized in accordance with example 55.

EXAMPLE 91

4-(1H-Benzimidazol-2-yl)-6-[2-(2-hydroxy-1,1-dimethylethylamino)-6-methylpyrimidin-4-yl]-2H-pyridazin-3-one

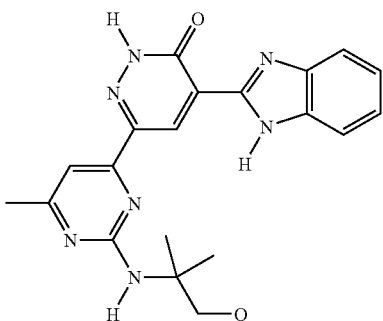

MS (ES+) m/z 392 (M+H).

Example 91 is synthesized in accordance with example 55.

EXAMPLE 92

4-(1H-Benzimidazol-2-yl-6-(6-methyl-2-methylaminopyrimidin-4-yl)-2H-pyridazin-3-one

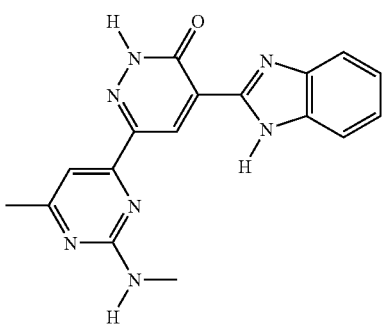

MS (ES+) m/z 334 (M+H).

Example 92 is synthesized in accordance with example 55.

EXAMPLE 93

6-(3,5-Dichlorophenyl)-4-[6-(4-methylpiperazin-1-ylmethyl)-1H-benzimidazol-2-yl]-2H-pyridazin-3-one

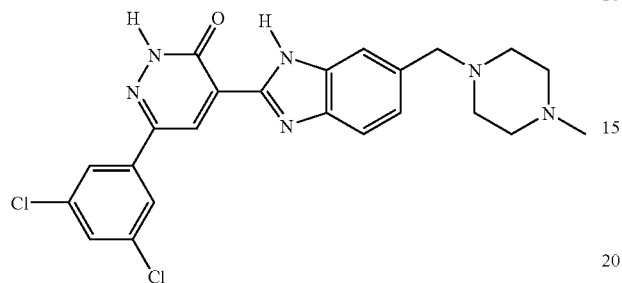

MS (ES+) m/z 470 (M+H).

Example 93 is synthesized in accordance with example 55.

EXAMPLE 94

4-(1H-Benzimidazol-2-yl)-6-{2-[methyl-(2-morpholin-4-ylethyl)amino]-pyrimidin-4-yl}-2H-pyridazin-3-one

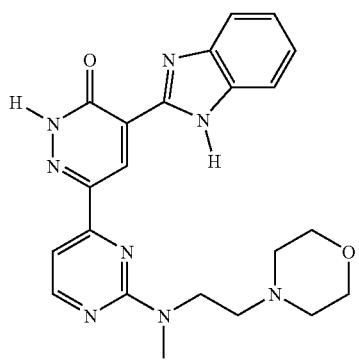

a) 6-{2-(Methyl-(2-morpholin-4-ylethyl)amino]pyrimidin-4-yl}-2-(2-trimethylsilanylethoxymethyl)-4-[1-(2-trimethylsilanylethoxymethyl)-1H-benzimidazol-2-yl]-2H-pyridazin-3-one 86 mg of 6-(2-chloropyrimidin-4-yl)-2-(2-trimethylsilanylethoxymethyl)-4-[1-(2-trimethylsilanylethoxymethyl)-1H-benzimidazol-2-yl]-2H-pyridazin-3-one (55d) are dissolved in 2 ml of THF and, at 0° C., 0.06 ml of 2M lithium diisopropylamine solution in THF/hexane is added dropwise and stirred at 0° C. for 30 min, and 0.008 ml of methyl iodide is added dropwise. After stirring for 20 h, the solvent is distilled off and the procedure is repeated to complete the conversion. This is followed by dilution with water, extraction with ethyl acetate and drying of the combined organic phases.

17 mg of a substance mixture that comprises both the desired product and a byproduct which now has only one SEM protective group are isolated by RP-HPLC. This mixture is employed for the next reaction.

b) 4-(1H-Benzimidazol-2-yl)-6-{2-[methyl-(2-morpholin-4-ylethyl)amino]pyrimidin-4-yl}-2H-pyridazin-3-one This compound is synthesized from the product mixture described under 94a as described for 55d.

Yield 4.8 mg MS (ES+) m/z 433 (M+H).

EXAMPLE 95

4-(1H-Benzimidazol-2-yl)-6-pyrimidin-5-yl-2H-pyridazin-3-one

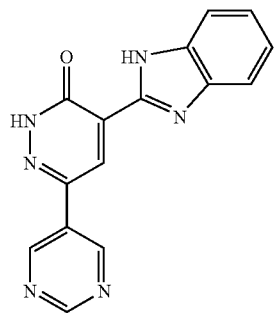

Example 95 is synthesized in accordance with example 55b.

MS (ES+) m/z 291 (M+H).

Functional measurements to ascertain $IC_{50}$ values:

GSK-3β

GSK-3β activity is measured using human recombinant GSK-3β and a primed (pre-phosphorylated) substrate peptide (derived from glycogen synthase and containing the phosphorylation sites 3a, b, and c) on the basis of the AlphaScreen technology in 384-well plate format (small volume plate, white, Greiner). In a final volume of 11 μl, 2 μl of compound (1 nM-100 mM in kinase buffer, DMSO kept constant at 0.9%), 2 μl of GSK-3β solution (0.18 nM) and 2 μl of biot. phospho-glycogen synthase peptide (34 nM) in kinase buffer (20 mM Hepes, pH 7.4, 10 mM MgCl, 200 mM EDTA, 1 mM DTT, 0.1 mg/ml BSA, 10 μM ATP) are incubated at room temperature for 60 min. After adding 2.5 ml Donor beads (20 μg/ml) and 2.5 ml antibody (anti-phosphoglycogen synthase 1:2000)-coated Acceptor beads (40 μg/ml) in AlphaScreen detection buffer (20 mM Hepes, pH 7.4, 10 mM MgCl, 40 mM EDTA, 1 mM DTT, 0.1 mg/ml BSA), plates are incubated at room temperature (in the dark) overnight and then placed in a reader (Alphaquest or Fusion) to measure final fluorescence. $IC_{50}$ values are calculated from the fitted curve corrected for bank values (absence of GSK-3β) and performed in triplicate.

| Example no. | $IC_{50}$ [nM] |
| --- | --- |
| 6 | 16 |
| 21 | 57 |
| 25 | 56 |
| 38 | 32 |
| 42 | 7 |
| 43 | 1.5 |
| 46 | 28 |
| 50 | 157 |
| 53 | 42 |
| 58 | 50 |
| 68 | 63 |

COMPARATIVE EXAMPLES
| No. | Structure | IC 50 10 μM ATP | Origin |
|---|---|---|---|
| 1 [D1-I-1] | 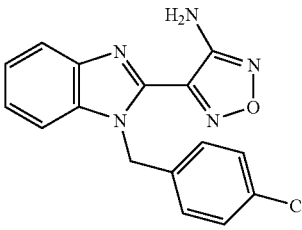 | 100 μM | Prepared according to WO 2003/066629 |
| 2 [D1-I-3] | 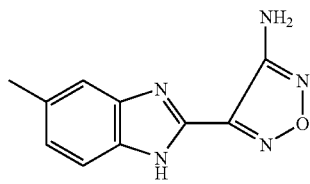 | 11 μM | Prepared according to WO 2003/066629 |
| 3 [D1-I-3] | 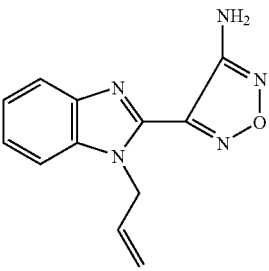 | 1.2 μM | Prepared according to WO 2003/066629 |
| 4 | 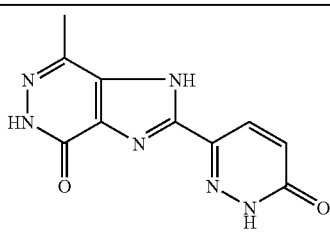 | 65 μM | Commercial available |

-continued

Comparative examples

| | | | |
|---|---|---|---|
| 5 | 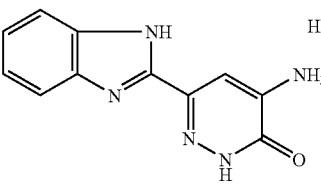 | 100 µM | Commercially available |
| 6 | 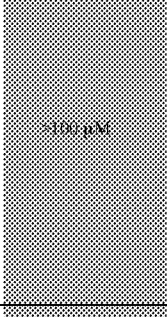 | 84 µM | Commercial available |

What is claimed is:

1. A compound of formula (I)

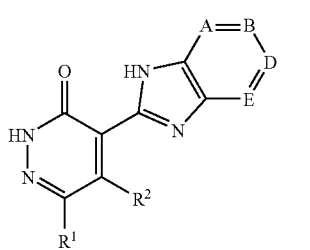

A is $CR^3$;
B is $CR^4$;
D is $CR^5$;
E is $CR^6$;
$R^1$ is halogen, or
$R^1$ is $C_1$-$C_{10}$-alkyl optionally substituted one or more times by halogen, CN, $NO_2$, —$OR^7$, —$C(O)R^7$, —$C(O)OR^7$, —O—$C(O)R^7$, —$NR^7R^8$, —$NHC(O)R^7$, —$C(O)NR^7R^8$, —$NHC(S)R^7$, —$C(S)NR^7R^8$, —$SR^7$, —$S(O)R^7$, —$SO_2R^7$, —$NHSO_2R^7$, —$SO_2NR^7R^8$, —O—$SO_2R^7$, —$SO_2$—O—$R^7$, aryl, heteroaryl, heterocyclyl, trifluoromethyl or trifluoromethoxy, wherein the heterocyclyl, aryl and heteroaryl are optionally substituted one or more times by $C_1$-$C_6$-alkyl, $C_1$-$C_6$-alkoxy, halogen, trifluoromethyl, trifluoromethoxy or OH, or
$R^1$ is heterocyclyl, aryl or heteroaryl, each of which is optionally substituted one or more times by:
halogen, —CN, $NO_2$, —$CH_2$—$R^7$, —$CH_2$—$NH_2$, —$CH_2$—$NH(C_1$—$C_6$—alkyl), —$CH_2$—$N(C_1$-$C_6$-alkyl)$_2$, —$CH_2$—OH, —$CH_2$—O—($C_1$-$C_6$-alkyl), —$OR^7$, —$C(O)R^7$, —$C(O)OR^7$, —O—$C(O)R^7$, —$NR^7R^8$, —$NHC(O)R^7$, —$C(O)NR^7R^8$, —$NHC(S)R^7$, —$C(S)NR^7R^8$, —$SR^7$, —$S(O)R^7$, —$SO_2R^7$, —$NHSO_2R^7$, —$SO_2NR^7R^8$, —O—$SO_2R^7$, —$SO_2$—O—$R^7$, trifluoromethyl, trifluoromethoxy, aryl, or heteroaryl, wherein the aryl and heteroaryl are optionally substituted one or more times by $C_1$-$C_6$-alkyl, $C_1$-$C_6$-alkoxy, halogen, trifluoromethyl, trifluoromethoxy or OH;

$R^2$ is hydrogen or $C_1$-$C_{10}$-alkyl;
$R^3$, $R^4$, $R^5$ and $R^6$ are, independently, hydrogen, halogen, —CN, $NO_2$, —$CH_2$—$R^8$, —$CH_2$—$NH_2$, —$CH_2$—NH ($C_1$-$C_6$-alkyl), —$CH_2$—$N(C_1$—$C_6$-alkyl)$_2$, —$CH_2$—OH, —$CH_2$—O—($C_1$—$C_6$-alkyl), —$OR^8$, —$C(O)R^8$, —$C(O)OR^8$, —O—$C(O)R^8$, —$NR^7R^8$; —$NHC(O)R^8$, —$C(O)NR^7R^8$, —$NHC(S)R^8$, —$C(S)NR^7R^8$, —$SR^8$, —$S(O)R^8$, —$SO_2R^8$, —$NHSO_2R^8$, —$SO_2NR^7R^8$, —O—$SO_2R^8$, —$SO_2$—O—$R^8$, aryl, heteroaryl, heterocyclyl, trifluoromethyl or trifluoromethoxy, wherein the heterocyclyl, aryl and heteroaryl are optionally substituted one or more times by $C_1$-$C_6$-alkyl, $C_1$-$C_6$-alkoxy, oxo, halogen, trifluoromethyl, trifluoromethoxy or OH;
$R^7$ and $R^8$ are, independently,
H, or
$C_1$-$C_{10}$-alkyl, $C_2$-$C_{10}$-alkenyl, $C_2$-$C_{10}$-alkynyl, heterocyclyl, aryl or heteroaryl, each of which is optionally substituted one or more times by: oxo, halogen, —OH, $C_1$-$C_{10}$-alkoxy, ($C_1$-$C_{10}$-alkyl)thio-, —C(O) OH, —C(O)O—($C_1$-$C_6$)alkyl, —$C(O)NH_2$, —C(O) NH($C_1$-$C_6$-alkyl), —$C(O)N(C_1$-$C_{10}$-alkyl)$_2$, trifluoromethyl, trifluoromethoxy, —CN, —$NH_2$, —NH ($C_1$-$C_{10}$-alkyl), —N($C_1$-$C_{10}$-alkyl)$_2$, heteroaryl, heterocyclyl, or aryl, wherein the heteroaryl, heterocyclyl and aryl are optionally substituted one or more times by $C_1$-$C_6$-alkyl, $C_1$-$C_6$-alkoxy, oxo, trifluoromethyl, trifluoromethoxy, fluorine, chlorine or OH;
heteroaryl is a 5 to 10-membered, aromatic, mono- or bicyclic heterocyclic ring system containing one or more heteroatoms selected from N, O and S;
aryl is a 5 to 10-membered, aromatic, mono- or bicyclic carbocyclic ring system; and
heterocyclyl s a 5 to 10-membered, nonaromatic, mono- or bicyclic heterocyclic ring system containing one or more heteroatoms selected from N, O and S;

provided that $R^1$ is not optionally substituted pyrazolo[1,5-a]pyridinyl;
or a physiologically tolerated salt thereof.

2. The compound according to claim 1, wherein:
$R^1$ is fluorine, chlorine or bromine, or
$R^1$ is $C_1$-$C_6$-alkyl optionally substituted one or more times by halogen, —$OR^7$, —$C(O)R^7$, —$C(O)OR^7$, —$NR^7H$, —$NR^7(C_1$-$C_6$-alkyl), —$C(O)NR^7H$, —$SR^7$, aryl, heteroaryl, heterocyclyl, trifluoromethyl or trifluoromethoxy, wherein the heterocyclyl, aryl and heteroaryl optionally substituted one or more times by $C_1$-$C_6$-alkyl, $C_1$-$C_6$-alkoxy, halogen, trifluoromethyl, trifluoromethoxy or OH, or
$R^1$ is heterocyclyl, aryl or heteroaryl, each of which is optionally substituted one or more times by:
halogen, —$CH_2$—$R^7$, —$CH_2$—$NH_2$, —$CH_2$—$NH(C_1$-$C_6$-alkyl), —$CH_2$—$N(C_1$-$C_6$- alkyl)$_2$, —$CH_2$—OH, —$CH_2$—O—($C_1$-$C_6$-alkyl), —$OR^7$, —$C(O)R^7$, —$C(O)OR^7$, —$NR^7H$, —$NR^7(C_1$-$C_6$-alkyl-), —$C(O)NR^7H$, —$SR^7$, trifluoromethyl, trifluoromethoxy, aryl or heteroaryl, wherein the aryl and heteroaryl are optionally substituted one or more times by $C_1$-$C_6$-alkyl, $C_1$-$C_6$-alkoxy, halogen, trifluoromethyl, trifluoromethoxy or OH;
$R^2$ is hydrogen or $C_1$-$C_6$-alkyl;
$R^3$, $R^4$, $R^5$ and $R^6$ are, independently, hydrogen, halogen, —CN, —$CH_2$—$R^8$, —$CH_2$—$NH_2$, —$CH_2$—$NH(C_1$-$C_6$-alkyl), —$CH_2$—$N(C_1$-$C_6$-alkyl)$_2$, —$CH_2$—OH, —$CH_2$—O—($C_1$-$C_6$-alkyl), —$OR^8$, —$C(O)R^8$, —$C(O)OR^8$, —$NR^8H$, —$NR^8(C_1$-$C_6$-alkyl), —$C(O)$ $NR^8H$, —$SR^8$, —$SO_2NR^8H$, —$SO_2$—$R^8$, aryl, heteroaryl, heterocyclyl, trifluoromethyl or trifluoromethoxy, wherein the heterocyclyl, aryl and heteroaryl are optionally substituted one or more times by $C_1$-$C_6$-alkyl, $C_1$-$C_6$-alkoxy, oxo, halogen, trifluoromethyl, trifluoromethoxy or OH;
$R^7$ and $R^8$ are, independently, H, or
$C_1$-$C_6$-alkyl, heterocyclyl, phenyl or heteroaryl, each of which is optionally substituted one or more times by:
fluorine, chlorine, bromine, OH, $C_1$-$C_6$-alkoxy, —C(O)OH, —C(O)O —($C_1$-$C_6$-alkyl), —C(O) $NH_2$, —$C(O)NH(C_1$-$C_6$-alkyl), —$C(O)N(C_1$-$C_{10}$-Alkyl)$_2$,trifluoromethyl, trifluoromethoxy, —$NH_2$, —$NH(C_1$-$C_6$-alkyl), —$N(C_1$-$C_6$-alkyl)$_2$, heterocyclyl, phenyl or heteroaryl, wherein the heterocyclyl, phenyl and heteroaryl are optionally substituted one or more times by $C_1$-$C_3$-alkyl, $C_1$-$C_3$-alkoxy, oxo, trifluoromethyl, trifluoromethoxy, fluorine, chlorine or OH;
heteroaryl is imidazolyl, thiophenyl, furanyl, thiazolyl, imidazolyl, oxazolyl, isoxazolyl, pyridinyl, pyrimidinyl, pyrazolyl, benzo[b]thiophenyl, thiazolo[3,2-b][1,2,4]-triazolyl, pyrrolyl, quinolinyl, isoquinolinyl, 1,2,3,4-tetrahydroquinolinyl, benzimidazolyl, indolyl or 1,3-benzodioxolyl;
aryl is naphthyl, indanyl or phenyl; and
heterocyclyl is 2-oxoazepanyl, 1,4-oxazepanyl, dihydropyridinonyl, tetrahydrofuranyl, 1,3-dioxolanyl, morpholinyl, pyrrolidinyl, piperazinyl or piperidinyl;
or a physiologically tolerated salt thereof.

3. The compound according to claim 2, wherein:
$R^1$ is chlorine, or
$R^1$ is $C_1$-$C_6$-alkyl optionally substituted one or more times by:
fluorine, chlorine, OH, $C_1$-$C_6$-alkoxy, —$NH_2$, —NH ($C_1$-$C_6$-alkyl), —$N(C_1$-$C_6$-alkyl)$_2$, heterocyclyl-($C_1$-$C_6$-alkyl)—NH—, aryl-($C_1$-$C_6$-alkyl) —NH—, heterocyclyl, aryl or heteroaryl, wherein the heterocyclyl, aryl and heteroaryl moieties are optionally substituted one or more times by $C_1$-$C_4$-alkyl, $C_1$-$C_4$-alkoxy, fluorine, chlorine, trifluoromethyl, trifluoromethoxy or OH, or
$R^1$ is phenyl, pyridinyl, pyrimidinyl, pyrazolyl, thiophenyl, oxazolyl, isoxazolyl, thiazolyl, imidazolyl, morpholinyl, dihydropyridinonyl, benzo[b]thiophenyl, 1,3-benzodioxolyl or thiazolo[3,2-b][1,2,4]-triazolyl, each of which is optionally substituted one or more times by halogen, —$CH_2$—$R^7$, —$CH_2$—$NH_2$, —$CH_2$—$NH(C_1$-$C_6$-alkyl), —$CH_2$—$N(C_1$-$C_6$-alkyl)$_2$, —$CH_2$—OH, —$CH_2$—O—($C_1$-$C_6$-alkyl), —$OR^7$, —$C(O)R^7$, —$C(O)OR^7$, —$NR^7H$, —$NR^7(C_1$-$C_6$-alkyl-), —$C(O)$ $NR^7H$, —$SR^7$, aryl, heteroaryl, trifluoromethyl or trifluoromethoxy, wherein the aryl and heteroaryl are optionally substituted one or more times by $C_1$-$C_6$-alkyl, $C_1$-$C_6$-alkoxy, halogen, trifluoromethyl, trifluoromethoxy or OH;
$R^2$ is hydrogen; and
$R^3$, $R^4$, $R^5$ and $R^6$ are, independently, hydrogen, fluorine, chlorine, bromine, —CN, —$CH_2$—$R^8$, —$CH_2$—$NH_2$, —$CH_2$—$NH(C_1$-$C_6$-alkyl), —$CH_2$—$N(C_1$-$C_6$-alkyl)$_2$, —$CH_2$—OH, —$CH_2$—O—($C_1$-$C_6$-alkyl), —$OR^8$, —$C(O)R^8$, —$C(O)OR^8$, —$NR^8H$, —$NR^8(C_1$-$C_6$-alkyl), —$C(O)NR^8H$, —$SR^8$, —$SO_2NR^8H$, $SO_2$—$R^8$, heterocyclyl, trifluoromethyl and trifluoromethoxy, wherein the heterocyclyl is optionally substituted one or more times by $C_1$-$C_6$-alkyl, $C_1$-$C_6$-alkoxy, halogen, trifluoromethyl, trifluoromethoxy or OH;
or a physiologically tolerated salt thereof.

4. The compound according to claim 3, wherein:
$R^1$ is phenyl, pyridinyl, pyrimidinyl, pyrazolyl, thiophenyl, oxazolyl, isoxazolyl, thiazolyl, imidazolyl, morpholinyl, dihydropyridinonyl, benzo[b]thiophenyl, benzodioxolyl or thiazolo[3,2-b][1,2,4]-triazolyl, each of which is optionally substituted one or more times by:
halogen, $C_1$-$C_6$-alkyl, —OH, $C_1$-$C_6$-alkoxy, ($C_1$-$C_6$-alkyl)thio-, —$NH_2$, —$N(C_1$-$C_6$-alkyl)$_2$, —$NH(C_1$-$C_6$-alkyl), $HO(O)C$—($C_1$-$C_6$-alkyl)—NH—, ($C_1$-$C_6$-alkyl) —$O(O)C$—($C_1$-$C_6$-alkyl)—NH—, $H_2N(O)$ C—($C_1$-$C_6$-alkyl)—NH—, ($C_1$-$C_6$-alkyl)HN(O)C—($C_1$-$C_6$-alkyl)—NH—, $H_2N$—($C_1$-$C_6$-kyl)—, ($C_1$-$C_6$-alkyl) HN—($C_1$-$C_6$-alkyl)—, ($C_1$-$C_6$-alkyl)$_2$N—($C_1$-$C_6$-alkyl)—, $H_2N$—($C_1$-$C_6$-alkyl) —NH—, ($C_1$-$C_6$-alkyl)HN—($C_1$-$C_6$-alkyl)—NH—, ($C_1$-$C_6$-alkyl)$_2$ N—($C_1$-$C_6$-alkyl)—NH—, ($C_1$-$C_6$-alkyl)—O—($C_1$-$C_6$-alkyl)—NH—, HO—($C_1$-$C_6$-alkyl)—NH—, trifluoromethyl, trifluoromethoxy, phenyl-($C_1$-$C_6$-alkyl)—, —O-phenyl, heterocyclyl-($C_1$-$C_6$-alkyl)—O—, heterocyclyl-($C_1$-$C_6$-alkyl) —NH—, heteroaryl-($C_1$-$C_6$-alkyl)—NH—, phenyl-($C_1$-$C_6$-alkyl)—NH—, heterocyclyl-($C_1$-$C_6$-alkyl)-, phenyl or heteroaryl, wherein the heterocyclyl, phenyl and heteroaryl moieties are optionally substituted one or more times by $C_1$-$C_3$-alkyl, $C_1$-$C_3$-alkoxy, fluorine, chlorine, trifluoromethyl, trifluoromethoxy or OH; and
$R^3$, $R^4$, $R^5$ and $R^6$ are, independently, hydrogen, fluorine, chlorine, bromine, —CN, $C_1$-$C_6$-alkyl, —OH, $C_1$-$C_6$-alkoxy, —C(O)OH, —C(O)O—($C_1$-$C_6$-alkyl), —$NH_2$, —N ($C_1$-$C_6$-alkyl)$_2$, —$NH(C_1$-$C_6$-alkyl), $H_2N$—($C_1$-$C_6$-alkyl)—NH—, hydroxy-($C_1$-$C_6$-alkyl )—NH—, ($C_1$-$C_6$-alkyl)HN—($C_1$-$C_6$-alkyl)—NH—, ($C_1$-$C_6$-alkyl)NH—($C_1$-$C_6$-alkyl) —NH—, (heterocyclyl-($C_1$-$C_6$-alkyl)—NH—, (heteroaryl-($C_1$-$C_6$-alkyl)—NH—, phenyl-($C_1$-$C_6$-alkyl)—NH—, —$C(O)NH_2$, —C(O)N (C₁-C₆-alkyl)₂, —C(O)NH(C₁-C₆-alkyl), H₂N(C₁-C₆-alkyl)—NHC(O)—, hydroxy-(C₁-C₆-alkyl)—NHC(O)—, (C₁-C₆-alkyl)HN—(C₁-C₆-alkyl)—NHC(O)—, (C₁-C₆-alkyl)₂N—(C₁-C₆-alkyl)—NHC(O)—, heterocyclyl-(C₁-C₆-alkyl)—NHC(O)—, heteroaryl-(C₁-C₆-alkyl)—NHC(O)—, phenyl-(C₁-C₆-alkyl)—NHC(O)—, heterocyclyl, heterocyclyl-(C₁-C₆-alkyl), trifluoromethyl and trifluoromethoxy, wherein the heteroaryl, heterocyclyl and phenyl moieties are optionally substituted one or more times by C₁-C₆-alkyl, C₁-C₆-alkoxy, halogen, trifluoromethyl, trifluoromethoxy or OH;

or a physiologically tolerated salt thereof.

5. The compound according to claim 4, wherein:

$R^1$ is pyridin-4-yl, 4-hydroxy-3-methoxy-5-(methylaminomethyl)phenyl, 2-ethylaminopyrimidin-4-yl, 3,5-dimethyl-4-hydroxyphenyl, 2-(1-phenylethylamino)pyrimidin-4-yl, 2-(2-morpholin-4-ylethylamino)pyrimidin-4-yl, 2-methylaminopyrimidin-4-yl, 6-methyl-2-(2-morpholin-4- ylethylamino)pyrimidin-4-yl, 3-methoxy-4-hydroxyphenyl, 2-methylsulfanylpyrimidin-4-yl or 4-butylaminopyrimidin-4-yl; and $R^3$, $R^4$, $R^5$ and $R^6$ are, independently, hydrogen, fluorine, chlorine, bromine, —CN, —C(O)O -methyl, (2-diethylaminoethyl)—NHC(O)—, COOH, methoxy, ethoxy, (2-cyclohexylaminoethyl)—NHC(O)—, (3-(4-methylpiperazin-1-yl)propyl)—NHC(O)—, (3-hydroxypropyl)—NHC(O)—, (3-cyclohexylaminopropyl)—NHC(O)—, (3-imidazol-1-ylpropyl)—NHC(O)—, methyl, ethyl, 4-methylpiperazin-1-yl, trifluoromethyl or trifluoromethoxy;

or a physiologically tolerated salt thereof.

6. The compound according to claim 1, which is:

Methyl 2-(3-oxo-6-pyridin-4-yl-2,3-dihydropyridazin-4-yl)-1H-benzimidazole-5- carboxylate, 2-(3-oxo-6-pyridin-4-yl-2,3-dihydropyridazin-4-yl)-1H-benzimidazole-5-carboxylic acid, 2-(3-Oxo-6-pyridin-4-yl-2,3-dihydropyridazin-4-yl)-1H-benzimidazole-5-carboxylic acid (2-diethylaminoethyl)amide, 4-(5-Chloro-1H-benzimidazol-2-yl)-6-(2-ethylaminopyrimidin-4-yl)-2H-pyridazin-3-one, 4-(6-Chloro-1H-benzimidazol-2-yl)-6-pyridin-4-yl-2H-pyridazin-3-one, 4-(6-Trifluoromethyl-1H-benzimidazol-2-yl)-6-pyridin-4-yl-2H-pyridazin-3-one, 4-(6-Methoxy-1H-benzimidazol-2-yl)-6-pyridin-4-yl-2H-pyridazin-3-one, 2-(3-Oxo-6-pyridin-4-yl-2,3-dihydropyridazin-4-yl)-1H-benzimidazole-5-carboxylic acid (2-cyclohexylaminoethyl)amide, 2-(3-Oxo-6-pyridin-4-yl-2,3-dihydropyridazin-4-yl)-1H-benzimidazole-5-carboxylic acid [3-(4-methylpiperazin-1-yl)propyl]amide, 2-(3-Oxo-6-pyridin-4-yl-2,3-dihydropyridazin-4-yl)-1H-benzimidazole-5-carboxylic acid (3-hydroxypropyl)amide, 4-(5-Chloro-1H-benzimidazol-2-yl)-6-methyl-2H-pyridazin-3-one, 2-(3-Oxo-6-pyridin-4-yl-2,3-dihydropyridazin-4-yl)-1H-benzimidazole-5-carboxylic acid (3-cyclohexylaminopropyl)amide, 2-(3-Oxo-6-pyridin-4-yl-2,3-dihydropyridazin-4-yl)-1H-benzimidazole-5-carboxylic acid (3-imidazol-1-yl-propyl)amide, 4-(5-Chloro-1H-benzimidazol-2-yl)-6-(2-methylaminopyrimidin-4-yl)-2H-pyridazin-3-one, 4-(6-Chloro-1H-benzimidazol-2-yl)-6-(4-hydroxy-3,5-dimethylphenyl)-2H- pyridazin-3-one, 4-(6-Chloro-1H-benzimidazol-2-yl)-6-(4-hydroxy-3-methoxyphenyl)-2H-pyridazin-3-one, 4-(7-Methyl-1H-benzimidazol-2-yl)-6-pyridin-4-yl-2H-pyridazin-3-one, 4-(5,6-Dimethyl-1H-benzimidazol-2-yl)-6-pyridin-4-yl-2H-pyridazin-3-one, 4-[5-(4-Methylpiperazin-1-yl)-1H-benzimidazol-2-yl]-6-pyridin-4-yl-2H-pyridazin-3-one, 4-(5-Fluoro-1H-benzimidazol-2-yl)-6-pyridin-4-yl-2H-pyridazin-3-one, 4-(5-Cyano-1H-benzimidazol-2-yl)-6-pyridin-4-yl-2H-pyridazin-3-one, 4-(5-Bromo-1H-benzimidazol-2-yl)-6-pyridin-4-yl-2H-pyridazin-3-one, 6-(4-Hydroxy-3-methoxyphenyl)-4-(6-trifluoromethyl-1H-benzimidazol-2-yl)-2H- pyridazin-3-one, 6-(4-Hydroxy-3,5-dimethylphenyl)-4-(6-trifluoromethyl-1H-benzimidazol-2-yl)-2H- pyridazin-3-one, 6-(2-Butylaminopyrimidin-4-yl)-4-(6-chloro-1H-benzimidazol-2-yl)-2H-pyridazin-3-one, 6-(2-Butylaminopyrimidin-4-yl)-4-(6-trifluoromethyl-1H-benzimidazol-2-yl)-2H- pyridazin-3-one, 4-(1H-Benzimidazol-2-yl)-6-pyridin-4-yl-2H-pyridazin-3-one, 4-(6-Chloro-1H-benzimidazol-2-yl)-6-[2-((R)-1-phenylethylamino)pyrimidin-4-yl]-2H-pyridazin-3-one, 4-(5,6-Dichloro-1H-benzimidazol-2-yl)-6-pyridin-4-yl-2H-pyridazin-3-one, 4-(6-Chloro-5-fluoro-1H-benzimidazol-2-yl)-6-pyridin-4-yl-2H-pyridazin-3-one, 4-(6-Chloro-5-methyl-1H-benzimidazol-2-yl)-6-pyridin-4-yl-2H-pyridazin-3-one, 4-(5,7-Difluoro-1H-benzimidazol-2-yl)-6-pyridin-4-yl-2H-pyridazin-3-one, 4-(5-Chloro-6-methyl-1H-benzimidazol-2-yl)-6-(4-hydroxy-3-methoxyphenyl)-2H- pyridazin-3-one, 6-[2-(2-Morpholin-4-yl-ethylamino)pyrimidin-4-yl]-4-(6-trifluoromethyl-1H- benzimidazol-2-yl)-2H-pyridazin-3-one, 4-(5,6-Dichloro-1H-benzimidazol-2-yl)-6-(4-hydroxy-3-methoxyphenyl)-2H- pyridazin-3-one, 2-[6-(4-Hydroxy-3-methoxyphenyl)-3-oxo-2,3-dihydropyridazin-4-yl]-3H- benzimidazole-5-carboxylic acid, 6-[6-Methyl-2-(2-morpholin-4-yl-ethylamino)pyrimidin-4-yl]-4-(6-trifluoromethyl-1H-benzimidazol-2-yl)-2H-pyridazin-3-one, 4-(6-Chloro-1H-benzimidazol-2-yl)-6-(2-methylsulfanylpyrimidin-4-yl)-2H- pyridazin-3-one, 6-(4-Hydroxy-3,5-dimethylphenyl)-4-(7-methyl-1H-benzimidazol-2-yl)-2H- pyridazin-3-one, 4-[6-(4-Methylpiperazin-1-ylmethyl)-1H-benzimidazol-2-yl]-6-pyridin-4-yl-2H- pyridazin-3-one, 6-(4-Hydroxy-3,5-dimethylphenyl)-4-[6-(4-methylpiperazin-1-ylmethyl)-1H- benzimidazol-2-yl]-2H-pyridazin-3-one, 2-[6-(4-Hydroxy-3,5-d imethylphenyl)-3-oxo-2,3-dihydropyridazin-4-yl]-3H- benzimidazole-5-carboxylic acid, 4-(1H-Benzimidazol-2-yl)-6-chlor-2H-pyridazin-3-one, 4-(1H-Benzimidazol-2-yl)-6-thiophen-3-yl-2H-pyridazin-3-one, 4-(1H-Benzimidazol-2-yl)-6-thiazol-2-yl-2H-pyridazin-3-one, 4-(1H-Benzimidazol-2-yl)-6-cyclopropyl-2H-pyridazin-3-one, 4-[6-(4-Methylpiperazin-1-ylmethyl)-1H-benzimidazol-2-yl]-6-thiophen-3-yl-2H-pyridazin-3-one,
4-(1H-Benzimidazol-2-yl)-6-(1-methyl-6-oxo-1,6-dihydropyridin-3-yl)-2H-pyridazin-3-one,
4-(1H-Benzimidazol-2-yl)-6-(3-fluoropyridin-4-yl)-2H-pyridazin-3-one,
2-[6-(2-Methylsulfanylpyrimidin-4-yl)-3-oxo-2,3-dihydropyridazin-4-yl]-3H-benzimidazole-5-carboxylic acid,
4-[6-(4-Methylpiperazin-1-ylmethyl)-1H-benzimidazol-2-yl]-6-phenyl-2H-pyridazin-3-one,
6-(3-Hydroxyphenyl)-4-[6-(4-methylpiperazin-1-ylmethyl)-1H-benzimidazol-2-yl]-2H-pyridazin-3-one,
4-(1H-Benzimidazol-2-yl)-6-[2-(2-morpholin-4-yl-ethylamino)pyrimidin-4-yl]-2H- pyridazin-3-one,
4-(1H-Benzimidazol-2-yl)-6-[1-(2-morpholin-4-ylethyl)-6-oxo-1,6-dihydro-pyridin-3-yl]-2H-pyridazin-3-one,
6-(3-Amino-1-methyl-1H-pyrazol-4-yl)-4-(1H-benzimidazol-2-yl)-2H-pyridazin-3-one,
4-(1H-Benzimidazol-2-yl)-6-(2-cyclopropylaminopyrimidin-4-yl)-2H-pyridazin-3-one,
4-(1H-Benzimidazol-2-yl)-6-[2-(2-hydroxy-1,1-dimethylethylamino)pyrimidin-4-yl]-2H-pyridazin-3-one,
4-(1H-Benzimidazol-2-yl)-6-(2-dimethylaminopyrimidin-4-yl)-2H-pyridazin-3-one,
4-(1H-Benzimidazol-2-yl)-6-[2-(2-methoxyethylamino)pyrimidin-4-yl]-2H- pyridazin-3-one,
{4-[5-(1H-Benzimidazol-2-yl)-6-oxo-1,6-dihydropyridazin-3-yl]pyrimidin-2- ylamino}acetic acid,
3-{4-[5-(1H-Benzimidazol-2-yl)-6-oxo-1,6-dihydropyridazin-3-yl]pyrimidin-2- ylamino}propionic acid,
4-(1H-Benzimidazol-2-yl)-6-morpholin-4-yl-2H-pyridazin-3-one,
4-(1H-Benzimidazol-2-yl)-6-[2-methylsulfanylpyrimidin-4-yl]-2H-pyridazin-3-one,
6-(4-Hydroxy-3,5-dimethylphenyl)-4-(6-[1,4]oxazepan-4-ylmethyl-1H-benz- imidazol-2-yl )-2H-pyridazin-3-one,
4-(1H-Benzimidazol-2-yl)-6-(1,5-dimethyl-6-oxo-1,6-dihydropyridin-3-yl)-2H- pyridazin-3-one,
4-(1H-Benzimidazol-2-yl)-6-imidazol-1 -yl-2H-pyridazin-3-one,
6-Chloro-4-(5-hydroxy-lH-benzimidazol-2-yl)-2H-pyridazin-3-one,
4-(1H-Benzimidazol-2-yl)-6-pyrazol-1 -yl-2H-pyridazin-3-one,
4-(1H-Benzimidazol-2-yl)-6-thiazol-4-yl-2H-pyridazin-3-one,
4-(1H-Benzimidazol-2-yl)-6-(4-hydroxy-3-methoxy-5-methylaminomethyl-phenyl)- 2H- pyridazin-3-one,
4-(1H-Benzimidazol-2-yl)-6-(1-methyl-1H-imidazol-4-yl)-2H-pyridazin-3-one,
4-(1H-Benzimidazol-2-yl)-6-[6-(2-morpholin-4-ylethylamino)pyrimidin-4-yl]-2H- pyridazin-3-one,
4-(1H-Benzimidazol-2-yl)-6-[6-(2-methoxyethylamino)pyrimidin-4-yl]-2H- pyridazin-3-one,
4-(1H-Benzimidazol-2-yl)-6-[6-(2-hydroxy-1,1-dimethylethylamino)pyrimidin-4-yl]-2H-pyridazin-3-one,
Methyl 2-[6-(2-methyl-6-methylaminopyrimidin-4-yl)-3-oxo-2,3-dihydropyridazin-4-yl]-3H-benzimidazole-5-carboxylate,
4-(1H-Benzimidazol-2-yl)-6-(2-methoxypyrimidin-4-yl)-2H-pyridazin-3-one,
4-(1H-Benzimidazol-2-yl)-6-(4-hydroxy-3-methoxy-5-oxazol-5-ylphenyl)-2H- pyridazin-3-one,
6-(3-Chlorophenyl)-4-[6-(4-methylpiperazin-1-ylmethyl)-1H-benzimidazol-2-yl]-2H-pyridazin-3-one,
4-(1H-Benzimidazol-2-yl)-6-[2-(2-morpholin-4-ylethoxy)pyrimidin-4-yl]-2H- pyridazin-3-one,
4-(1H-Benzimidazol-2-yl)-6-[2-(2-diethylaminoethylamino)pyrimidin-4-yl]-2H- pyridazin-3-one,
4-(1H-Benzimidazol-2-yl)-6-(2-cyclopropylpyrimidin-4-yl)-2H-pyridazin-3-one,
4-(1H-Benzimidazol-2-yl)-6-pyrimidin-2-yl-2H-pyridazin-3-one,
4-(1H-Benzimidazol-2-yl)-6-(4-methoxypyrimidin-2-yl)-2H-pyridazin-3-one,
4-(1H-Benzimidazol-2-yl)-6-(4-dimethylaminopyrimidin-2-yl)-2H-pyridazin-3-one,
4-(1H-Benzimidazol-2-yl)-6-[2-(2-diethylaminoethylsulfanyl)pyrimidin-4-yl]-2H- pyridazin-3-one,
4-(1H-Benzimidazol-2-yl)-6-[2-(2-hydroxy-1,1-dimethylethylamino)-6- methylpyrimidin-4-yl]-2H-pyridazin-3-one,
4-(1H-Benzimidazol-2-yl)-6-(6-methyl-2-methylaminopyrimidin-4-yl)-2H-pyridazin-3-one,
6-(3,5-Dichlorophenyl)-4-[6-(4-methylpiperazin-1-ylmethyl)-1H-benzimidazol-2- yl]-2H-pyridazin-3-one,
4-(1H-Benzimidazol-2-yl)-6-{2-[methyl-(2-morpholin-4-ylethyl)amino]pyrimidin-4- yl}-2H-pyridazin-3-one, or
4-(1H-Benzimidazol-2-yl)-6-pyrimidin-5-yl-2H-pyridazin-3-one,
or a physiologically tolerated salt thereof.

7. A pharmaceutical composition comprising the compound according to claim 1, or a physiologically acceptable salt thereof, in combination with a pharmaceutically acceptable carrier.

8. A process for preparing the compound according to claim 1, comprising reacting a compound of formula (II)

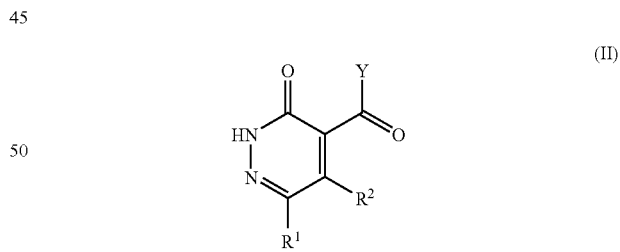

wherein Y is H, and $R^1$ and $R^2$ are as defined in claim 1, with a compound of formula (III)

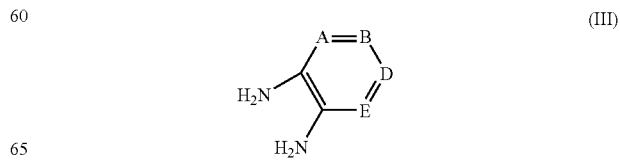

wherein A, B, D and E are as defined in claim 1, in the presence of oxygen.

9. A process for preparing the compound according to claim 1, comprising reacting a compound of formula (II)

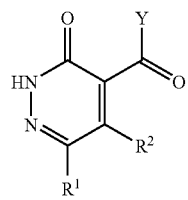
(II)

wherein Y is —OH, $C_1$-$C_{10}$-alkoxy, chlorine, —O—C(O)—($C_1$-$C_{10}$-alkyl or —O—C(O)—O—($C_1$-$C_{10}$-alkyl), and $R^1$ and $R^2$ are as defined in claim 1, with a compound of formula (III)

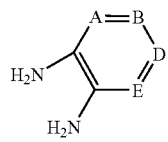
(III)

wherein A, B, D and E are as defined in claim 1, in the presence of glacial acetic acid, hydrochloric acid, sulfuric acid, phosphoric acid or phosphorus pentoxide.

10. A process for preparing the compound according to claim 1, wherein $R^1$ is optionally substituted aryl or heteroaryl as defined in claim 1, comprising:
reacting a compound of formula (VI),

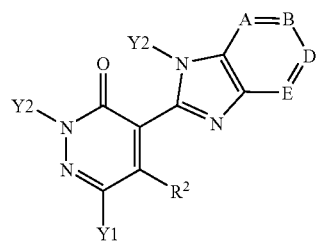
(VI)

wherein Y1 is halogen, B(OH)$_2$ or Sn($C_1$-$C_{10}$-alkyl), Y2 is H, and $R^2$, A, B, D and E are as defined in claim 1,
with a compound of formula (V), $R^1$-Z (V)

wherein Z is B(OH)$_2$, B($C_1$-$C_{10}$-alkoxy)$_2$, Sn($C_1$-$C_{10}$-alkyl)$_3$, Zn—($C_1$-$C_{10}$-alkyl) or halogen, and $R^1$ is optionally substituted aryl or heteroaryl as defined in claim 1, in the presence of a palladium complex.

11. A process for preparing the compound according to claim 1, wherein $R^1$ is optionally substituted aryl or heteroaryl as defined in claim 1, comprising:
reacting a compound of formula (VI),

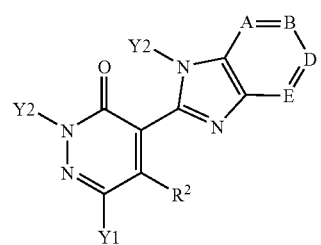
(VI)

wherein Y1 is halogen, B(OH)$_2$ or Sn($C_1$-$C_{10}$-alkyl), Y2 is a nitrogen-protecting group, and $R^2$, A, B, D and E are as defined in claim 1, with a compound of formula (V), $R^1$-Z (V)

wherein Z is B(OH)$_2$, B($C_1$-$C_{10}$-alkoxy)$_2$, Sn($C_1$-$C_{10}$-alkyl)$_3$, Zn–($C_1$-$C_{10}$-alkyl) or halogen, and $R^1$ is optionally substituted aryl or heteroaryl as defined in claim 1, in the presence of a palladium complex, to give a compound of formula (Ia)

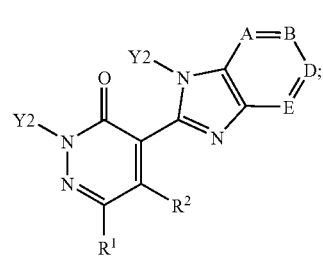
(Ia)

and removing the nitrogen-protecting group Y2 of the compound of formula (Ia).

\* \* \* \* \*